(12) United States Patent
Temme

(10) Patent No.: US 11,578,307 B2
(45) Date of Patent: Feb. 14, 2023

(54) ARTIFICIAL HLA-POSITIVE FEEDER CELL LINES FOR NK CELLS AND USES THEREOF

(71) Applicant: TECHNISCHE UNIVERSITAT DRESDEN, Dresden (DE)

(72) Inventor: Achim Temme, Dresden (DE)

(73) Assignee: TECHNISCHE UNIVERSITAT DRESDEN, Dresden (DE)

( * ) Notice: Subject to any disclaimer, the term of this patent is extended or adjusted under 35 U.S.C. 154(b) by 0 days.

(21) Appl. No.: 17/293,895

(22) PCT Filed: Nov. 22, 2019

(86) PCT No.: PCT/EP2019/082283
§ 371 (c)(1),
(2) Date: May 13, 2021

(87) PCT Pub. No.: WO2020/104676
PCT Pub. Date: May 28, 2020

(65) Prior Publication Data
US 2021/0355446 A1    Nov. 18, 2021

(30) Foreign Application Priority Data
Nov. 23, 2018    (EP) .................................... 18208092

(51) Int. Cl.
*C12N 5/0783* (2010.01)
*A61K 35/17* (2015.01)
*C07K 14/74* (2006.01)

(52) U.S. Cl.
CPC ............ *C12N 5/0646* (2013.01); *A61K 35/17* (2013.01); *C12N 2501/2302* (2013.01); *C12N 2501/2315* (2013.01); *C12N 2501/58* (2013.01); *C12N 2501/998* (2013.01); *C12N 2510/00* (2013.01)

(58) Field of Classification Search
None
See application file for complete search history.

(56) References Cited

U.S. PATENT DOCUMENTS

2015/0224143 A1    8/2015 Malmberg et al.

FOREIGN PATENT DOCUMENTS

| WO | 2012146702 A1 | 11/2012 |
| WO | 2016069607 A1 | 5/2016 |
| WO | 2018055152 A1 | 3/2018 |

OTHER PUBLICATIONS

Michen et al (Cytotherapy, 2020, 22: 354-368) (Year: 2020).*
Edwards et al (JMB, 2003, 334: 103-118) (Year: 2003).*
Lloyd et al (Protein Engineering, Eng. Design & Selection, 2009, 22(3): 159-168) (Year: 2009).*
Goel et al (J. Immunol., 2004, 173: 7358-7367) (Year: 2004).*
Khan and Salunke (J. Immunol, 2014, 192: 5398-5405) (Year: 2014).*
Poosarla et al (Biotechn. Bioeng., 2017, 114(6): 1331-1342) (Year: 2017).*
Torres and Casadevall (Trend. Immunol., 2008, 29(2): 91-97) (Year: 2008).*
A. Mandal (news-medical.net/health/What-are-Cytokines.aspx, 2019, 3 pages) (Year: 2019).*
Fujisaki et al: "Expansion of highly cytotoxic human natural killer cells for cancer therapy". Cancer Research, Proceedings: AACR Annual Meeting 2014; Apr. 5-9, 2014; San Diego, CA, vol. 69, No. 9, May 1, 2009 (May 1, 2009), pp. 4010-4017.
Denman et al: "Membrane-Bound IL-21 Promotes Sustained Ex Vivo Proliferation of Human Natural Killer Cells". PLOS ONE, vol. 7, No. 1, Jan. 18, 2012 (Jan. 18, 2012), DOI: 10.1371/journal.pone. 0030264 pp. 1-13.
Topfer et al: "DAP12-Based Activating Chimeric Antigen Receptor for NK Cell Tumor Immunotherapy", The Journal of Immunology, vol. 194. No. 7. Mar. 4, 2015 (Mar. 4, 2015), pp. 3201-3212.
Prod'Homme et al: "Human Cytomegalovirus UL40 Signal Peptide Regulates Cell Surface Expression of the NK Cell Ligands HLA-E and gpUL18", The Journal of Immunology, vol. 188. No. 6, Feb. 15, 2012 (Feb. 15, 2012), pp. 2794-2804.
Fan et al: "Review of Immune Therapies Targeting Ovanan Cancer", Current Treatment Options in Oncology, May 2005, Springer US. Boston, vol. 19, 74, Nov. 14, 2018 (Nov. 14, 2018), pp. 1-21.

(Continued)

*Primary Examiner* — G. R. Ewoldt
*Assistant Examiner* — Marianne DiBrino
(74) *Attorney, Agent, or Firm* — Olson & Cepuritis, Ltd.

(57) ABSTRACT

The present invention relates to the field of immunology, molecular biology and therapeutics. In particular, the invention relates to novel artificial feeder cells for activation and expansion of natural killer (NK) cells. The artificial feeder cell expresses endogenous ligands (HLA C1, C2, 5 and Bw4 type) for killer cell immunoglobulin-like receptors (KIRs), non-KIR binding Bw6 ligand, endogenous HLA-E-ligand for inhibitory NKG2A receptor, and comprises at least one stimulatory cytokine either membrane bound or secreted or at least one co-stimulatory ligand where those ligands and cytokines each specifically bind to a cognate receptor on a NK cell of interest, thereby mediating expansion of the NK cell. The invention can be used as an "off the 10 shelf" artificial feeder cell that can be readily designed to expand a NK cell or a NK subset of interest and also specifically expand NK cells modified with a chimeric antigen receptor (CAR). By genetically introducing or knockdown of candidate genes, the artificial feeder cell of the invention can be used to identify the stimulatory, co-stimulatory, and any other factors that mediate growth, expansion and cytotoxicity of a NK cell. Thus, the present invention provides 15 powerful tools for development of novel therapeutics where activation and expansion of the NK cell and of the CAR-NK cell can provide a benefit.

17 Claims, 51 Drawing Sheets
Specification includes a Sequence Listing.

(56) References Cited

OTHER PUBLICATIONS

Liu et al: "Ex Vivo Expanded Adaptive NK Cells Effectively Kill Primary Acute Lymphoblastic Leukemia Cells". Cancer Immunology Research, vol. 5, No. 8, Aug. 1, 2017 (Aug. 1, 2017). pp. 654-665.

Sharma, et al: "TL-2 mediates NK cell proliferation but not hyperactivity". Immunologic Research. Humana Press. Inc., vol. 66, Dec. 19, 2017 (Dec. 19, 2017), pp. 151-157.

Zhang, et al: 11 Blockade of the checkpoint receptor TIGIT prevents NK cell exhaustion and elicits potent anti-tumor immunity, Nature Immunology, Nature Publishing Group, US, New York. pp. 723-732 vol. 19, Jun. 18, 2018 (Jun. 18, 2018).

Leong et al: "Preactivation with IL-12. IL-15. and IL-18 Induces CD25 and a Functional High-Affinity IL-2 Receptor on Human Cytokine-Induced Memory-like Natural Killer Cells", Biology of Blood and Marrow Transplantation. vol. 20, pp. 463-473.

\* cited by examiner

|  | HLA-B and HLA-C genotypes | Predicted Ligands for Donor | Matched in GvH direction (Host: PC3$^{PSCA}$) |
|---|---|---|---|
| Donor 1 | B*07:02, B*07:02<br>C*07:02, C*07:02 | Bw6, Bw6<br>C1, C1 | yes |
| Donor 2 | B*07:02, B*40:02<br>C*07:02, C02:02 | Bw6, Bw6<br>C1, C2 | yes |
| Donor 3 | B*07, B*08<br>C*07, C*07 | Bw6, Bw6<br>C1, C1 | yes |
| Donor 4 | B*15:18, B*35:01<br>C*07:04, C*04:01 | Bw6, Bw6<br>C1, C2 | yes |
| Donor 5 | B*41:02, B*08:01<br>C07:01, C*17:01 | Bw6, Bw6<br>C1, C2 | yes |

H

PC3^PSCA-IL2-
HLA-E-UL40-VMAPRTLIL

I

PC3^PSCA-IL2-
HLA-E-UL40-VMAPRTLFL

J

PC3^PSCA-IL2-mIL-15d-
HLA-E-UL40-VMAPRTLIL

K

PC3^PSCA-IL2-
HLA-E-UL40-VMAPRTLFL

Fig. 18

SEQ ID NO: 5          HLA-E-UL40-VMAPRTLIL

MSRSVALAVLALLSLSGLEAVMAPRTLILGGGGGGSGAPGSGGGSIQRTPKIQVYSRHPA
ENGKSNFLNCYVSGFHPSDIEVDLLKNGERIEKVEHSDLSFSKDWSFYLLYYTEFTPTEK
DEYACRVNHVTLSQPKIVKWDRDM*RSASGGGGSGGGGSGGGG*SASGGGGSHSLKYFHTSV
SRPGRGEPRFISVGYVDDTQFVRFDNDAASPRMVPRAPWMEQEGSEYWDRETRSARDTAQ
IFRVNLRTLRGCYNQSEAGSHTLQWMHGCELGPDGRFLRGYEQFAYDGKDYLTLNEDLRS
WTAVDTAAQISEQKSNDASEAEHQRAYLEDTCVEWLHKYLEKGKETLLHLEPPKTHVTHH
PISDHEATLRCWALGFYPAEITLTWQQDGEGHTQDTELVETRPAGDGTFQKWAAVVVPSG
EEQRYTCHVQHEGLPEPVTLRWKPASQPTIPIVGIIAGLVLLGSVVSGAVVAAVIWRKKS
SGGKGGSYSKAEWSDSAQGSESHSL

Fig. 19

SEQ ID NO: 6          HLA-E-UL40-VMAPRTLFL

MSRSVALAVLALLSLSGLEAVMAPRTLFLGGGGGGSGAPGSGGGSIQRTPKIQVYSRHPA
ENGKSNFLNCYVSGFHPSDIEVDLLKNGERIEKVEHSDLSFSKDWSFYLLYYTEFTPTEK
DEYACRVNHVTLSQPKIVKWDRDM*RSASGGGGSGGGGSGGGG*SASGGGGSHSLKYFHTSV
SRPGRGEPRFISVGYVDDTQFVRFDNDAASPRMVPRAPWMEQEGSEYWDRETRSARDTAQ
IFRVNLRTLRGCYNQSEAGSHTLQWMHGCELGPDGRFLRGYEQFAYDGKDYLTLNEDLRS
WTAVDTAAQISEQKSNDASEAEHQRAYLEDTCVEWLHKYLEKGKETLLHLEPPKTHVTHH
PISDHEATLRCWALGFYPAEITLTWQQDGEGHTQDTELVETRPAGDGTFQKWAAVVVPSG
EEQRYTCHVQHEGLPEPVTLRWKPASQPTIPIVGIIAGLVLLGSVVSGAVVAAVIWRKKS
SGGKGGSYSKAEWSDSAQGSESHSL

Fig. 20

SEQ ID NO: 7                    PSCA pre-pro-protein

MAGLALQPGTALLCYSCKAQVSNEDCLQVENCTQLGEQCWTARIRAVGLLTVISKGCSLN
CVDDSQDYVGKKNITCCDTDLCNASGAHALQPAAAILALLPALGLLLWGPGQL

Fig. 21

SEQ ID NO: 8                    EGFRvIII

MRPSGTAGAALLALLAALCPASRALEEKKGNYVVTDHGSCVRACGADSYEMEEDGVRKCK
KCEGPCRKVCNGIGIGEFKDSLSINATNIKHFKNCTSISGDLHILPVAFRGDSFTHTPPL
DPQELDILKTVKEITGFLLIQAWPENRTDLHAFENLEIIRGRTKQHGQFSLAVVSLNITS
LGLRSLKEISDGDVIISGNKNLCYANTINWKKLFGTSGQKTKIISNRGENSCKATGQVCH
ALCSPEGCWGPEPRDCVSCRNVSRGRECVDKCNLLEGEPREFVENSECIQCHPECLPQAM
NITCTGRGPDNCIQCAHYIDGPHCVKTCPAGVMGENNTLVWKYADAGHVCHLCHPNCTYG
CTGPGLEGCPTNGPKIPSIATGMVGALLLLLVVALGIGLFMRRRHIVRKRTLRRLLQERE
LVEPLTPSGEAPNQALLRILKETEFKKIKVLGSGAFGTVYKGLWIPEGEKVKIPVAIKEL
REATSPKANKEILDEAYVMASVDNPHVCRLLGICLTSTVQLITQLMPFGCLLDYVREHKD
NIGSQYLLNWCVQIAKGMNYLEDRRLVHRDLAARNVLVKTPQHVKITDFGLAKLLGAEEK
EYHAEGGKVPIKWMALESILHRIYTHQSDVWSYGVTVWELMTFGSKPYDGIPASEISSIL
EKGERLPQPPICTIDVYMIMVKCWMIDADSRPKFRELIIEFSKMARDPQRYLVIQGDERM
HLPSPTDSNFYRALMDEEDMDDVVDADEYLIPQQGFFSSPSTSRTPLLSSLSATSNNSTV
ACIDRNGLQSCPIKEDSFLQRYSSDPTGALTEDSIDDTFLPVPEYINQSVPKRPAGSVQN
PVYHNQPLNPAPSRDPHYQDPHSTAVGNPEYLNTVQPTCVNSTFDSPAHWAQKGSHQISL
DNPDYQQDFFPKEAKPNGIFKGSTAENAEYLRVAPQSSEFIGAGAGPRRMRPPTPGEGRG
SLLTCGDVEENPGPGTAMTEYK

Fig. 22

SEQ ID NO: 9              human IL-2

MYRMQLLSCIALSLALVTNSAPTSSSTKKTQLQLEHLLLDLQMILNGINNYKNPKLTRML

TFKFYMPKKATELKHLQCLEEELKPLEEVLNLAQSKNFHLRPRDLISNINVIVLELKGSE

TTFMCEYADETATIVEFLNRWITFCQSIISTLT

Fig. 23

SEQ ID NO: 10              mIL-15d

MRISKPHLRSISIQCYLCLLLNSHFLTEAGIHVFILGCFSAGLPKTEANWVNVISDLKKI

EDLIQSMHIDATLYTESDVHPSCKVTAMKCFLLELQVISLESGDASIHDTVENLIILANN

SLSSNGNVTESGCKECEELEEKNIKEFLQSFVHIVQMFINTS*GGSGGS*ACVNEQKLISEE

DL*GGS*QAQSDCSCSTVSPGVLAGIVMGDLVLTVLIALAVYFLGRLVPRGRGAAEAATRKQ

RITETESPSQELQGQRSDVSSDL

Fig. 24

SEQ ID NO: 11              4-1BBL

MEYASDASLDPEAPWPPAPRARACRVLPWALVAGLLLLLLLAAACAVFLACPWAVSGARA

SPGSAASPRLREGPELSPDDPAGLLDLRQGMFAQLVAQNVLLIDGPLSWYSDPGLAGVSL

TGGLSYKEDTKELVVAKAGVYYVFFQLELRRVVAGEGSGSVSLALHLQPLRSAAGAAALA

LTVDLPPASSEARNSAFGFQGRLLHLSAGQRLGVHLHTEARARHAWQLTQGATVLGLFRV

**TPEIPAGLPSPRSES*YTDIEMNRLGK***

Fig. 25

SEQ ID NO: 12              scFv(9E10)-tm

MAKANLLVLLCALAAADAGSEVHLVESGGDLVKPGGSLKLSCAASGFTFSHYGMSWVRQT
PDKRLEWVATIGSRGTYTHYPDSVKGRFTISRDNDKNALYLQMNSLKSEDTAMYYCARRS
EFYYYGNTYYYSAMDYWGQGASVTVSSAKTTPKLEEGEFSEARVDIVLTQSPASLAVSLGQR
ATISCRASESVDNYGFSFMNWFQQKPGQPPKLLIYAISNRGSGVPARFSGSGSGTDFSLN
IHPVEEDDPAMYFCQQTKEVPWTFGGGTKLEIKGGGGSGYTDIEMNRLGKGGGSGGGGSA
SGGGHHHHHHRPQQPTIPIVGIIAGLVLLGSVVSGAVVAAVIWRKKSSGGKGGSYSKAEW
SDSAQGSESHSL

Fig. 26

SEQ ID NO: 13              human DAP12

MGGLEPCSRLLLLPLLLAVSGLRPVQAQAQSDCSCSTVSPGVLAGIVMGDLVLTVLIALA
VYFLGRLVPRGRGAAEAATRKQRITETESPYQELQGQRSDVYSDLNTQRPYYK

Fig. 27

SEQ ID NO: 14              scFv(MR1.1)

METDTLLLWVLLLWVPGSTGDAQVKLQQSGGGLVKPGASLKLSCVTSGFTFRKFGMSWVR
QTSDKRLEWVASISTGGYNTYYSDNVKGRFTISRENAKNTLYLQMSSLKSEDTALYYCTR
GYSPYSYAMDYWGQGTTVTVSSSGGGSGGGGSGGGGSDIELTQSPASLSVATGEKATIRC
MTSTDIDDDMNWYQQKPGEPPKFLISEGNTLRPGVPSRFSSGTGTDFVFTIENTLSEDV
GDYYCLQSWNVPLTFGDGTKLE

Fig. 28

SEQ ID NO: 15          scFv(AM1)

METDTLLLWVLLLWVPGSTGDAAQPARRARRTKLGTELGSQVKLQESGGGLVQPGGSLKL
SCVASGFTFSSYTMSWVRRTPEKRLEWVAYIHNGGGHTYYPDTIKGRFTISRDNAKNTLF
LEMSSLKSEDTAMYYCTRRMYYGNSHWYFDVWGAGTSVTVSSAKTTPPSVY*GGGGSGGGG
SGGGGS*TNSDIVMTQSPSSLSASLGDRVTINCRTSQDISNYLNWYQLTPDGTVKLLIYYT
LKLNSGVPSRFSGSGSGTDYSLTINNLEKEDFATYFCQQSKTLPWTFGGGTKLEIKRADA
APTVSGP

Fig. 29

SEQ ID NO: 16          anti-PSCA-CAR

METDTLLLWVLLLWVPGSTGDAAQPARRARRTKLGTELGSQVKLQESGGGLVQPGGSLKL
SCVASGFTFSSYTMSWVRRTPEKRLEWVAYIHNGGGHTYYPDTIKGRFTISRDNAKNTLF
LEMSSLKSEDTAMYYCTRRMYYGNSHWYFDVWGAGTSVTVSSAKTTPPSVY*GGGGSGGGG
SGGGGS*TNSDIVMTQSPSSLSASLGDRVTINCRTSQDISNYLNWYQLTPDGTVKLLIYYT
LKLNSGVPSRFSGSGSGTDYSLTINNLEKEDFATYFCQQSKTLPWTFGGGTKLEIKRADA
APTVSGP*GGSGGSACVN*EQKLISEEDL*GGS*QAQSDCSCSTVSPGVLAGIVMGDLVLTVLI
ALAVYFLGRLVPRGRGAAEAATRKQRITETESPYQELQGQRSDVYSDLNTQRPYYK

Fig. 30

SEQ ID NO: 17　　　　　　　　anti-EGFRvIII-CAR

METDTLLLWVLLLWVPGSTGDAQVKLQQSGGGLVKPGASLKLSCVTSGFTFRKFGMSWVR
QTSDKRLEWVASISTGGYNTYYSDNVKGRFTISRENAKNTLYLQMSSLKSEDTALYYCTR
GYSPYSYAMDYWGQGTTVTV*SSSGGGSGGGGSGGGGS*DIELTQSPASLSVATGEKATIRC
MTSTDIDDDMNWYQQKPGEPPKFLISEGNTLRPGVPSRFSSSGTGTDFVFTIENTLSEDV
GDYYCLQSWNVPLTFGDGTKLE*SGGSGGS*ACVNEQKLISEEDLGGS**QAQSDCSCSTVSPG
VLAGIVMGDLVLTVLIALAVYFLGRLVPRGRGAAEAATRKQRITETESPYQELQGQRSDV
YSDLNTQRPYYK**

Fig. 31

SEQ ID NO: 18　　　　　　　　Ia-myc-DAP12

MGGLEPCSRLLLLPLLLAVSGLRPVQAQAQ*AAGGRGMSGGGS*KPLPEVTDEYGGGSSSAS*
*GGTELGSQVKLQESGGGSGGSACVN*EQKLISEEDLGGS**QAQSDCSCSTVSPGVLAGIVMG
DLVLTVLIALAVYFLGRLVPRGRGAAEAATRKQRITETESPYQELQGQRSDVYSDLNTQR
PYYKG**

US 11,578,307 B2

ARTIFICIAL HLA-POSITIVE FEEDER CELL LINES FOR NK CELLS AND USES THEREOF

CROSS-REFERENCE TO RELATED APPLICATIONS

This application is a U.S. National Stage of PCT/EP2019/082283, filed Nov. 22, 2019, claiming priority to EP Application No. 18208092.9 filed Nov. 23, 2018, both of which are incorporated herein by reference.

Sequence Listing Incorporation

Biological sequence information for this application is included in an ASCII text file, having the file name "TUD122WO_2019-11-15_Sequence_Listing_ST25.txt" and a having file size of 43794 bytes, created on May 13, 2021. This Sequence Listing is incorporated herein by reference.

FIELD OF INVENTION

The present invention relates to the field of immunology, molecular biology and therapeutics. In particular, the invention relates to novel artificial feeder cells for activation and expansion of natural killer (NK) cells. The artificial feeder cell expresses endogenous ligands (HLA C1, C2, and Bw4 type) for killer cell immunoglobulin-like receptors (KIRs), non-KIR binding Bw6 ligand, endogenous HLA-E-ligand for inhibitory NKG2A receptor, and comprises at least one stimulatory cytokine either membrane bound or secreted or at least one co-stimulatory ligand where those ligands and cytokines each specifically bind to a cognate receptor on a NK cell of interest, thereby mediating expansion of the NK cell. The invention can be used as an "off the shelf" artificial feeder cell that can be readily designed to expand a NK cell or a NK subset of interest and also specifically expand NK cells modified with a chimeric antigen receptor (CAR). By genetically introducing or knockdown of candidate genes, the artificial feeder cell of the invention can be used to identify the stimulatory, co-stimulatory, and any other factors that mediate growth, expansion and cytotoxicity of a NK cell. Thus, the present invention provides powerful tools for development of novel therapeutics where activation and expansion of the NK cell and of the CAR-NK cell can provide a benefit.

BACKGROUND AND DESCRIPTION OF THE RELATED ART

Natural killer (NK) cells develop from CD34+ hematopoietic progenitors, are characterized by CD56+CD3− surface expression and comprise about 5-15% of circulating lymphocytes. They belong to the innate immune system and stand at the first defense line against viruses and transformed cells. NK cells use an array of germline-encoded activating and inhibitory receptors which are epigenetically regulated in a stochastic, variegated pattern, resulting in an overlapping diversity of NK cell subsets [1, 2]. With their receptors NK cells sense virus-infected cells or malignant cells displaying altered surface expression of activating and inhibitory NK cell ligands. They exert potent cytotoxic responses to cellular targets and thus are candidate effector cells for immunotherapy of cancer and of viral infections. NK cells receiving appropriate activating signals expand, release cytokines such as interferon (IFN)-γ, and kill target cells via the perforin-granzyme pathway or via death-receptor ligands [3, 4]. Tolerance of NK cells for self is mainly achieved by inhibitory killer cell immunoglobulin-like receptors (KIRs) and CD94/NKG2A-receptors on NK cells for HLA class I molecules on somatic cells [3]. Interactions of those inhibitory receptors with HLA class I molecules on autologous normal cells induce dominant negative signals which override activating signals and therefore prevent cytotoxic activity as defined by the "missing-self" hypothesis [5, 6]. The inhibitory heterodimer CD94/NKG2A binds to non-classical HLA-E presenting an HLA class I leader peptide [7, 8]. Thereby CD94/NKG2A indirectly senses the presence of HLA class I on cells. The genes encoding the inhibitory KIR receptors are inherited as haplotypes, and are most variable in terms of both gene content and sequence polymorphism [9, 10]. For the dominant inhibitory KIRs their cognate ligands have been identified: KIR2DL2/3 and KIR2DL1 recognize C1 and C2 ligands from the HLA-C locus, respectively [11-13]. Weaker ligands include the Bw4 motif of HLA-B alleles and some HLA-molecules which are recognized by KIR3DL1 and certain HLA-A3 and HLA-A11 alleles which bind to KIR3DL2 [14-16]. So far no KIR has been detected in humans which binds the Bw6 motif of HLA-B alleles, so the Bw6 motif defines "non-KIR binding" alleles. Another inhibitory receptor, the immunoglobulin-like transcript 2 (ILT2) expressed on NK cell subsets, also designated leukocyte immunoglobulin-like receptor subfamily B member 1 (LIRLB1) or CD85j binds to a broad range of HLA class I molecules [17]. All inhibitory NK cell receptors in humans contain at least one intracellular immunoreceptor tyrosine-based inhibitory motif (ITIM), which recruits and activates SHP-1- and SHIP-1 phosphatases associated with inhibitory NK cell signaling [3].

Human peripheral NK cells are generally divided in tow subsets based on relative CD56 surface expression. CD56bright cells only account for a minority of peripheral blood NK cells (~10%) and develop from hematopoietic stem cells [18]. Experimental evidence supports the notion that CD56dim NK cells, which accounts for approximately for 90% of peripheral blood NK cells, develop from CD56bright cells [19, 20]. During this development, CD56dim NK cells lose expression of NKG2A inhibitory receptor and acquire the expression of at least one KIR. Terminally differentiated CD56dim NK cells are furthermore characterized by the CD57 surface marker. Notably, this maturation process from CD56bright to CD56dim NK cells is unidirectional [19]. The CD56bright NK cell subset differs from the CD56dim subset by a higher proliferative potential [19] which is an important issue when considering methods for expansion of NK cells or NK cell subsets. Whereas transplanted CD56bright/NKG2A+ NK cells cannot elicit alloreactivity, transplanted CD56dim NK cells with a single KIR or more can exhibit alloreactivity when sensing absence of the cognate recipient HLA class I ligand(s) (cognate KIR-ligand(s)).

In particular, in human stem cell transplantation (HSCT) and adoptive NK cell therapy for treatment of leukemia, alloreactive donor cells are employed for achieving a graft versus leukemia effect. However, the beneficial clinical effect of NK-cell alloreactivity has not been uniformly demonstrated, likely reflecting differences in conditioning regimens, graft product and post-transplant immune suppression [21-23].

In the past immunotherapy with NK cells has often been limited by the inability to obtain sufficient numbers of pure NK cell populations for cancer treatment. To date, NK cell expansion can be greatly enhanced by feeder cells derived from tumor cell lines or PBMCs. Therefore, co-culture systems of irradiated feeder cells and NK cells in media containing IL-2, IL-15 and IL-21 have been developed to generate large numbers of NK cells. Commonly used feeder cell lines are Epstein-Barr Virus (EBV)-transformed 721.221, EBV-transformed B cells (EBV-LCLs), EBV-/bcr-ab/-transformed RPM18866 and bcr-ab/-transformed K562 [24-27]. Stimulation with NK-sensitive K562 cells, which lacks protective HLA class I expression, is known to augment NK cell proliferation to IL-2, IL-15, and IL-21 in combination [26, 28]. In a further development K562 cells were genetically modified to express 4-1 BBL (CD137L) plus membrane-bound IL-15 or loading endogenous IL15Rα on K562 cells with recombinant human (rh)IL-15 to provide juxtacrine signaling to NK cells. 4-1 BBL and IL-15 signaling acts synergistically with exogenously added rhIL-2 to augment K562-specific NK stimulatory capacity, resulting in strong expansion of peripheral blood NK cells without concomitant growth of T lymphocytes [29, 30].

A method for large-scale clinical grade expansion of NK cells based on irradiated K562-mIL15-4-1 BBL and rhIL-15-loaded K562-4-1 BBL feeder cells is used in clinical studies and represents the state of the art for expanding NK cells to large numbers for immunotherapy of cancer [31, 32]. However, NK cell expansion technology using these artificial feeder cells and of similar so far described K562-derivatives modified with for instance membrane-bound MIC-A plus 4-1-BBL [33] or membrane-bound IL-21 plus 4-1 BBL [34], comes along with the probability of unwanted off-target effect, which limits its clinical use. So far all K562-derived artificial feeder cells are lethally irradiated prior use, which induces stress-induced NK cell ligands (induced self) such as MHC class I polypeptide-related sequence A/B (MIC-A/B) or UL-16 binding proteins (ULBPs) which bind to the activating NK cell receptor NKG2D [35, 36]. Furthermore these K562 feeder cells lacks protective HLA-class I expression and consequently expansion of co-cultivated NK cells is pre-dominantly achieved by "missing self" [35] in combination with "induced self" [36] recognition and hyper-activation through IL-15/4-1 BBL or mIL-21/4-1 BBL with concomitant exogenous delivery of rhIL-2. When transplanted, such expanded NK cells have a higher intrinsic capacity to cause an unwanted "Graft versus Host Disease" (GvHD) as observed in matched unrelated donor and matched sibling donor recipients receiving IL-15/4-1 BBL-activated NK cells or recipients receiving mIL-21/4-1 BBL-activated allogeneic NK cells [31, 37]. The development of a HLA-class I-positive feeder cell line, which limits "missing self" and "induced self"-driven expansion and restrains the development of hyperactive NK cells might be advantageous and has not been pursuit so far.

Furthermore, for continuous expansion of NK cells with K562-derived artificial feeder cells it is mandatory to consecutively add fresh rhIL-2 or rhIL-15 or to consecutively add fresh rhIL-2 in combinatorial use with rhIL-15, rhIL-21 and rhIL-18, respectively, to the cell culture medium. A feeder cell line further genetically engineered to secrete moderate amounts of interleukin allowing the fully independent proliferation of NK cells would save costs, would be advantageous for preclinical research as well as for clinical use and has not been described thus far.

A further promising approach to fight cancer cells is based on a subset of highly differentiated CD56dim NK cells, usually termed "adaptive" or "memory-like" NK cells. Such NK cells are characterized by acquisition of the activating NKG2C receptor and CD57, are devoid of NKG2A inhibitory receptor and display strong expression of unique KIR repertoires [19, 38]. It is well known that inhibitory NKG2A binds with higher affinity to HLA-E presenting nonameric peptides derived from classical HLA molecules than the activating NKG2C [39]. Increasing frequencies of NKG2C cells occurs naturally in vivo in response to human cytomegalovirus (HCMV) infection and higher frequencies of NKG2C+ NK cells are frequently observed in HCMV-seropositive donors [40, 41]. During infection HCMV downregulates classical HLA-expression of infected cells and therefore evades recognition by T-cells. To evade missing self-recognition and destruction by NK cells, HCMV upregulates classical HLA-homologues [42] and stabilizes HLA-E surface expression levels through loading of HLA-E with nonamer peptides derived from the signal sequence from the viral UL40 protein which are identical to nonamer peptides derived from signal sequences of HLA class I molecules and non-classical HLA-G [41, 43, 44]. Consequently, when confronted with HCMV-infected cells, cytotoxicity of CD94/NKG2A-positive NK cells is dampened whereas CD94/NKG2C-positive NK cells can react against HCMV-infected cells.

Recent efforts disclosed in WO2014037422 focused on expansion of NKG2C+/CD57+-positive NK cells originating from relatively less-differentiated KIR-positive NKG2C+/CD57− NK cells using 722.221-derived feeder cells genetically modified with an artificial HLA-A2-signal-peptide-HLA-E (AEH), which serves as ligand for NKG2A and C. By implementing single expression of HLA C1, C2 and Bw4 in the 722.221-AEH feeder cell line, a skewing of NKG2C+NK cells from peripheral blood to alloreactive single KIR-positive NK cell products for cancer therapy was demonstrated. More specifically, WO2014037422 disclose that skewing of the NK cell population to differentiated single inhibitory KIR-positive NK cells with simultaneous expression of NKG2C+/CD57+, which showed an enhanced alloreactivity towards target cells lacking the cognate self KIR-ligand. So far, this method represents the state of the art for producing NKG2C+ NK cells. A major unresolved problem of this method for selective expansion of NKG2C+ NK cells is disclosed in an accompanying publication to WO2014037422 and relates to the low expansion rate of in the mean of 2.4-fold. Therefore, said method is not sufficient to enable production of clinical relevant cell numbers for adoptive cell therapy [45]. Furthermore, said method for the selective expansion of NKG2C+ NK cells still relies on exogenously given recombinant human cytokines. A feeder cell line enabling an autonomous and efficient selective expansion to produce a highly pure NKG2C+ NK cell product and devoid of NKG2A expression would be advantageous for preclinical research as well as for clinical use and has not been described thus far.

Another hurdle when considering NKG2C+ NK cells for adoptive cellular therapy relates to the often low frequency of NKG2C+ NK cells in donors which is accompanied by the inability to expand those cells to meaningful numbers and purity [46]. Therefore, a method, which enables selective and efficient expansion of NKG2C+ NK cells from donors lacking pre-existing expansions, more specifically having NKG2C+ NK cell frequencies below 15%, is needed. Accomplishing this objective will improve adoptive cell therapy with NKG2C+ NK cells in the autologous as well as in the allogeneic setting.

Conceptually, for production of clinical relevant numbers of NKG2C NK cells, it is essential to use a cell subset with high proliferative capacity, namely CD56bright NK cells that represent 5-10% of peripheral blood NK cells instead of differentiated KIR+/NKG2C+/CD57+ or less differentiated KIR+/NKG2C+/CD57− NK cells having less proliferative capacity. A method which promotes expansion of CD56bright NK cells and at the same time enables CD56bright NK cells to differentiate into NKG2C+ NK cell subsets has not been described so far and is highly desired.

Another promising immunotherapeutic approach, which utilizes NK cells, is based on chimeric antigen receptors (CARs). CARs redirect immune effector cells towards surface exposed tumor-associated antigens (TAAs) [47]. They are usually designed by fusing the TAA-specific variable domains of an antibody to intracellular signaling domains of immunoreceptors and co-stimulatory molecules (i.e. CD34, CD28, 4-1 BB) [47]. The genetic engineering of T cells with CARs (CAR-T cells) has been demonstrated to confer a high-affinity specific recognition of TAAs in an human leukocyte antigen (HLA) class I-independent fashion and can result in efficient tumor cell death and tumor regression in cancer patients [47, 48].

CAR-modified NK cells (CAR-NK cells) may have several advantages when compared to CAR-T cells. They are short-lived effector cells, which in contrast to CAR-T cells would not need "suicide genes" to prevent long lasting "on-target off tissue" effects [4, 49]. In comparison to T cells the cytokine-production profile of NK cells mainly consists of IFN-γ, tumor necrosis factor (TNF)-α and granulocyte macrophage colony-stimulating factor (GM-CSF) and is devoid of IL-2 [50-52]. In particular IL-2 amplifies deleterious off-target side effects such as cytokine release syndrome [53-55] and brain edema [56, 57], which occurred with CAR-T cells encountering high numbers of TAA-positive targets or unforeseen target gene expression on healthy tissue. In this regard, normal tissues displaying moderate TAA levels might have sufficient amounts of protective HLA class I molecules, which limit cytotoxic activity of CAR-NK cells.

To date, retro- and lentiviral transductions are currently the most utilized method to genetically modify NK cells and represent the state of the art for manufacturing CAR-NK cells with stable expression of the transgene. Further protocols to genetically modify NK cells include trogocytosis and electroporation of mRNA [58, 59]. However, both methods only provide transient expression of the CAR which limits effectiveness in vivo [58, 59]. So far, due to the intrinsic resistance of NK cells, their transduction with retroviral and lentiviral vectors has been a major challenge [60]. Furthermore, although CAR-NK cells maintain their effector function, their expansion to clinical applicable numbers remained a major hurdle and has not been solved so far. Therefore, a method for selective expansion of CAR-NK cells after genetic manipulation is highly needed and would represent a substantial step towards the clinical use of CAR-NK cells.

SUMMARY OF THE INVENTION

To overcome the obstacles of the prior art, the present invention provides in a first aspect a method for specifically inducing proliferation and expansion of human NK cells with artificial feeder cells, said method comprising contacting said NK cells with artificial feeder cells, wherein said artificial feeder cells are genetically engineered and comprise an expression vector which expresses at least one cytokine and additionally co-stimulatory ligand(s) or activating surface molecule(s).

In a preferred embodiment, the method of the invention comprises the specific induction of the proliferation and expansion of a NK cell subset expressing an activating NK cell receptor chosen from Natural Cytotoxicity Receptors (NCRs), small-tailed KIRs or NKG-receptors, comprising contacting a NK bulk cell population containing the NK subpopulation of interest with artificial feeder cells which are genetically engineered and comprise an expression vector which expresses the cognate NK cell ligand for the activating NK cell receptor. In an alternative embodiment of this aspect of the invention, the artificial feeder cell line is loaded with activating peptides on HLA-E molecules specific for activating NKG2 cell receptors of the NK subpopulation of interest. In a further alternative of this aspect of the invention, the artificial feeder cell line is engineered and expresses a membrane-bound antibody specific for the activating NK cell receptor of the NK subpopulation of interest.

In a further preferred embodiment, the method of the invention comprise the specific induction of the proliferation and expansion of genetically engineered NK cells displaying an artificial chimeric antigen receptor (CAR), comprising contacting a NK cell population containing CAR-NK cells with artificial feeder cells which endogenously express the cognate surface antigen for the CAR or are genetically engineered and comprise an expression vector which expresses the cognate surface antigen for the CAR, wherein said cognate antigen is represented by viral and tumor-associated antigens (TAAs). In an alternative of this aspect of the invention, the artificial feeder cell line is engineered and expresses a membrane-bound antibody specific for an epitope-tag implemented in the CAR.

The invention further relates to the use of NK cells, NK-subsets or CAR-NK cells, which were expanded according to the method described herein as a medicament (i.e. Advanced Therapy Medicinal Product (ATMP)).

Moreover, the invention provides a pharmaceutical composition comprising NK cells, CAR-NK cells or NKG2C+ NK cells, which were expanded according to the method as described herein, together with at least one pharmaceutically acceptable carrier or diluent.

In further aspects, the invention relates to NK cells, CAR-NK cells or NKG2C+ NK cells, which were expanded according to the method or the pharmaceutical composition as described herein for use in immunotherapy; the use of said NK cells, NKG2C+ NK cells or CAR-NK cells or said pharmaceutical composition for the preparation of a medicament for cancer immunotherapy and immunotherapy of viral infections; and a method of treatment comprising the administration of a therapeutically effective dose of said NK cells NKG2C+ NK cells or CAR-NK cells or said pharmaceutical composition to a subject in need thereof.

BRIEF DESCRIPTION OF DRAWINGS

The following figures are provided to illustrate various aspects of the invention. To that end, some of the figures contain schematic drawings and are not necessarily drawn to scale.

FIG. 3 shows HLA-B and -C haplotypes of selected donors for experiments depicted in FIGS. 1-9, the predicted ligands and analysis of potential mismatch to the feeder cells in GvH direction.

The c-myc-tagged NK cells were detected using an APC-coupled anti-c-myc antibody at indicated time points using flow cytometry. Isotype controls were included in the experiments.

Expansion rates were calculated by dividing the numbers of c-myc-positive cells to measured initial c-myc+cell numbers 2 days after transduction (day 2).

Figure 15:
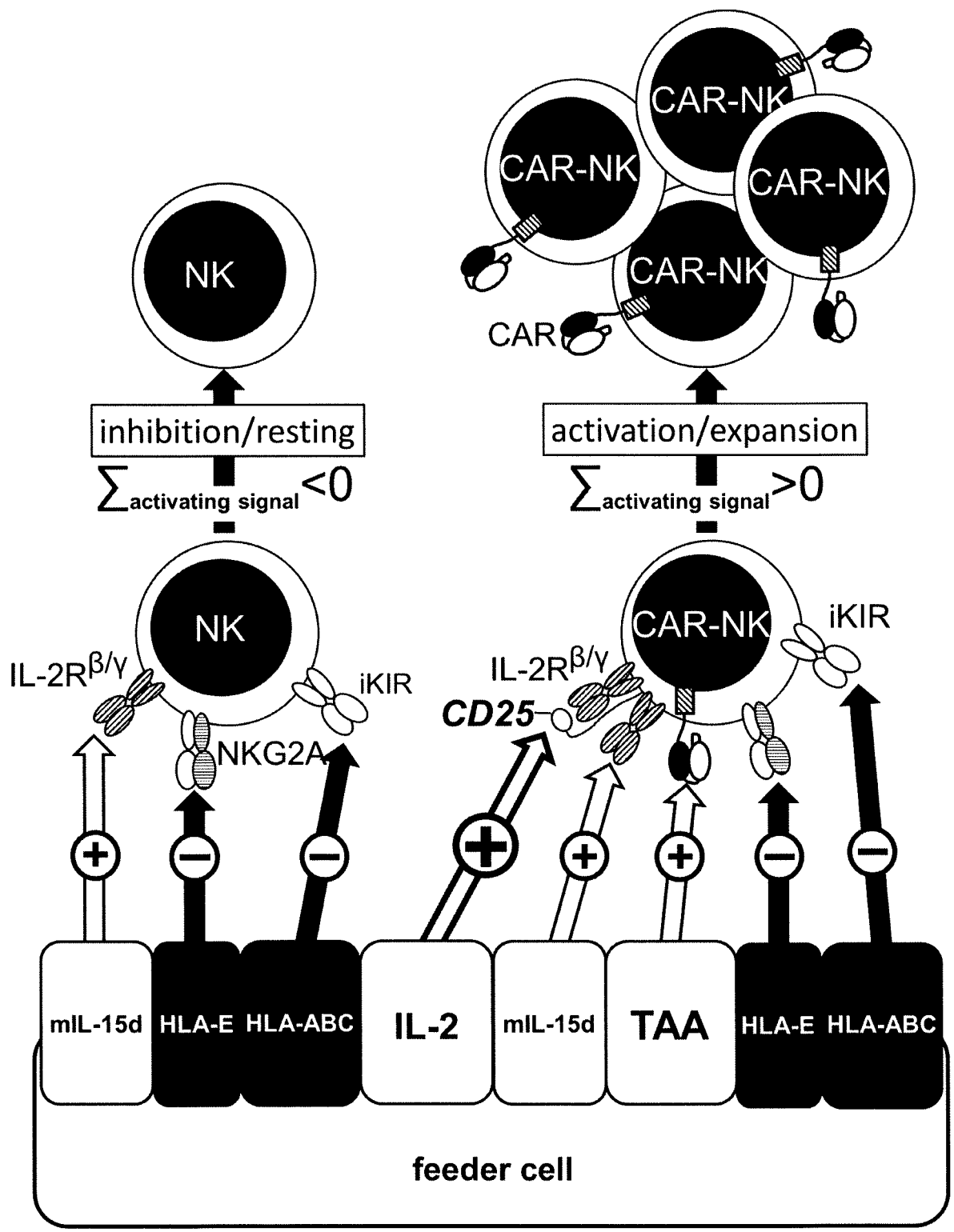

FIG. 15 shows the scheme for selective expansion of CAR-NK cells using feeder cells with transgenic expression of the cognate ligand TAA. Non-transduced CAR-negative cells are considered to receive strong inhibitory signals through NKG2A and KIRs which hold them in a resting state. Activation of NK cells through binding of the CAR to its cognate antigen on feeder cells is considered to induce CD25 expression leading to assembly of high affinity IL-2 receptor. Secreted IL-2 of feeder cells then enables the selective expansion of CAR+NK cells.

Figure 16:
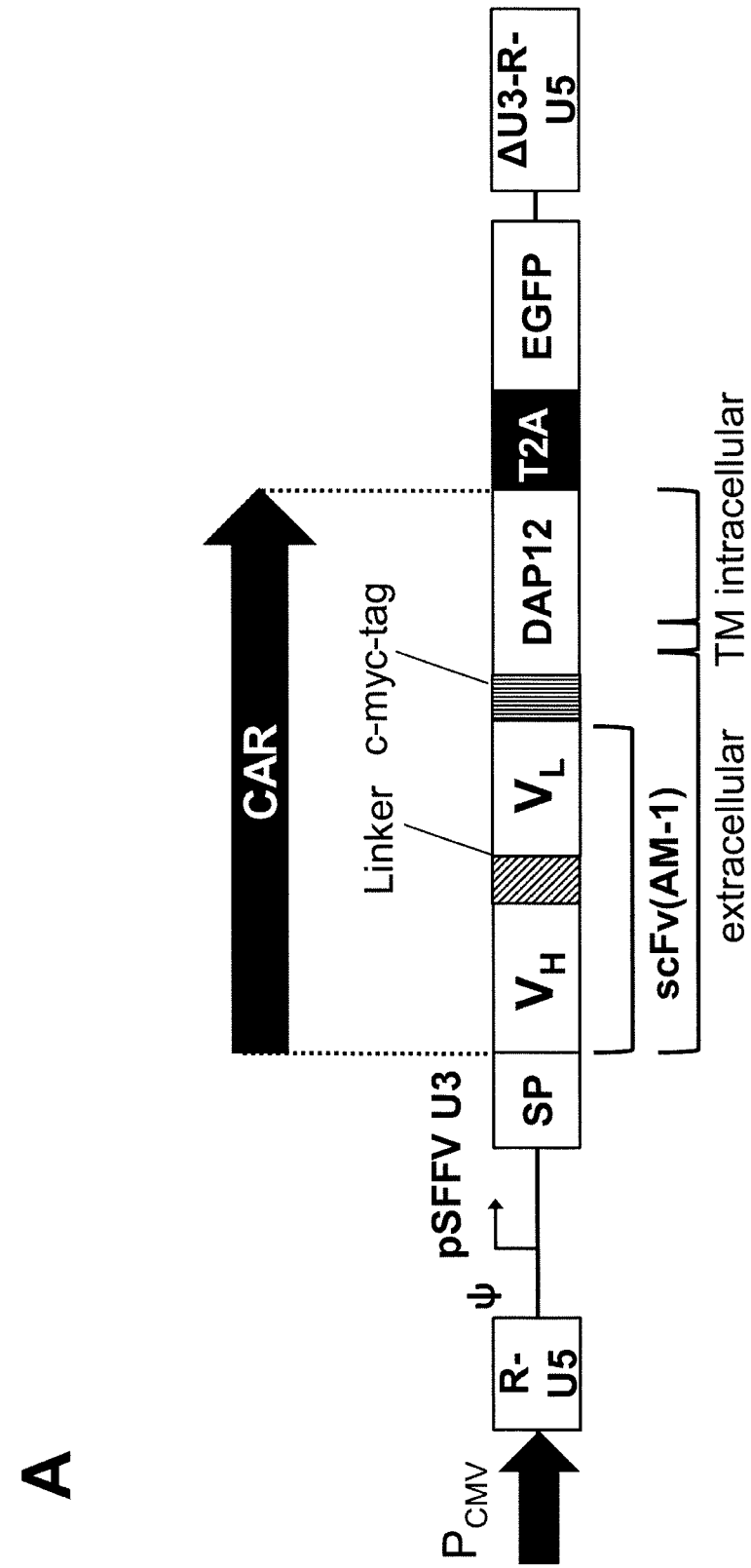
Figure 16:
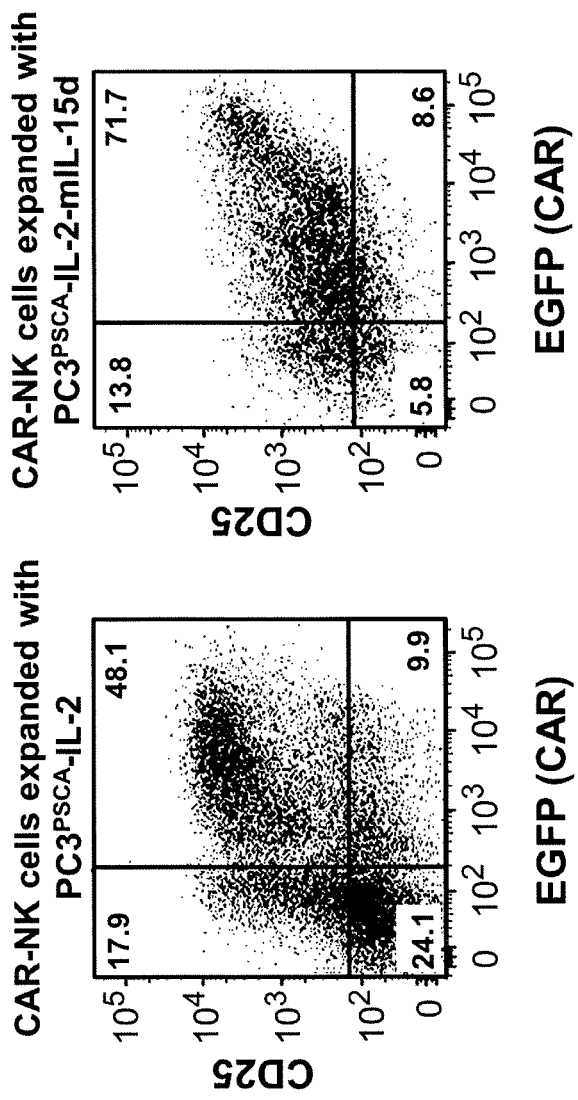
Figure 16:
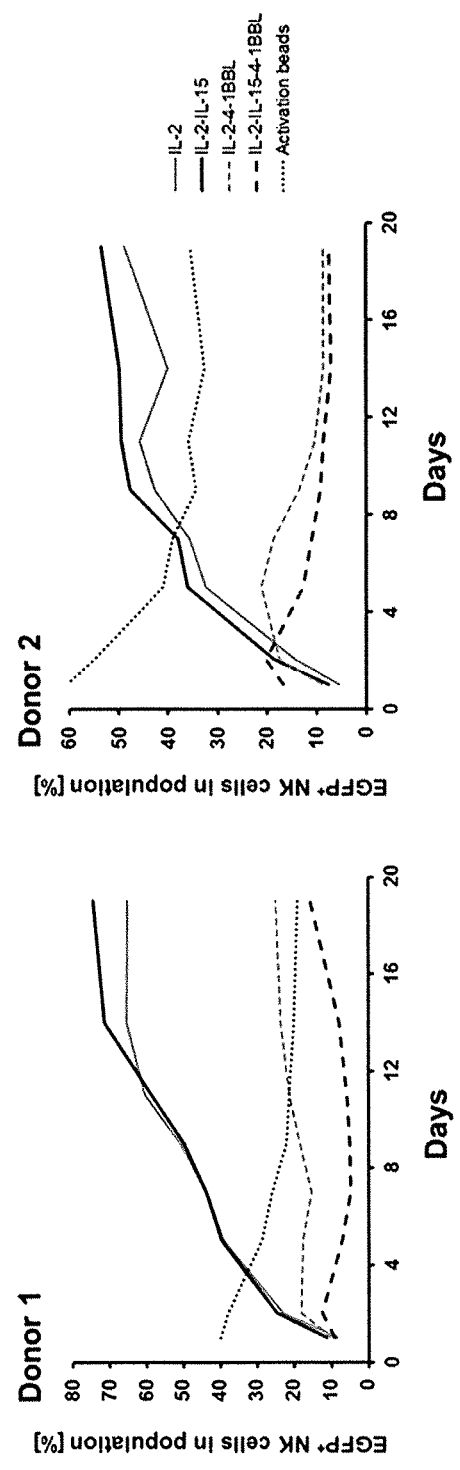
Figure 16:
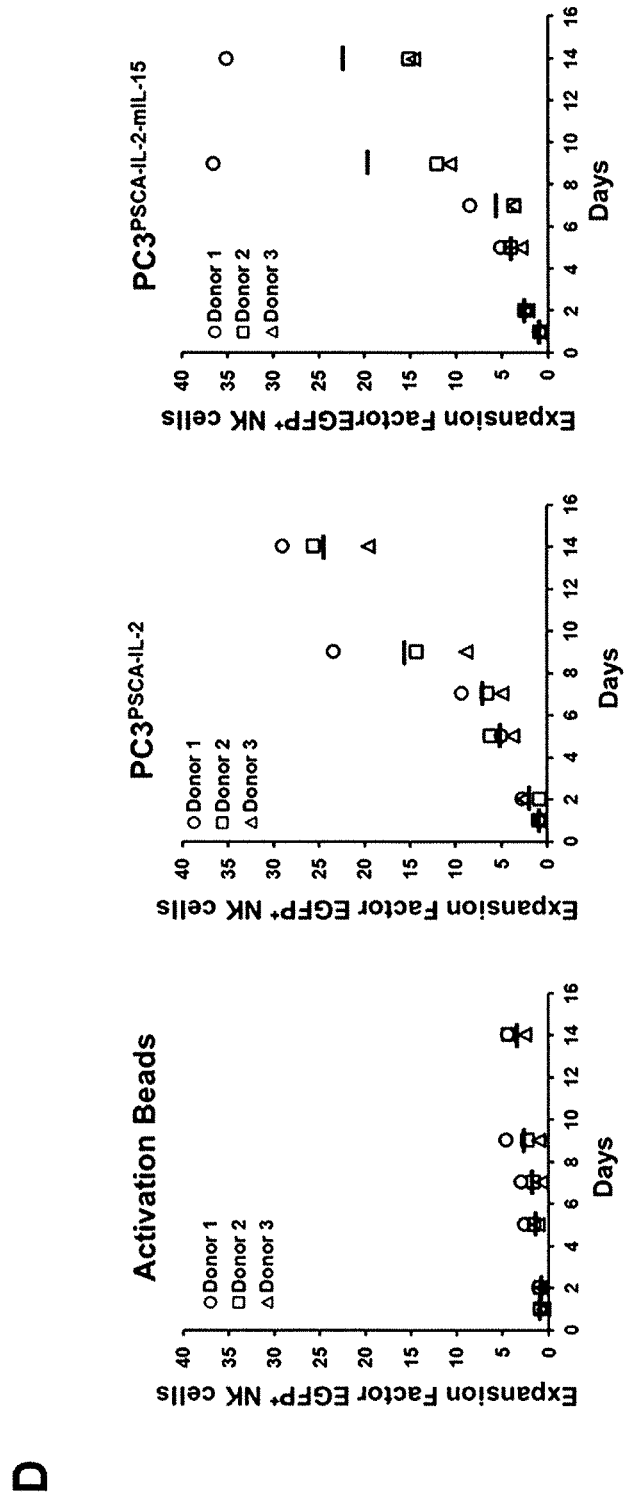

FIG. 16 (A) depicts the scheme for the lentiviral anti-PSCA-CAR construct (SEQ ID NO: 16). (B) shows selective upregulation of high affinity (CD25) IL-2 receptor on anti-PSCA-CAR-EGFP-NK cells and (C) outgrowth of anti-PSCA-CAR-EGFP-transduced NK cells from two donors using the $PC3^{PSCA}$ artificial feeder cell lines engineered with secreted IL-$^2$ and IL-2 plus membrane-bound mIL-15d, respectively. (D) shows representative expansion rates of anti-PSCA-CAR-EGFP-NK cells from three donors when using feeder cell lines in comparison to CD2/NKp46-bead-expanded anti-PSCA-CAR-EGFP-NK cells. Expansion rates were calculated by dividing the numbers of EGFP-positive cells to measured initial EGFP+cell numbers 1 day after transduction (day 1).

Figure 17:
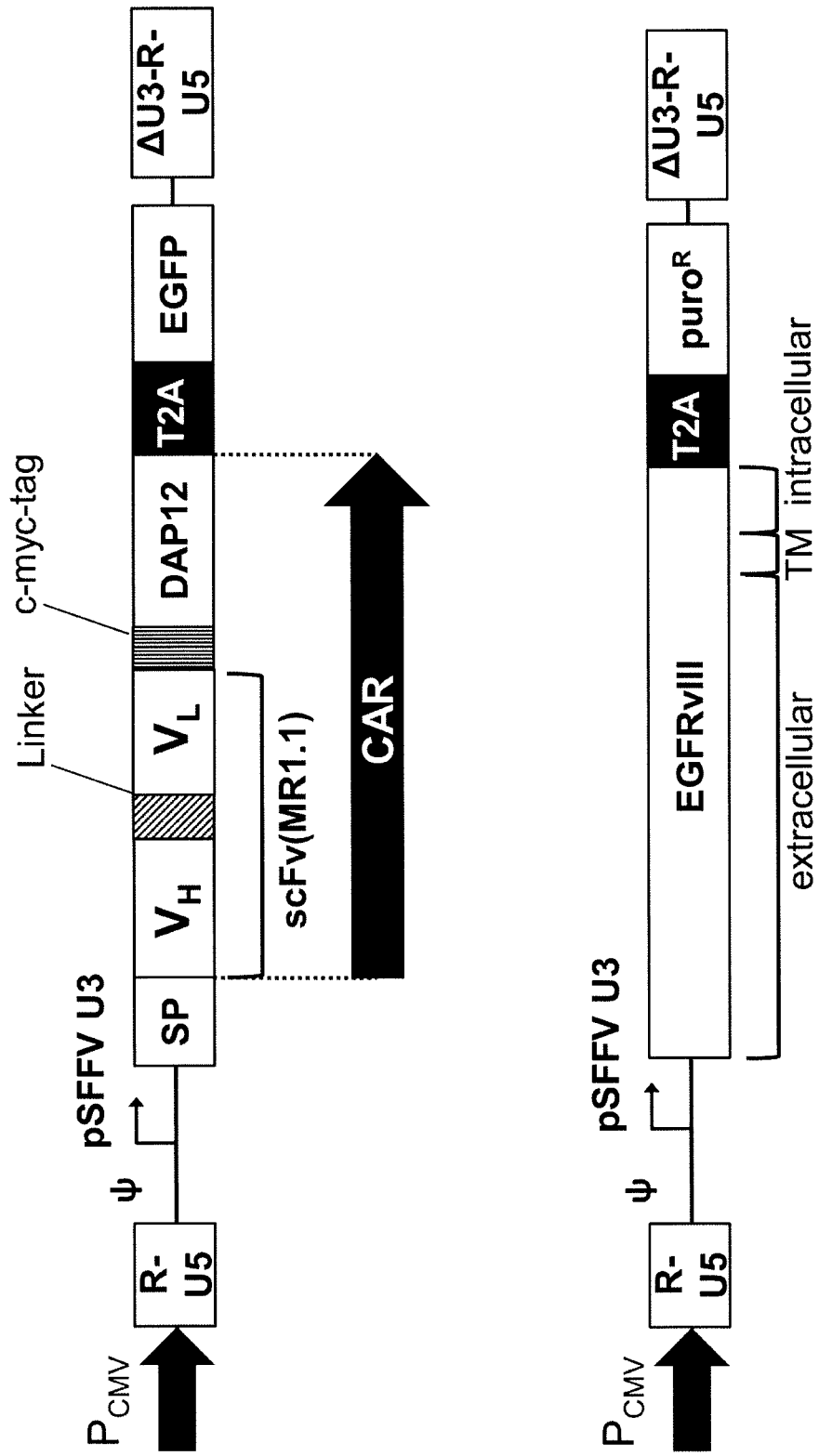
Figure 17:
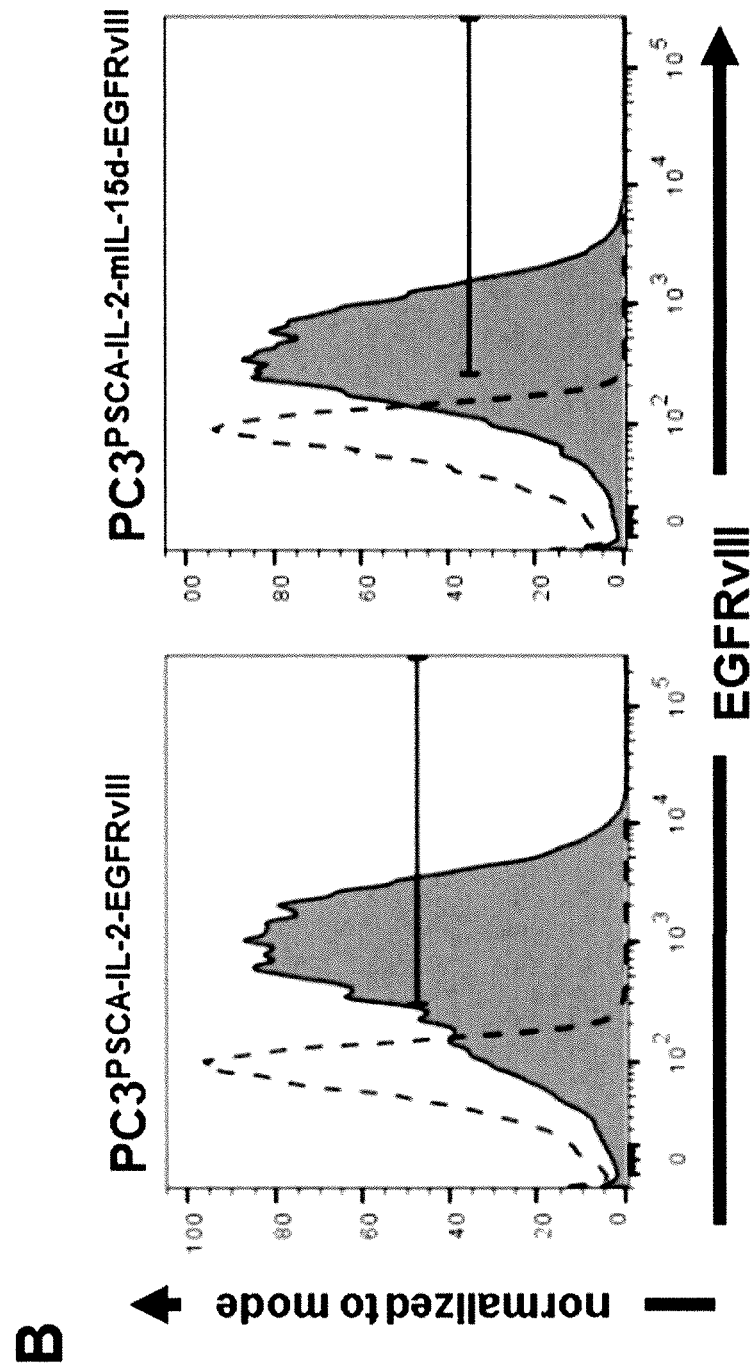
Figure 17:
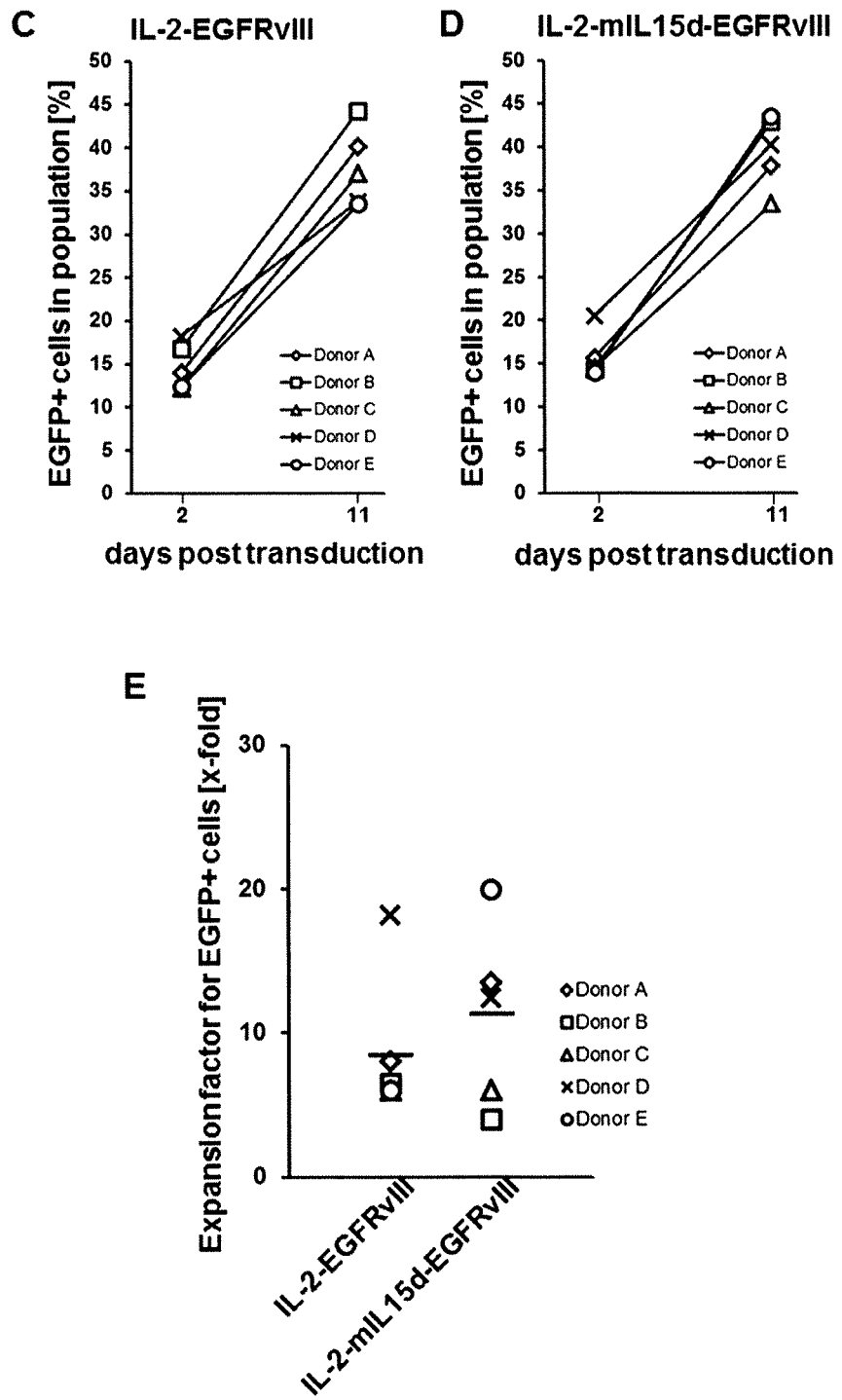

FIG. 17 (A) depicts the scheme for the anti-EGFRvIII-CAR ((SEQ ID NO: 17) for genetic modification of NK cells and lentiviral EGFRvIII construct (SEQ ID NO: 8) for genetic modification of feeder cells. (B) shows FACS-assisted analysis of EGFRvIII surface expression on feeder cells using biotinylated scFv(MR1.1)-BAP and secondary and biotin-APC-staining (filled histogram). Staining with only secondary anti-biotin-APC served as control (dotted line). (C) and (D) shows outgrowth of anti-EGFRvIII-CAR-transduced NK cells from five donors using the $PC3^{PSCA}$ artificial feeder cell lines genetically engineered with the cognate EGFRvIII antigen and with expression of secreted IL-2 and simultaneous expression of secreted IL-2 and mIL-15d, respectively. (E) shows expansion factors of anti-EGFRvIII-CAR-NK cells when cultured with indicated feeder cell lines for 9 days. CAR+NK cells were identified by expression of the co-transduced EGFP. Expansion rates were calculated by dividing the numbers of EGFP-positive cells at day 11 to measured initial EGFP+cell numbers at day 2 (2 days after transduction).

FIG. 18 shows the amino acid sequence of HLA-E-UL40-VMAPRTLIL (SEQ ID NO: 5)
  Underlined: signal sequence
  Bold, double underlined: VMAPRTLIL (SEQ ID NO: 3) nonamer peptide
  Dotted underlined: β2microglobulin sequence
  Italic: Linker
  Bold: HLA-E sequence FIG. 19 shows the amino acid sequence of HLA-E-UL40-VMAPRTLFL (SEQ ID NO: 6)
  Underlined: signal sequence
  Bold, double underlined: VMAPRTLFL (SEQ ID NO: 2) nonamer peptide
  Dotted underlined: β2microglobulin sequence
  Italic: Linker
  Bold: HLA-E sequence FIG. 20 shows the amino acid sequence of PSCA pre-proprotein (SEQ ID NO: 7)
  Underlined: Signal sequence
  Bold: PSCA proprotein FIG. 21 shows the amino acid sequence EGFRvIII (SEQ ID NO: 8)
  Underlined: signal sequence
  Bold: EGFRvIII
  Bold, double underlined: EGFRvIII neo-epitope FIG. 22 shows the amino acid sequence of human IL-2 (SEQ ID NO: 9), which contains the following components:
  Underlined: signal peptide
  Bold: mature IL-2 protein FIG. 23 shows the amino acid sequence of mIL-15d (SEQ ID NO: 10), which consists of the following components:
  Underlined: Signal sequence
  Dotted underlined: IL-15 sequence
  Double underlined: mutDAP12 sequence
  Double underlined, bold: site directed mutagenized Y to S
  Italic: Linker
  Italic, bold underlined: c-myc-tag FIG. 24 shows the amino acid sequence of 4-1BBL (CD137L) (SEQ ID NO: 11), which contains the following components:
  Underlined: transmembrane domain
  Bold: TNF domain
  Bold, double underlined: VSV-G tag FIG. 25 shows the amino acid sequence of scFv(9E10)-tm (SEQ ID NO: 12), which contains the following components:
  Underlined: influenca hemagglutinin signal peptide
  Bold: scF(9E10) $V_H$ and $V_L$ domains
  Italic: linker
  Italic, bold underlined: VSV-G tag and His6 tag
  doubled underlined: transmembrane domain and short cytoplasmatic region FIG. 26 shows the amino acid sequence of Homo sapiens DAP12 (SEQ ID NO: 13), which contains the following components:
  Underlined: Signal peptide
  Bold: mature DAP12
  Bold, italic underlined: transmembrane domain
  Bold, double underlined: ITAM FIG. 27 shows the amino acid sequence for the anti-EGFRvIII single chain fragment variable scFv(MR1.1) (SEQ ID NO: 14) which consist of the following components:
Underlined: Signal peptide
Bold: MR1.1 variable Ig domains
Bold, italic: linker FIG. 28 shows the amino acid sequence for the anti-PSCA single chain fragment variable scFv(AM1) (SEQ ID NO: 15) which consist of the following components
Underlined: Signal peptide
Bold: AM1 variable Ig domains
Bold, italic: linker FIG. 29 shows the amino acid sequence of anti-PSCA-CAR (scFv(AM1)-DAP12) (SEQ ID NO: 16), which consists of the following components:
Underlined: IgKappa signal peptide
Bold: variable Ig domains of scFv(AM1)
Bold, italic: glycin/serin linker of scFv
Bold, double underlined: c-myc-tag
Bold underlined: mature DAP12 sequence
Italic: linker sequences FIG. 30 shows the amino acid sequence of anti-EGFRvIII-CAR (scFv(MR1.1)-DAP12) (SEQ ID NO: 17), which consists of the following components:
Underlined: IgKappa signal peptide
Bold: variable Ig domains of scFv(MR1.1)
Bold, italic: glycin/serin linker of scFv
Bold double underlined: c-myc-tag
Bold underlined: mature DAP12 sequence
Italic: linker sequences FIG. 31 shows the amino acid sequence of DAP12-construct containing La- and c-myc-epitopes in its ectodomain (SEQ ID NO: 18), which consists of the following components:
Once underlined: DAP12 signal peptide
Bold, dotted underlined: la-epitope
Bold, double underlined: c-myc-epitope
Italic: linker
Bold: DAP12 sequence Definitions Preferably, the terms used herein are defined as described in "A multilingual glossary of 35 biotechnological terms: (IUPAC Recommendations)", H. G. W. Leuenberger, B. Nagel, and H.
Kölbl, Eds., (1995) Helvetica Chimica Acta, CH-4010 Basel, Switzerland.

The practice of the present invention will employ, unless otherwise indicated, conventional methods of biochemistry, cell biology, immunology, and recombinant DNA techniques which are explained in the literature in the field (cf., e.g., Molecular Cloning: A Laboratory Manual, 2$^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

As used herein, the expressions "cell", "cell line," and "cell culture" are used interchangeably and all such designations include progeny. Thus, the words "transformants" and "transformed cells" include the primary subject cell and culture derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, this will be clear from the context.

The terms "polypeptide", "peptide", and "protein", as used herein, are interchangeable and are defined to mean a biomolecule composed of amino acids linked by a peptide bond.

If peptide or amino acid sequences are mentioned herein, each amino acid residue is represented by a one-letter or a three-letter designation, corresponding to the trivial name of the amino acid, in accordance with the following conventional list: Amino Acid One-Letter Symbol Three-Letter Symbol

| Amino Acid | One-Letter Symbol | Three-Letter Symbol |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The terms "a", "an" and "the" as used herein are defined to mean "one or more" and include the plural unless the context is inappropriate.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human being sought by a researcher, veterinarian, medical doctor or other clinician, which includes alleviation of the symptoms of the disease or disorder being treated.

As used herein, the term "pharmaceutically acceptable" embraces both human and veterinary use: For example the term "pharmaceutically acceptable" embraces a veterinarily acceptable compound or a compound acceptable in human medicine and health care.

Conceptually there are three different types of tumor-associated antigens (TAAs): The first group are "neo-antigens" which originate from transforming viruses or are due to mutations or chromosomal aberrations in the tumor cells. Secondly "self-antigens", which are mainly proliferation and differentiation markers overexpressed in tumors or normal embryonic antigens aberrantly expressed in the course of epigenetic changes and cellular dedifferentiation of the tumor cells. Finally, the third group includes "modified self-antigens" representing self-antigens having different tumor-specific posttranslational modifications due to metabolic disturbances. Most TAAs of solid tumors correspond to self-antigens and modified self-antigens, which are re-expressed or overexpressed in tumors and are barely detected in normal tissues.

In the context of the present invention, the term "tumor antigen" or "tumor-associated antigen" ("TAA") relates to (i) proteins that upon mutational events in tumors contain neo-epitopes (neo-antigens), such as EGFR variant III (EGFRvIII [62]); (ii) "self-antigens", which are mainly proliferation and differentiation markers overexpressed in tumors or normal embryonic antigens aberrantly expressed in the course of epigenetic changes and cellular dedifferentiation of the tumor cells and (iii) "modified-self-antigens" representing proteins or glycolipids having different tumor-specific posttranslational modifications due to metabolic disturbances. Non-mutated, non-modified TAAs are under normal conditions specifically expressed in a limited number of tissues and/or organs or in specific developmental stages, for example, the tumor antigen may be under normal conditions specifically expressed in stomach tissue, preferably in the gastric mucosa, in reproductive organs, e.g., in testis, in trophoblastic tissue, e.g., in placenta, or in germ line cells, and are re-expressed or aberrantly expressed in one or more tumor or cancer tissues. In this context, "a limited number" preferably means not more than 3, more preferably not more than 2. The tumor antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor antigen is preferably associated with the cell surface of a cancer cell and is preferably not or only rarely expressed in normal tissues. Preferably, the tumor antigen or the aberrant expression of the tumor antigen identifies cancer cells. In the context of the present invention, the tumor antigen that is expressed by a cancer cell in a subject, e.g., a patient suffering from a cancer disease is preferably a self-protein in said subject. In preferred embodiments, the tumor antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system.

In the context of the invention the term viral antigen relates to viral proteins produced in infected host cells and are expressed as surface proteins or are viral peptides which are presented by infected cells in complex with HLA-E and 32-microglobulin. In some circumstances viral antigens represents TAAs, such as neo-antigens encoded by transforming oncogenic viruses (i.e. from human Papillomavirus causing cervix carcinoma and head and neck cancer; HCMV, involved in genesis of glioma, in Hepatitis B and -C virus causing liver cancer).

Examples for tumor-associated antigens and viral antigens that may be useful in the present invention are cell surface-localized proteins including, but not limited to, ART-4, CD4, CD19, CD20, CD30, CD33, CD44, cell surface proteins of the claudin family, such as CLAUDIN-6, CLAUDIN-18.2 and CLAUDIN-12, embryonic antigens such as CEA, members of the vascular endothelia growth factor family, epithelia cell adhesion molecule EpCAM, follicle stimulating hormon receptor, human high molecular weight-melanoma-associated antigen, folate binding protein FBP, folate receptor a, members of the epithelia glycoprotein family, diasialogangliosides, members of the carbonic anhydrase family, members of the carbohydrate antigen family, EGFR, EGFRvIII, G250, GnT-V, HER-2/neu, members of the mucin protein family such as MUC1, PSA, PSCA, PSMA, IL13Ra2, EphA2, and gp120 or gp41 from human immunodeficiency virus (HIV). Further examples of tumor antigens and viral antigens that may be useful in the present invention or can be identified by the present invention represent the VMAPRTLFL (SEQ ID NO: 2) peptide derived from HCMV Strain BE/1/2010 and HLA-G, VMAPRTLLL (SEQ ID NO: 1) from different HCMV strains [44] and HLA class I molecules A*01, A*03, A*11, A*29, A*30, A*31, A*32, A*33, A*36, A*74 and of Cw*15, VMAPRTLIL (SEQ ID NO: 3) from HCMV strain AD169 and HLA class I molecules HLA-Cw*01, -Cw*03, -Cw*04, -Cw*05, -Cw*06, -Cw*0801-03, -Cw*12, -Cw*14, -Cw*16, and -Cw*1702, and others such as HSP60 (VGGTSDVEVNEK (SEQ ID NO: 4)) which all can be presented by non-classical HLA-E molecules. Particularly preferred tumor antigens and viral peptides include PSCA (SEQ ID NO: 7), EGFRvIII (SEQ ID NO: 8), and through HLA-E-presented peptides VMAPRTLLL (SEQ ID NO: 1) VMAPRTLIL (SEQ ID NO: 3) and VMAPRTLFL (SEQ ID NO: 2).

The term "clonal expansion" or "expansion" refers to a process wherein a specific entity is multiplied. In the context of the present invention, the term is preferably used in the context of an immunological response in which lymphocytes are stimulated by an antigen, proliferate, and the specific lymphocyte recognizing said antigen is amplified. Preferably, clonal expansion leads to the production of high numbers of lymphocytes with high cytotoxicity towards tumor cells or virally infected cells. Specifically, in accordance with the invention, the term "clonal expansion" or "expansion" refers to a process wherein NK cells, more preferably a specific subset of NK cells are multiplied.

A single-chain fragment variable (scFv) is not actually a fragment of an antibody, but instead is a fusion protein of the variable regions of the heavy ($V_H$) and light chains ($V_L$) of immunoglobulins, connected with a short linker peptide of ten to about 25 amino acids. The linker is usually rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. Divalent (or bivalent) single-chain variable fragments (di-scFvs, bi-scFvs) can be engineered by linking two scFvs. This can be done by producing a single peptide chain with two $V_H$ and two $V_L$ regions, yielding tandem scFvs. For a review of scFv see Plückthun in The Pharmacology of Monoclonal Antibodies, vol. 113, Rosenburg and Moore eds., Springer-Verlag, New York, pp. 269-315 (1994).

In the context of the innovation, the term chimeric antigen receptor (CAR) is either used for conventional CARs which are composed of a binding moiety (e.g. single chain fragment variable (scFv), or ligands for the respective receptor on target cells) for a certain human cells surface protein, sugar structure or protein complex and a transmembrane domain followed by a signaling adapter domain. The term CAR is also used for alternative concepts in the context of the innovation, in particular for the recently described Uni-CAR-system [63, 64] or for epitope-tagged signaling adapters of NK cells in conjunction with targeting modules, such a bispecific antibody molecules, for redirection of NK cells to tumor cells and virus-infected cells, respectively (reverse CAR approach, revCAR). The terms CAR, UniCAR and reverse CAR as used herein are interchangeable and are defined to mean an artificial biomolecule used to redirect lymphocytes against target cells.

Co-stimulatory molecules(s) according to the invention are selected from cytokines such as IL-15, IL-18, IL-21; which have already been described to promote NK-cell expansion.

Activating surface molecule(s) according to the invention are selected from known co-stimulatory NK cell ligands such as 4-1BBL, OX40L, B7-H6, CD58, CD112/Nectin-1, CD155/Necl-5, MIC-A/B, ULBP1-6, C-type lectin-like glycoproteins belonging to the CLEC2 subfamily (i.e., LLT1, AICL, and KACL); signaling lymphocytic activating molecules (SLAMs, such as CD150, CD244, and CD48) and viral derived molecules such as viral hemagglutinin, which have already been described to activate and promote NK-cell expansion.

According to the invention another group of activating surface molecules represents ligands/tumor associated antigens or antibodies binding to activating NK cell receptors such as NKG2C and CARs on NK cells, respectively.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases.

Preferably, a "cancer disease" is characterized by cells expressing a tumor antigen and a cancer cell expresses a tumor antigen.

In one embodiment, a cancer disease is a malignant disease which is characterized by the properties of anaplasia, invasiveness, and metastasis. A malignant tumor may be contrasted with a non-cancerous benign tumor in that a malignancy is not self-limited in its growth, is capable of invading into adjacent tissues, and may be capable of spreading to distant tissues (metastasizing), while a benign tumor has none of those properties.

DETAILED DESCRIPTION OF THE INVENTION

Donor-derived allogeneic NK cells as well as autologous NK cells have great potential to treat viral infections and so far incurable diseases, like primary tumors or metastatic cancers.

Nowadays, several genetically modified artificial feeder cell lines enable a strong ex vivo expansion of NK cells from healthy donors as well as patients potentially leading to a hyper-activated NK cell product. The application of hyper-activated NK cells bears the risk of unwanted GvHD effects. Furthermore, current expansion protocols include constitutive addition of human interleukin, in particular rhIL-2 for effective expansion. A feeder cell line releasing physiological amounts of IL-2 and being able in mimicking an autologous KIR/KIR-Ligand (HLA) setting and therefore allowing the fully autonomous proliferation of non-hyper-activated NK cells would be advantageous and saves costs and working time.

Accordingly, the present invention provides artificial feeder cell lines for selective expansion of NK cells and NK cell subsets, such as NKG2C+NK cells from HCMV-seropositive donors lacking pre-existing expansion of NKG2C cells in peripheral blood, as well as for selective expansion of CAR-modified NK cells. However, protocols for selective expansion of NKG2C+ and of CAR-NK cells to high cell numbers for pre-clinical and clinical use are missing in the prior art.

In order to overcome this gap in the prior art, the present invention provides a method for specifically inducing proliferation and expansion of human NK cells with artificial feeder cells, said method comprising contacting said NK cells with artificial feeder cells, wherein said artificial feeder cells are genetically engineered and comprise an expression vector, which expresses at least one cytokine and additionally co-stimulatory molecules(s) or activating surface molecule(s).

In a preferred embodiment, the invention provides a method for specifically inducing proliferation and expansion of human NK cells with artificial feeder cells, said method comprising (a) contacting said NK cells with artificial feeder cells, wherein said artificial feeder cells
express at least one inhibitory NK cell ligand selected from HLA C1, C2, and Bw4 type for killer cell immunoglobulin-like receptors (KIRs), non-KIR binding Bw6 ligand and endogenous HLA-E-ligand for inhibitory NKG2A receptor, and
at least one cytokine, such as interleukin-2; and
optionally are genetically engineered and comprises at least one expression vector which expresses additionally at least one co-stimulatory molecule selected from cytokines such as IL-15, IL-18, IL-21; and/or at least one activating surface molecule selected from 4-1BBL, OX40L, B7-H6, CD58, CD112/Nectin-1, CD155/Necl-5, MIC-A/B, ULBP1-6, C-type lectin-like glycoproteins belonging to the CLEC2 subfamily (i.e., LLT1, AICL, and KACL); signaling lymphocytic activating molecules (SLAMs, such as CD150, CD244, and CD48) and viral derived molecules such as viral hemagglutinin;

(b) cultivating said NK cells and artificial feeder cells under conditions allowing the expansion of said NK cells.

In a further embodiment of the invention, the artificial feeder cells express more than one, e.g. 2, 3, 4 or more inhibitory NK cell ligand(s) selected from HLA C1, C2, and Bw4 type for killer cell immunoglobulin-like receptors (KIRs), non-KIR binding Bw6 ligand and HLA-E-ligand for inhibitory NKG2A receptor and therefore matches selected donor NK cells expressing the cognate KIR(s).

In a preferred embodiment, the artificial feeder cells express all of the inhibitory NK cell ligand(s) of the group consisting of Bw4-, C1- and C2-ligands for NK cells and non-KIR binding Bw6 ligand and HLA-E, and therefore are matched to any NK cell from different donors.

In one embodiment, the artificial feeder cells are isolated cells and naturally express at least one, preferably 2, 3, 4 or more of the inhibitory NK cell ligand(s) selected from HLA C1, C2, and Bw4 type for killer cell immunoglobulin-like receptors (KIRs), non-KIR binding Bw6 ligand and endogenous HLA-E-ligand for inhibitory NKG2A receptor.

In another embodiment of the invention, the artificial feeder cells are genetically engineered cells comprising at least one expression vector, which recombinantly expresses at least one, preferably 2, 3, 4 or more, most preferably all of the inhibitory NK cell ligand(s) selected from HLA C1, C2, and Bw4 type for killer cell immunoglobulin-like receptors (KIRs), non-KIR binding Bw6 ligand and endogenous HLA-E-ligand for inhibitory NKG2A receptor.

In another embodiment of the invention, the artificial feeder cells are genetically engineered cells comprising at least one expression vector, which recombinantly expresses one or some, e.g. 2, 3 or 4 of the inhibitory NK cell ligand(s) selected from HLA C1, C2, and Bw4 type for killer cell immunoglobulin-like receptors (KIRs), non-KIR binding Bw6 ligand and endogenous HLA-E-ligand for inhibitory NKG2A receptor, wherein one or some, e.g. 2, 3 or 4 of said inhibitory NK cell ligand(s) that are not expressed recombinantly, are naturally expressed by the artificial feeder cells.

Most preferably, the artificial feeder cells express HLA-E-ligand for inhibitory NKG2A receptor of NK cells and simultaneously express at least one inhibitory ligand for killer cell immunoglobulin-like receptors (KIRs) selected from C1 or C2 ligand and at least one ligand selected from Bw4 or Bw6 of NK cells, resulting in a KIR-ligand:KIR match to individual donor NK cells chosen for expansion.

In one embodiment of the invention, the at least one cytokine, such as interleukin-2, is naturally expressed by the artificial feeder cells.

In another embodiment, the artificial feeder cells are genetically engineered and comprise an expression vector which expresses the at least one cytokine, such as interleukin-2, recombinantly.

In a preferred embodiment of the invention, the artificial feeder cells are genetically engineered and express additionally one co-stimulatory molecule selected from cytokines such as IL-15, IL-18, IL-21; and/or one activating surface molecule selected from 4-1BBL, OX40L, B7-H6, CD58, CD112/Nectin-1, CD155/Necl-5, MIC-A/B, ULBP1-6, C-type lectin-like glycoproteins belonging to the CLEC2 subfamily (i.e., LLT1, AICL, and KACL); signaling lymphocytic activating molecules (SLAMs, such as CD150, CD244, and CD48) and viral derived molecules such as viral hemagglutinin.

In a further embodiment of the invention, the artificial feeder cells are genetically engineered and express additionally 2, 3 or more co-stimulatory molecule selected from cytokines such as IL-15, IL-18, IL-21; and/or 2, 3, 4, 5 or more activating surface molecule selected from 4-1BBL, OX40L, B7-H6, CD58, CD112/Nectin-1, CD155/Necl-5, MIC-A/B, ULBP1-6, C-type lectin-like glycoproteins belonging to the CLEC2 subfamily (i.e., LLT1, AICL, and KACL); signaling lymphocytic activating molecules (SLAMs, such as CD150, CD244, and CD48) and viral derived molecules such as viral hemagglutinin.

In order to express the aforementioned molecules, the artificial feeder cells may comprise 1, 2, 3, 4, 5 or more expression vectors, preferably 1, 2 or 3, most preferably 1 or 2 expression vectors, which contain a nucleic acid molecule for the expression of the aforementioned molecules.

The artificial feeder cell lines and the method of the invention are advantageous. Said method and especially said artificial feeder cells of the invention, which are further genetically engineered to secrete at least one cytokine, have the advantage that they allow the selective activation and expansion of human primary NK cells without the need of any exogenously added cytokine.

In one embodiment, lentiviral gene transfer may be applied for stable expression of cytokines and co-stimulatory molecules as well as of activating surface molecules in feeder cells and of CARs in NK cells by first constructing a lentiviral vector encoding the coding sequences of the respective genes or genetic elements. An exemplary lentiviral vector includes, but is not limited to, the vector pHATtrick and its derivatives, in which the lentiviral parts of the vector are derived from the human immunodeficiency virus (HIV) [65].

Lentiviral particles are typically produced by transient transfection of Human Embryonal Kidney (HEK) 293T (ACC 635) cells with the lentiviral vector encoding the gene or nucleic acid to be delivered and co-transfection with a helper plasmid encoding structural viral proteins and other viral proteins such as reverse transcriptase, integrase, protease (e.g. pCD/NL-BH [65], psPAX2, addgene plasmid 12260) plus a plasmid encoding for an envelope glycoprotein (e.g. pcz-VSV-G [65], pMD2.G, addgene plasmid #12259). Various envelopes from different virus species can be utilized for this purpose. Lentiviral vectors can successfully pseudotype, but are not limited to, with the envelope glycoproteins (Env) of amphotropic murine leukemia virus (MLV) or the G protein of vesicular stomatitis virus (VSV-G), with RD114 glycoprotein from endogenous feline virus, with a modified envelope of the prototypic foamy virus (PFV) or chimeric envelope glycoprotein variants derived from gibbon ape leukemia virus (GaLV) and MLV. Supernatants from transfected HEK293T cells can be harvested 24 h to 96 h after transfection and virus particles may, but not necessarily have to, be concentrated from the supernatant by ultracentrifugation or other methods.

In the context of the present invention, NK cells used in the methods of the present invention may be autologous, syngeneic or allogeneic, with the selection dependent on the disease to be treated and the means available to do so. NK cells can be isolated from peripheral blood, cord blood and any other source, including from a tumor explant of the subject being treated.

CAR-NK cells in the methods of the present invention compromise primary autologous, syngeneic or allogeneic NK cells, which are genetically engineered to express a chimeric antigen receptor (CAR) on the cell surface. For the purpose of the invention various signaling adaptor domains from cytoplasmic regions of CD28, CD137 (4-1BB), CD134 (OX40), DAP10, CD3zeta, CD3epsilonR1 and DAP12 can be used. For the described method, CARs comprising an extracellular proportion containing a c-myc-tag fused to the transmembrane and cytoplasmic domain of the DNAX activation protein 12 (DAP12) [65, 66] (SEQ ID NO: 13, 16, 17 and 18) are used.

In a preferred embodiment of the method of the invention, the artificial feeder cells express inhibitory NKG2A ligand (i.e. HLA-E loaded with endogenous HLA class I leader peptides) and human leukocyte antigen (HLA) Cl-, C2-, and Bw4 ligands for killer cell immunoglobulin-like receptors (KIRs) and non-KIR binding Bw6 ligands. The C1, C2 and Bw4 epitopes act as ligands for natural killer cell KIRs. The HLA-Bw6 variant has no known KIR ligand. In a most preferred embodiment, said artificial feeder cells simultaneously express NGK2A ligand, Bw4-, Cl- and C2-KIR ligands for NK cells and non-KIR binding Bw6 ligands. Said feeder cells match C1, C2, Bw4 haplotypes of NK cell donors and therefore mimics an autologous KIR/KIR-ligand setting, i.e. said feeder cells are KIR-ligand/inhibitory KIR-matched to any NK cell from different donors.

In a further preferred embodiment of the methods of the invention, the at least one cytokine, which is expressed by the artificial feeder cells of the invention, is human interleukin 2 (IL-2), more preferably human IL-2 which is secreted. IL-2 is a cytokine signaling molecule in the immune system. It is a cytokine that regulates the activities of white blood cells (leukocytes, often lymphocytes) that are responsible for immunity. IL-2 mediates its effects by binding to IL-2 receptors, which are expressed by lymphocytes. In the methods of the invention, the human IL-2, which is secreted by the artificial feeder cells, promotes the expansion of the NK cells, preferably of the CAR-NK cells or NKG2C+NK cell fractions according to the invention.

In a more preferred embodiment of the invention, said IL-2 is human IL-2 containing the natural signal peptide. In a most preferred embodiment of the invention, said IL-2 has an amino acid sequence of SEQ ID NO: 9.

Preferably, said artificial feeder cells are genetically engineered and secrete human interleukin 2 (IL-2) and express 4-1BBL simultaneously.

Further preferably, said artificial feeder cells are genetically engineered and secrete IL-2 and simultaneously express 4-1BBL (SEQ ID NO: 11) and membrane-anchored human IL-15-DAP12mut-ITAM (mIL-15d) (SEQ ID NO: 10).

Further preferably, said artificial feeder cells are genetically engineered and secrete IL-2 or secrete IL-2 and simultaneously express mIL-15d.

In a most preferred embodiment of the methods of the invention, the artificial feeder cells is genetically engineered to stably express the TAA "Prostate Stem Cell Antigen" (PSCA) (SEQ ID NO: 7) as surface marker, and are genetically engineered to express either a secreted form of IL-2 simultaneously with 4-1BBL or a secreted form of IL-2 simultaneously with 4-1 BBL and membrane-anchored human IL-15-DAP12mut-ITAM (mIL-15d) (SEQ ID NO: 10).

In another most preferred embodiment of the methods of the invention such genetically engineered artificial feeder cell line induces the expansion of donor NK cells and preserves tolerance of expanded NK cells against autologous normal cells. Said NK cells are competent in eliciting ADCC against KIR/KIR-ligand matched target cells.

PSCA represents a GPI-anchored cell surface tumor antigen which for instance is detected in normal prostate-specific tissue and is overexpressed in prostate cancer specimens including both, high-grade prostatic intraepithelial neoplasia and androgen-dependent/-independent tumors. In a further aspect of the invention the surface marker PSCA can be used to identify feeder cell contaminations in the expanded NK cells or as tumor antigen (see below). 4-1BBL is a ligand that binds to 4-1EE, a type 2 transmembrane glycoprotein receptor belonging to the TNF superfamily, and was originally detected on activated T Lymphocytes. 4-1 BB is an inducible costimulatory receptor and represents a promising receptor for increasing antitumor activity and persistence of T- and NK cells in cancer therapy. IL-15-DAP12mut-ITAM (mIL-15d) contains a glycin-serin linker between human IL-15 and human DAP12, and a mutated (inactivated) ITAM. Most preferably, said IL-15-DAP12mut-ITAM (mIL-15d) is encoded by a nucleic acid of SEQ ID NO: 10.

In a more preferred embodiment of the invention, said 4-1BBL is human 4-1 BBL. In a most preferred embodiment of the invention, said 4-1 BBL has the amino acid sequence of SEQ ID NO: 11.

Interleukin-15 (IL-15), a member of the 4-alpha-helix bundle family of cytokines, has emerged as a candidate immunomodulator for the treatment of cancer. IL-15 acts through its specific receptor, IL-15Ra, which is expressed on antigen-presenting dendritic cells, monocytes and macrophages. IL-15 exhibits broad activity and induces the differentiation and proliferation of T, B and natural killer (NK) cells by juxtacrine binding to low affinity IL-2/IL15 receptor containing p- and y-chains of IL-2R. It also enhances cytolytic activity of CD8+ T cells and induces long-lasting antigen-experienced CD8+CD44$^{hi}$ memory T cells.

DAP12 is a 12 kDa transmembrane protein recently recognized as a key signal transduction receptor element in Natural Killer (NK) cells. It is a disulfide-linked homodimer that non-covalently associates with several activating receptors expressed on NK cells. Activation signals initiated through DAP12 are predicted to play strategic roles in triggering NK cell cytotoxicity responses toward certain tumor cells and virally infected cells. The cytoplasmic domain of DAP12 contains an Immunoreceptor Tyrosine-based Activation Motif (ITAM).

Phosphorylation of ITAM tyrosines mediates associations with protein tyrosine kinases, which is a resonant feature of signaling through these motifs in RAG-recombined immunoreceptors of T and B cells as well as NK cell receptors. In addition, its expression in other tissues, including dendritic cells and monocytes, suggests that DAP12 transduces ITAM-mediated activation signals for an extended array of receptors in those cells as well. In a preferred embodiment, the IL-15-DAP12mut-ITAM expressed by the artificial feeder cells contains a mutated (inactivated) ITAM (mIL-15d) (SEQ ID NO: 10). The site directed mutagenesis T91S and T102S of DAP12 results in a signaling defective mIL-15d dimer with increased half-life time and decreased internalization after crosslinking on feeder cells thereby enhancing juxtacrine stimulation of cognate low affinity IL-2/IL-15-receptor expressed on NK cells.

In a more preferred embodiment, the invention provides a method comprising the specific and/or selective induction of the proliferation and expansion of a NK cell subset expressing an activating NK cell receptor chosen from Natural Cytotoxcity Receptors (NCRs), small-tailed KIRs or NKG-receptors, comprising contacting a NK bulk cell population containing the NK subpopulation of interest with artificial feeder cells which are genetically engineered and comprise an expression vector which expresses the cognate NK cell ligand for the activating NK cell receptor. Alternatively, the artificial feeder cell line is loaded with activating peptides on HLA-E molecules specific for activating NKG cell receptors of the NK subpopulation of interest, such as for an activating receptor of the CD94/NKG2 family of the NK subpopulation of interest; or the artificial feeder cell line is engineered and expresses a membrane-bound antibody specific for the activating NK cell receptor of the NK subpopulation of interest. The advantage of this method is that NK cell subsets can be expanded in a target and purpose specific manner, which are e.g. suitable for use in personalized medicine.

In particular, NK cell subsets with expression of the activating NKG2C+cell receptor can be selectively expanded using artificial feeder cells genetically engineered to express either the secreted form of IL-2 or the secreted form of IL-2 plus mIL-15d and additionally genetically modified with an artificial ligand for said activating NK cell receptor or loaded with activating peptides on HLA-E for said activating NKG2C receptor. Therefore, said feeder cells provide only suboptimal activation to NK cells but activates and expands those NK cells subsets containing the NKG2C receptor. Exemplary for the described method is example 6 showing selective expansion of NKG2C+NK cell subsets using feeder cells genetically engineered to express either the secreted form of IL-2 or the secreted form of IL-2 plus mIL-15d and subsequently modified by exogenous loading of an activating VMAPRTLFL (SEQ ID NO: 2) -HLA-G leader peptide/UL40 signal peptide from HCMV strain BE/1/2010 and an activating VMAPRTLLL (SEQ ID NO: 1) HLA class I leader peptides/UL40 signal peptide from HCMV on HLA-E, respectively, or genetically engineered to express an artificial β2-microglobulin-HLA-E-protein (designated HLA-E-UL40sp) fused to VMAPRTLIL (SEQ ID NO: 5) and VMAPRTLFL (SEQ ID NO: 6), respectively, for selective activation and expansion of NK cells with expression of the cognate NKG2C-receptor (NKG2C+NK cells).

NKG2C+NK cells are highly potent against tumor cells and viral infections, such as HCMV infections, and are considered to be capable of developing a memory for target cells. Moreover and in contrast to NKG2A NK cells, NKG2C+NK cells are capable of recognizing viral peptides. Therefore, NKG2C+NK cells represent a desired NK cell population for cancer and antiviral therapy, especially, because in the case of HCMV and other virus infections, latent viruses are present in an affected subject. However, NKG2C+NK cells are under-represented in the population of total NK cells in vivo, wherein NKG2A NK cells are over-represented. With the method of the invention, NKG2A NK cells are repressed and the desired NKG2C+NK cells are enriched. The method of the invention thus fulfils a so far unmet need in selectively expanding and providing NKG2C+NK cells for the treatment of cancer and viral infections.

In a most preferred embodiment, the invention provides a method for specifically inducing proliferation, i.e. specifically expanding of genetically engineered NK cells displaying an artificial chimeric antigen receptor (CAR), comprising contacting a NK cell population containing CAR-NK cells with artificial feeder cells that endogenously express the cognate surface antigen (i.e. TAA) for the CAR or are genetically engineered and comprise an expression vector which expresses the cognate surface antigen for the CAR or are genetically engineered and comprise an expression vector which expresses an membrane-bound antibody specific for an epitope-tag implemented in the CAR. Suitable epitope tags of CARs include biotinylated biotin acceptor peptides (BAPs), FLAG-epitope, VSG-G-epitope, La-epitope, influenza hemagglutin (HA)-epitope and preferably c-myc-epitope. Said artificial feeder cell lines, are genetically engineered to express either the secreted form of IL-2 or the secreted form of IL-2 plus mIL-15d. Said feeder cells provides only suboptimal activation to NK cells but activates and leads to expansion of those NK cells subsets containing the CAR and the epitope-tagged CAR, respectively. Exemplary for the described method is example 8 showing selective expansion of NK cells genetically engineered with a DAP12-based revCAR construct which contains a c-myc epitope. Exemplary conventional CARs for the method include CARs described in example 9 containing a c-myc-tag in their ectodomain. In a further embodiment of the invention described in example 9 the epitope-tag of the CAR can be detected by using a specific monoclonal antibody and subsequently staining with a fluorochrome-conjugated anti-species secondary antibody. The epitope tag can additionally be used to purify CAR-NK cells using methods as for example FACS-assisted cell sorting or magnet activated cell sorting. Furthermore, the epitope tags provided in the CAR can be used for therapeutic bi-specific antibodies, where the bispecific antibodies crosslink the CAR and a target molecule on the surface of tumor or virally infected cells.

The invention also relates to engineered NK cells. In a preferred embodiment of the invention, the NK cells are engineered and comprise a nucleic acid encoding the CAR or reverse CAR, wherein said nucleic acid encodes a polypeptide of the activating transgenic surface receptor on NK cells, which comprises a signal transduction domain selected from cytoplasmic regions of CD28, CD137 (4-1BB), CD134 (OX40), DAP10, CD3zeta, CD3epsilonRl and DAP12 signaling adaptor, preferably from DAP12 signaling adaptor of SEQ ID NO: 13.

In a preferred embodiment of the invention, the NK cells of the invention comprise conventional chimeric antigen receptors (CARs). The CARs suitably comprise a ligand or antibody-derived recognition domain for binding to surface structures on target cells. Thus, in a preferred embodiment of the invention, the NK cells comprise a nucleic acid, which encodes a CAR comprising a single chain fragment variable (scFv) implemented in said CAR. More preferably, said scFv is the scFv of SEQ ID NO: 14, specifically recognizing EGFRvIII, and/or the scFv of SEQ ID NO: 15, specifically recognizing PSCA. In a further preferred embodiment, the NK cells comprise a nucleic acid encoding an artificial activating transgenic surface receptor on NK cells, such as a CAR or reverse CAR, which comprises an epitope-tag, such as FLAG-epitope, VSG-G-epitope, La-epitope, influenza hemagglutin (HA)-epitope) and/or a c-myc-epitope, most preferably the peptide EQKLISEEDL SEQ ID NO: 19) a well-known c-myc epitope fused to DAP12 according to SEQ ID NO: 18.

Generally, a genetically engineered NK cells comprising a single chain fragment variable (scFv) implemented in the CAR can be produced by screening a subject for an antigen, isolating the antigen, producing monoclonal antibodies against the antigen, sequencing the monoclonal antibody, generating an scFv against the antigen, determining the nucleic acid sequence coding for the scFv, cloning said nucleic acid, which encodes the scFv, into an NK cell line and expressing the scFv.

The artificial feeder cells used in the methods of the invention are preferably eukaryotic cells, more preferably human cell lines expressing HLA class I molecules and HLA-E, most preferably the prostate cancer cell line PC3 or derivatives thereof. PC3 is a human prostate cancer cell line which growth as adherent monolayer with strong expression of HLA-class 1 molecules and HLA-E. The PC3 cell line contains known C1 and C2 ligands for the dominant KIR2DL1 and KIR2DL2/3 as well as weaker Bw4 ligand for KIR3DL1. In case of an unwanted transfer of PC3-derived feeder cells during adoptive NK cell therapy, pre-existing HLA-mismatches in the host versus graft direction and concomitant immune stimulatory cytokine and co-stimulatory molecule/ligand expression of feeder cells enhance rejection of feeder cells by the host's immune system.

The invention further relates to the artificial feeder cells, comprising an expression vector, which expresses at least one cytokine and additional co-stimulatory ligands or activating surface molecules and which are used in the methods of the invention. The advantages and advantageous embodiments described above with regard to the methods of the invention equally apply also to the artificial feeder cells of the invention, such that it shall be referred to the above.

Further preferably, an artificial feeder cell line is provided for activating and expanding NKG2C+NK subsets, comprising an expression vector, which expresses artificial β2-microglobulin-HLA-E constructs (designated HLA-E-UL40sp; SEQ ID NO: 5 and SEQ ID NO: 6) which are fused to nonamer UL40 leader peptide sequences of HCMV strain AD169 (SEQ ID NO: 3) and HCMV isolate BE/1/2010 (SEQ ID NO: 2), respectively, or wherein the artificial feeder cell line is loaded with nonamer peptides derived from HLA-G-leader peptide/UL40 signal peptide from HCMV isolate BE/1/2010 (SEQ ID NO: 2) and UL40 signal peptide from several other HCMV strains (SEQ ID NO: 1) wherein said artificial feeder cell is genetically engineered and secretes human interleukin 2 (IL-2), or wherein said artificial feeder cell line is genetically engineered and secretes IL-2 and simultaneously expresses membrane-anchored human IL-15-DAP12mut-ITAM (mIL-15d).

Further preferably, an artificial feeder cell line is provided, wherein said artificial feeder cells are genetically engineered and secretes human interleukin 2 (IL-2), or wherein said artificial feeder cell line is genetically engineered and secretes IL-2 and simultaneously expresses membrane-anchored human IL-15-DAP12mut-ITAM (mIL-15d), and wherein said feeder cell line comprises an expression vector, which expresses the cognate surface-antigen for the CAR, wherein said cognate antigen is represented by tumor-associated antigens (TAAs) EGFRvIII and PSCA.

Further preferably, an artificial feeder cell line is provided, wherein said artificial feeder cells are genetically engineered and secretes human interleukin 2 (IL-2), or wherein said artificial feeder cell line is genetically engineered and secretes IL-2 and simultaneously expresses membrane-anchored human IL-15-DAP12mut-ITAM (mIL-15d), and wherein said feeder cell line is engineered and expresses an epitope binding domain on the surface of the feeder cell comprising at least one $V_H$ and/or $V_L$ domain of a monoclonal antibody, preferably a scFv, more preferably a membrane-bound c-myc-single chain antibody, most preferably scFv(9E10)-tm of SEQ ID NO: 12 specific for an epitope-tag implemented in the CAR. By including appropriate membrane-bound antibodies for activating NK cell receptors in feeder cells this embodiment has also the advantage that NK cell subsets can target-specifically be expanded.

In a preferred embodiment, the artificial feeder cell lines express inhibitory C1, C2, Bw4 ligands for KIRs, stably express the "Prostate Stem Cell Antigen" (PSCA) as surface marker, and are genetically engineered to express either a secreted form of IL-2 simultaneously with 4-1BBL or a secreted form of IL-2 simultaneously with 4-1BBL and membrane-anchored human IL-15-DAP12mut-ITAM (mIL-15d). The artificial feeder cell lines avoid hyper-activation of NK cells, avoids missing self-activation of NK cells yet induce the strong expansion of functional NK cells, preserve tolerance against autologous or allogeneic target cells with protective HLA expression and is able to elicit ADCC against antibody-opsonized KIR/KIR-ligand-matched target cells.

In a further preferred embodiment, for selective expansion of NK cell subsets, the artificial feeder cells are modified with ligands for activating NK cell receptors. Loading of HCMV UL40 isolate BE/1/2010/HLA-G-Leader peptide VMAPRTLFL (SEQ ID NO: 2), HCMV UL40/HLA-C-Leader peptide VMAPRTLLL (SEQ ID NO: 1) on HLA-E of artificial feeder cell lines or genetic engineering of feeder cell lines with an artificial β2-microglobulin-HLA-E-protein fused to the HCMV-Leader peptides VMAPRTLIL (SEQ ID NO: 3) resulting in HLA-EUL40-sp-VMAPRTLIL (SEQ ID NO: 5) or VMAPRTLFL (SEQ ID NO: 2) resulting in HLA-E-UL40-sp-VMAPRTLFL (SEQ ID NO: 6) and engineered to express either the secreted form of IL-2 or the secreted form of IL-2 plus mIL-15d surprisingly induced a selective outgrowth of NKG2C+-NK cells from the CD56bright NK cell subset.

In a further preferred embodiment, for selective expansion of CAR-modified NK cell fractions but also of NK subsets, a membrane-bound antibody derivative is genetically implemented into feeder cells, which binds to an activating NK cell receptor of interest or to a cognate epitope tag implemented in the ectodomain of the transduced CAR. Feeder cells containing a membrane-bound antibody directed against c-myc epitope, genetically engineered with IL-2 provided only suboptimal activation signals for expansion of NK cells but surprisingly induced a selective outgrowth of NK cells containing a c-myc-tagged DAP12-based CAR.

In a further preferred embodiment, for selective expansion of CAR-NK cells, artificial feeder cells either endogenously expressing or genetically modified to express the cognate ligand (i.e. TAA) for the CAR are used. Artificial feeder cell lines either genetically engineered with the TAA Prostate Stem Cell Antigen (PSCA) or with the neo-antigen EGFRvIII plus transgenic IL-2 or in combination with transgenic mIL-15d, respectively, provided only suboptimal activation signals for expansion of non-modified NK cells but unexpectedly induced a selective outgrowth of NK cells modified with a DAP12-based CARs specific for PSCA and EGFRvIII, respectively.

In a most preferred embodiment, the present invention provides artificial $PC3^{PSCA}$-derived feeder cells, which are genetically engineered and comprise expression vectors that express a secreted form of IL-2 simultaneously with 4-1BBL or express a secreted form IL-2, simultaneously with 4-1BBL and mIL-15d. Although containing inhibitory NKG2A- and KIR-ligands said feeder cells unexpectedly induce outgrowth of NK cells from PBMCs and strongly expand NK cells from PBMCs and purified NK cell preparations, respectively. Furthermore, expanded NK cells remained tolerant when encountering autologous cells but were still functional in killing HLA-deficient K562 tumor cells. Expanded feeder cells strongly upregulated the activation marker TIM-3 and unexpectedly strongly upregulated high affinity IL-2 receptor (i.e. indicated by the alpha chain of IL-2R, CD25) but on the other hand had no upregulation of immune checkpoint molecules PD1 and TIGIT.

In a further most preferred embodiment the present invention provides artificial PC3$^{PSCA}$-derived feeder cells which are genetically engineered and comprise an expression vector which expresses the cognate surface antigen for the CAR, wherein said cognate antigen is represented by tumor-associated antigen PSCA and EGFRvIII, and a secreted form of IL-2 or a secreted form IL-2 simultaneously expressed with membrane-anchored human IL-15-DAP12mut-ITAM (mIL-15d) without expressing 4-BBL. Such artificial feeder cell lines provided suboptimal activation signals for expansion of non-modified NK cells but surprisingly induced a selective outgrowth of NK cells modified with DAP12-based CARs specific for PSCA and EGFRvIII, respectively.

Said EGFRvIII and said PSCA are preferably of human origin. Most preferably, said EGFRvIII and said PSCA, which are expressed by the artificial feeder cell lines of the invention, have an amino acid sequence of SEQ ID NO: 8 and SEQ ID NO:7, respectively.

In a further aspect, the present invention provides artificial PC3$^{PSCA}$-derived feeder cells which are genetically engineered and comprise an expression vector which expresses an anti-c-myc-tag single chain antibody fragment fused to an artificial transmembrane domain (scFv(9E10)-tm) and a secreted form of IL-2 or a secreted form IL-2 simultaneously expressed with membrane-anchored human IL-15-DAP12mut-ITAM (mIL-15d) without expressing 4-BBL. Such artificial feeder cell lines provided suboptimal activation signals for expansion of non-modified NK cells but surprisingly induced a selective outgrowth of NK cells containing a c-myc-tagged CAR.

In a further embodiment, the invention includes IL-2 and IL-2/mIL-15d-modified artificial PC3$^{PSCA}$-derived feeder cells which provided only suboptimal activation signals for expansion of non-modified NK cells, but which unexpectedly activate and expand NKG2C+NK cell subsets upon loading of endogenous HLA-E of said feeder cells with activating peptides VMAPRTLLL (SEQ ID NO: 1) and VMAPRTLFL (SEQ ID NO:2) derived from UL40 from different HCMV strains. SEQ ID NO: 1 is identical to leader peptides from HLA class I alleles A*01, A*03, A*11, A*29, A*30, A*31, A*32, A*33, A*36, A*74 and of HLA C alleles Cw*02 and Cw*15. SEQ ID NO:2 is identical to a nonamer peptide derived from the signal peptide of HLA-G (SEQ ID NO: 2)). Said loading of HLA-E with peptides provides the cognate ligand for the NKG2C-receptor of NK cells. Likewise, the invention includes feeder cells genetically engineered to express an artificial β2-microglobulin-HLA-E-protein fused to the HCMV UL40-leader peptides VMAPRTLIL (SEQ ID NO: 5) and VMAPRTLFL (SEQ ID NO: 6) for selective activation and expansion of NKG2C+ cell subsets.

The invention relates further to NK cells, CAR-NK cells or NKG2C+-NK cells, which were expanded according to the methods described herein. Said NK cells, CAR-NK cells or NKG2C+-NK cells are characterized in that said expanded NK cells are not hyper-activated and are tolerant to cells expressing protective levels of inhibitory self-ligands, having increased cytotoxicity towards tumor cells or pathogen-infected cells with loss of protective inhibitory self-ligands, having increased cytotoxicity towards tumor cells or pathogen-infected cells displaying activating HLA-E-peptide complexes. Said NK cells, CAR-NK cells or NKG2C+-NK cells are particularly characterized by an upregulation of CD25 in at least 30% of NK cells. Moreover, said NK cells, CAR-NK cells or NKG2C+-NK cells are not exhausted and show expression of TIGIT in less than 5% and show expression of PD-1 in less than 25% of NK cells.

Both, the artificial feeder cells as well as the NK cells, CAR-NK cells or NKG2C+-NK cells, which were expanded according to the methods described herein, are of high commercial interest. The artificial feeder cells are most suitable to provide NK cells, CAR-NK cells or NKG2C+-NK cells for individual cancer therapy. The NK cells, CAR-NK cells or NKG2C+-NK cells are most suitable for use in methods of cancer treatment and treatment of viral infections, especially as personalized medicines.

The NK cells, CAR-NK cells or NKG2C+-NK cells, which were expanded according to the methods described herein, may be formulated for administration to a subject using techniques known to the skilled artisan. Formulations comprising populations of said NK cells may include pharmaceutically acceptable excipient(s). Examples of generally used excipients include, without limitation: saline, buffered saline, dextrose, water- for- infection, glycerol, ethanol, and combinations thereof, stabilizing agents, solubilizing agents and surfactants, buffers and preservatives, tonicity agents, bulking agents, and lubricating agents. The formulations comprising populations of said NK cells will typically have been prepared and cultured in the absence of any non-human components, such as animal serum (e.g., bovine serum albumin).

The choice of formulation, i.e. type of pharmaceutical composition for administering NK cells, CAR-NK cells or NKG2C+-NK cells for a given application will depend on a variety of factors.

Prominent among these will be the species of subject, the nature of the disorder, dysfunction, or disease being treated and its state and distribution in the subject, the nature of other therapies and agents that are being administered, the optimum route for administration of the NK cells, CAR-NK cells or NKG2C+-NK cells, survivability of NK cells, CAR-NK cells or NKG2C+-NK cells via the route, the dosing regimen, and other factors that will be apparent to those skilled in the art. In particular, for instance, the choice of suitable carriers and other additives will depend on the exact route of administration and the nature of the particular dosage form, for example, liquid dosage form (e.g., whether the composition is to be formulated into a solution, a suspension, gel or another liquid form, such as a time release form or liquid-filled form).

Examples of compositions comprising NK cells, CAR-NK cells or NKG2C+-NK cells include liquid preparations, including suspensions and preparations for intramuscular or intravenous administration (e.g., injectable administration), such as sterile suspensions or emulsions. Such compositions may comprise an admixture of NK cells, CAR-NK cells or NKG2C+-NK cells with a suitable carrier, diluent, or excipient such as sterile water, physiological saline, glucose, dextrose, or the like. The compositions can contain auxiliary 36 substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE," 17th edition, 1985, incorporated herein by reference, may be consulted to prepare suitable preparations, without undue experimentation.

Various additives often will be included to enhance the stability, sterility, and isotonicity of the compositions, such as antimicrobial preservatives, antioxidants, chelating agents, and buffers, among others. Prevention of the action of microorganisms can be ensured by various antibacterial and antifungal agents, which are known to the person skilled in the art. In many cases, it will be desirable to include isotonic agents, for example, sugars, sodium chloride, and the like. Prolonged absorption of the injectable pharmaceutical form can be brought about by the use of agents that delay absorption, for example, aluminum monostearate, and gelatin.

According to the present invention, however, any vehicle, diluent, or additive used would have to be compatible with the cells.

Typically, the compositions will be isotonic, i.e., they will have the same osmotic pressure as blood and lacrimal fluid when properly prepared for administration.

The desired isotonicity of the compositions of this invention may be accomplished using sodium chloride, or other pharmaceutically acceptable agents such as dextrose, boric acid, sodium tartrate, propylene glycol, or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount, which will achieve the selected viscosity. Viscous compositions are normally prepared from solutions by the addition of such thickening agents.

A pharmaceutically acceptable preservative or cell stabilizer can be employed to increase the life of NK cells, CAR-NK cells or NKG2C+-NK cells compositions. If such preservatives are included, it is well within the purview of the skilled artisan to select compositions that will not affect the viability or efficacy of the NK cells, CAR-NK cells or NKG2C+-NK cells.

Those skilled in the art will recognize that the components of the compositions should be chemically inert. This will present no problem to those skilled in chemical and pharmaceutical principles. Problems can be readily avoided by reference to standard texts or by simple experiments (not involving undue experimentation) using information provided by the disclosure, the documents cited herein, and generally available in the art.

Sterile injectable solutions can be prepared by incorporating the cells utilized in practicing the present invention in the required amount of the appropriate solvent with various amounts of the other ingredients, as desired.

In some embodiments, NK cells, CAR-NK cells or NKG2C+-NK cells are formulated in a unit dosage injectable form, such as a solution, suspension, or emulsion. Pharmaceutical formulations suitable for injection of NK cells, CAR-NK cells or NKG2C+-NK cells typically are sterile aqueous solutions and dispersions. Carriers for injectable formulations can be a solvent or dispersing medium containing, for example, water, saline, phosphate buffered saline, polyol (for example, glycerol, propylene glycol, liquid polyethylene glycol, and the like), and suitable mixtures thereof.

The skilled person can readily determine the amount of cells and optional additives, vehicles, and/or carrier in compositions to be administered in methods of the invention. Typically, any additives (in addition to the cells) are present in an amount of 0.001 to 50 wt % in solution, such as in phosphate buffered saline. The active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %.

NK cells, CAR-NK cells or NKG2C+-NK cells may be encapsulated by membranes, as well as capsules, prior to implantation. It is contemplated that any of the many methods of cell encapsulation available may be employed. In some embodiments, cells are individually encapsulated. In some embodiments, many cells are encapsulated within the same membrane. In embodiments in which the cells are to be removed following implantation, a relatively large size structure encapsulating many cells, such as within a single membrane, may provide a convenient means for retrieval. A wide variety of materials may be used in various embodiments for microencapsulation of NK cells, CAR-NK cells or NKG2C+-NK cells. Such materials include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers. Techniques for microencapsulation of cells that may be used for administration of NK cells, CAR-NK cells or NKG2C+-NK cells are known to those of skill in the art and are described, for example, in Chang, P., et al., 1999; Matthew, H. W., et al, 1991; Yanagi, K., et al., 1989; Cai Z. H., et al, 1988; Chang, T. M., 1992 and in U.S. Pat. No. 5,639,275 (which, for example, describes a biocompatible capsule for long-term maintenance of cells that stably express biologically active molecules. Additional methods of encapsulation are in European Patent Publication No. 301,777 and U.S. Pat. Nos. 4,353,888; 4,744,933; 4,749,620; 4,814,274; 5,084,350; 5,089,272; 5,578,442; 5,639,275; and 5,676,943. All of the foregoing are incorporated herein by reference in parts pertinent to encapsulation of NK cells, CAR-NK cells or NKG2C+-NK cells.

Certain embodiments incorporate NK cells, CAR-NK cells or NKG2C+-NK cells into a polymer, such as a biopolymer or synthetic polymer. Examples of biopolymers include, but are not limited to, fibronectin, fibrin, fibrinogen, thrombin, collagen, and proteoglycans. Other factors, such as the cytokines discussed above, can also be incorporated into the polymer. In other embodiments of the invention, NK cells, CAR-NK cells or NKG2C+-NK cells may be incorporated in the interstices of a three-dimensional gel. A large polymer or gel, typically, will be surgically implanted. A polymer or gel that can be formulated in small enough particles or fibers can be administered by other common, more convenient, non-surgical routes.

NK cells, CAR-NK cells or NKG2C+-NK cells may be administered with other pharmaceutically active agents. In some embodiments one or more of such agents are formulated together with NK cells, CAR-NK cells or NKG2C+-NK cells for administration. In some embodiments the NK cells, CAR-NK cells or NKG2C+-NK cells and the one or more agents are in separate formulations. In some embodiments the compositions comprising the NK cells, CAR-NK cells or NKG2C+-NK cells and/or the one or more agents are formulated with regard to adjunctive use with one another.

NK cells, CAR-NK cells or NKG2C+-NK cells may be administered after pretreatment with immunosuppressive agents, such as a corticosteroid, cyclosporin A, a cyclosporin-like immunosuppressive agent, cyclophosphamide, antithymocyte globulin, azathioprine, rapamycin, FK-506, and a macrolide-like immunosuppressive agent other than FK-506 and rapamycin. In certain embodiments, such immunosuppressive agents include a corticosteroid, cyclosporin A, azathioprine, cyclophosphamide, rapamycin, and/or FK 506. Immunosuppressive agents in accordance with the foregoing may be the only such additional agents or may be combined with other agents, such as other agents noted herein. Other immunosuppressive agents include Tacrolimus, Mycophenolate mofetil, and Sirolimus.

Such other agents also include antibiotic agents, antifungal agents, and antiviral agents, to name just a few other pharmacologically active substances and compositions that may be used in accordance with embodiments of the invention.

Order of administration, formulations, doses, frequency of dosing, and routes of administration of NK cells, CAR-NK cells or NKG2C+-NK cells generally will vary with the disorder or disease being treated, its severity, the subject, other therapies that are being administered, the stage of the disorder or disease, and prognostic factors, among others. General regimens that have been established for other treatments provide a framework for determining appropriate dosing in NK cells, CAR-NK cells or NKG2C+-NK cells-mediated direct or adjunctive therapy. These, together with the additional information provided herein, will enable the skilled artisan to determine appropriate administration procedures in accordance with embodiments of the invention, without undue experimentation.

For therapeutic applications, NK cells, CAR-NK cells or NKG2C+-NK cells can be administered to a subject by any of a variety of routes known to those skilled in the art that may be used to administer cells to a subject. Among methods that may be used in this regard in embodiments of the invention are methods for administering NK cells, CAR-NK cells or NKG2C+-NK cells by a parenteral route. Parenteral routes of administration useful in various embodiments of the invention include, among others, administration by intravenous, intraarterial, intracardiac, intra-articular (joint), intraspinal, intrathecal (spinal fluids), intraosseous, intraarticular, intrasynovial (joint fluid area), intracutaneous, intradermal, subcutaneous (s.c, s.q., sub-Q, Hypo), and/or intramuscular injection. Any known device useful for parenteral injection or infusion of the formulations can be used to effect such administration. Injections can be performed as bulk injections or continuous flow injections. In some embodiments intravenous, intraarterial, intracutaneous, intradermal, subcutaneous and/or intramuscular injection are used. In some embodiments intravenous, intraarterial, intracutaneous, subcutaneous, and/or intramuscular injection are used. In various embodiments of the invention NK cells, CAR-NK cells or NKG2C+-NK cells are administered by systemic injection. Systemic injection, such as intravenous injection, offers one of the simplest and least invasive routes for administering NK cells, CAR-NK cells or NKG2C+-NK cells. In a variety of embodiments NK cells, CAR-NK cells or NKG2C+-NK cells may be administered by targeted and/or localized injections to ensure optimum effect at the target sites.

NK cells, CAR-NK cells or NKG2C+-NK cells may be administered to the subject through a hypodermic needle by a syringe in some embodiments of the invention. In various embodiments, NK cells, CAR-NK cells or NKG2C+-NK cells are administered to the subject through a catheter. In a variety of embodiments, NK cells, CAR-NK cells or NKG2C+-NK cells are administered by surgical implantation. Further in this regard, in various embodiments of the invention, NK cells, CAR-NK cells or NKG2C+-NK cells are administered to the subject by implantation using an arthroscopic procedure. In some embodiments NK cells, CAR-NK cells or NKG2C+-NK cells are administered to the subject in or on a solid support, such as a polymer or gel. In various embodiments, NK cells, CAR-NK cells or NKG2C+-NK cells are administered to the subject in an encapsulated form.

In additional embodiments of the invention, NK cells, CAR-NK cells or NKG2C+-NK cells are suitably formulated for oral, rectal, epicutaneous, intraocular, nasal, and/or pulmonary, most preferably for intraocular, and/or pulmonary delivery and are administered accordingly. Compositions can be administered in dosages and by techniques well known to those skilled in the medical and veterinary arts taking into consideration such factors as the age, sex, weight, and condition of the particular patient, and the formulation that will be administered (e.g., solid vs. liquid). Doses for humans or other mammals can be determined without undue experimentation by the skilled artisan, from this disclosure, the documents cited herein, and the knowledge in the art. The optimal dose of NK cells, CAR-NK cells or NKG2C+-NK cells for some embodiments will be in the range of doses used for cancer immunotherapy. For fairly pure preparations of NK cells, CAR-NK cells or NKG2C+-NK cells, optimal doses in various embodiments will comprise at least $10^1$ NK cells, CAR-NK cells or NKG2C+-NK cells/kg of recipient mass per administration. In some embodiments the optimal dose per administration will be between 105 to 107 NK cells, CAR-NK cells or NKG2C+-NK cells/kg. In many embodiments the optimal dose per administration will be 5×105 to 5×10$^6$ NK cells, CAR-NK cells or NKG2C+-NK cells/kg.

It is to be appreciated that a single dose may be delivered all at once, fractionally, or continuously over a period of time. The entire dose also may be delivered to a single location or spread fractionally over several locations. In various embodiments, NK cells, CAR-NK cells or NKG2C+-NK cells may be administered in an initial dose, and thereafter maintained by further administration of NK cells, CAR-NK cells or NKG2C+-NK cells. NK cells, CAR-NK cells or NKG2C+-NK cells may be administered by one method initially, and thereafter administered by the same method or one or more different methods. The subject's NK cells, CAR-NK cells or NKG2C+-NK cells levels can be maintained by the ongoing administration of the cells. Various embodiments administer the NK cells, CAR-NK cells or NKG2C+-NK cells either initially or to maintain their level in the subject or both by intravenous injection. In a variety of embodiments, other forms of administration are used, dependent upon the patient's condition and other factors, discussed elsewhere herein. In some embodiments NK cells, CAR-NK cells or NKG2C+-NK cells are administered to a subject in one dose. In others NK cells, CAR-NK cells or NKG2C+-NK cells are administered to a subject in a series of two or more doses in succession. In some other embodiments wherein NK cells, CAR-NK cells or NKG2C+-NK cells are administered in a single dose, in two doses, and/or more than two doses, the doses may be the same or different, and they are administered with equal or with unequal intervals between them. In some embodiments, NK cells, CAR-NK cells or NKG2C+-NK cells are administered over a period of less than one day. In other embodiment they are administered over two, three, four, five, or six days. In some embodiments NK cells, CAR-NK cells or NKG2C+-NK cells are administered one or more times per week, over a period of weeks. In other embodiments they are administered over a period of weeks for one to several months.

In various embodiments they may be administered over a period of months. In others they may be administered over a period of one or more years.

The NK cells, CAR-NK cells or NKG2C+-NK cells and the pharmaceutical composition according to the invention are particularly useful in the treatment of certain types of cancer or viral infections. Accordingly, the invention provides the NK cells, CAR-NK cells or NKG2C+-NK cells and/or the pharmaceutical composition as described herein for use in immunotherapy of cancer and virus infections.

The NK cells, CAR-NK cells or NKG2C+-NK cells and the pharmaceutical composition according to the invention can be used in autologous and allogenic therapy of certain types of cancer or viral infections. In a preferred embodiment, the NK cells, CAR-NK cells or NKG2C+-NK cells and the pharmaceutical composition according to the invention are used in autologous therapy. In a further preferred embodiment, the NK cells, CAR-NK cells or NKG2C+-NK cells and the pharmaceutical composition according to the invention are used in allogenic therapy.

Most preferred is the use of the NK cells, CAR-NK cells or NKG2C+-NK cells and the pharmaceutical composition according to the invention in autologous therapy. However, the NK cells, CAR-NK cells or NKG2C+-NK cells and the pharmaceutical composition according to the invention have also a great potential in allogenic therapy.

In a further embodiment, the invention relates to method of treatment of cancer and/or viral infections comprising the administration of a therapeutically effective dose of the NK cells, CAR-NK cells or NKG2C+-NK cells and/or the pharmaceutical composition as described herein to a subject in need thereof.

In yet a further embodiment, the invention relates to the use of the NK cells, CAR-NK cells or NKG2C+-NK cells and/or the pharmaceutical composition for the preparation of a medicament for the treatment of cancer or virus infections.

Said cancer is for example selected from malignant (and preferably solid) tumors of epithelial or mesenchymal cells, breast cancer, prostate cancer, pancreatic cancer, adrenal cancer, melanoma, lung cancer, colon cancer, leukemia (a liquid or non-solid tumor), soft tissue and bone sarcomas, neuroendocrine tumors such as islet cell carcinoma or medullary carcinoma of the thyroid, squamous carcinomas (particularly of the head and neck), adenocarcinomas and gliosarcomas such as glioblastoma multiforme.

In a more preferred embodiment, said cancer is selected from small cell lung cancer, small cell renal cancer, breast cancer, prostate cancer, bladder cancer and malignant glioma. A virus infection is for example an infection by human cytomegalovirus (HCMV), human immunodeficiency virus (HIV), Epstein-Barr virus (EBV) or by a herpes virus such as varicella-zoster virus (VZV).

In a further preferred embodiment, the NK cells, CAR-NK cells or NKG2C+-NK cells and/or the pharmaceutical composition are used in a combination therapy with other anti-tumor drugs.

Preferred other anti-tumor drugs are tyrosine kinase inhibitors that slow down or halt cell growth. Suitable tyrosine kinase inhibitors for use in the combination therapy according to the invention are for example selected from gefitinib, erlotinib, afatinib and osimertinib for the treatment of lung cancer.

In a further preferred embodiment the NK cells, CAR-NK cells or NKG2C+-NK cells and/or the pharmaceutical composition are used in a combination therapy with tumor targeting monoclonal antibodies such as rituximab (mAb to B cell-specific lineage surface antigen CD20), trastuzumab (mAb to human epidermal growth factor receptor 2 (EGFR2, ErbB2/HER2)) or cetuximab (mAb to EGFR (ErbB1/HER1)), and bispecific or trispecific killer cell-engagers, representing targeting moieties fused to the Fc portion of IgG that facilitates cytotoxicity against target cells by ADCC.

In a further preferred embodiment the NK cells, CAR-NK cells or NKG2C+-NK cells and/or the pharmaceutical composition are used in a combination therapy with monoclonal antibodies targeting immune checkpoint molecules (PD-1, TIGIT, PD-1L, PD-2L) such as Nivolumab Atezolizumab, Durvalumab und Avelumabrituximab which might improve persistence and anti-tumor cytotoxicity of NK cells.

Expansion of NK cells can e.g. be performed e.g. according to the methodology as described in Example 2.

A general method for expansion of NK cells such as human NK cells comprises the following steps:
i) Isolation of PBMCs from peripheral blood of healthy donors or patients;
ii) Subsequent cell sorting of NK cells;
iii) HLA analysis and subsequent analysis of KIR/KIR-ligand settings;
iv) Purity testing;
v) Providing artificial feeder cell lines differently engineered to express at least one cytokine such as IL-2 and further co-stimulatory ligand(s) or activating surface molecule(s);
vi) Stimulating NK cell proliferation by co-culture with isolated NK cells;
vii) Investigating the NK cell proliferation by staining with CFSE; and optionally
viii) Counting of the total cell numbers of expanded NK cells; and optionally
ix) Staining cells with a suitably antibody.

In a preferred embodiment, step i) of the NK cell expansion method is performed by gradient centrifugation, such as BIOCOLL gradient centrifugation (Biochrom, Germany).

In a further preferred embodiment, step ii) of the NK cell expansion method is performed e.g. by using a negative NK Cell Isolation Kit (Miltenyi Biotec, Germany).

In a further preferred embodiment, step iv) of the NK cell expansion method is performed e.g. 10 by staining with anti-CD3-FITC and anti-CD56-APC antibodies (Miltenyi Biotec, Germany) to confirm CD56+NK cell purification and depletion of CD3+T lymphocytes.

In a further preferred embodiment, the stimulation of the NK cell proliferation by co-culture with isolated NK cells according to step vi) of the NK cell expansion method is performed e.g. by
Cultivating feeder cells in suitable culture medium, such as complete RPMI-1640 medium in 24 well plates for 24h in a humidified incubator at 5% $CO_2$ and 37° C.;
Substitution of the medium on the next day with suitable NK cell medium, such as NK MACS medium supplemented with 2% NK MACS supplement and 5% human AB serum;
Adding of NK cells after 4-8 h to the feeder cells;
Resuspending the NK cells in new conditioned medium on newly seeded feeder cells every 3-4 days.

Figure 4:
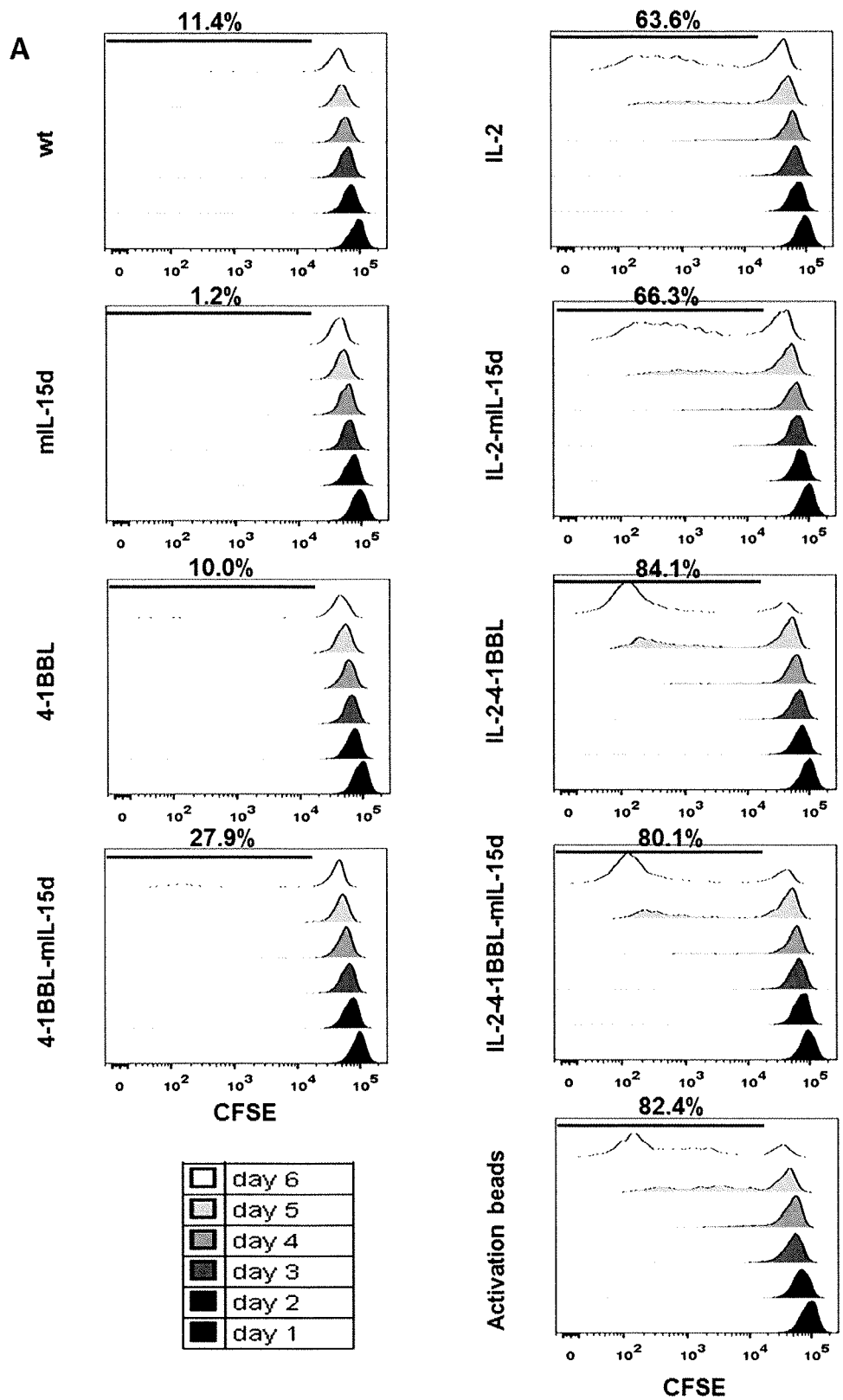
FIG. 4 shows the expansion of primary NK cells from five healthy donors co-cultivated with the different genetically modified PC3$^{PSCA}$-cell lines. Expansion of NK cells using anti-CD2/NKp46-activation beads was included in the experiments. (A) Representative CFSE proliferation analysis of primary NK cells from one donor on six consecutive days using seven different feeder cell lines as well as using PC3 wildtype cells for expansion, and of primary NK cells treated with activation beads and cultivated IL-2 (Proleukin S)/IL-21-supplemented NK MACS medium, respectively. In each graph, the histogram at the bottom depicts the initial CFSE signal on day 1 after NK cell isolation. The left column depicts NK cells co-cultured with unmodified PC3$^{PSCA}$ cells (wt) as well as PC3$^{PSCA}$-derived feeder cells lines devoid of transgenic IL-2. (B) Overview of the means and expansion factors of primary NK cells cultured with the eight different feeder cell lines or activation beads as control. Expansion factor is calculated using cell counts on day 9, relative to the cell count on day 1. (C) Overview of the means and maximal expansion factors of primary NK cells cultured in the presence of IL-2-secreting feeder cells for 27 days.
Figure 4:
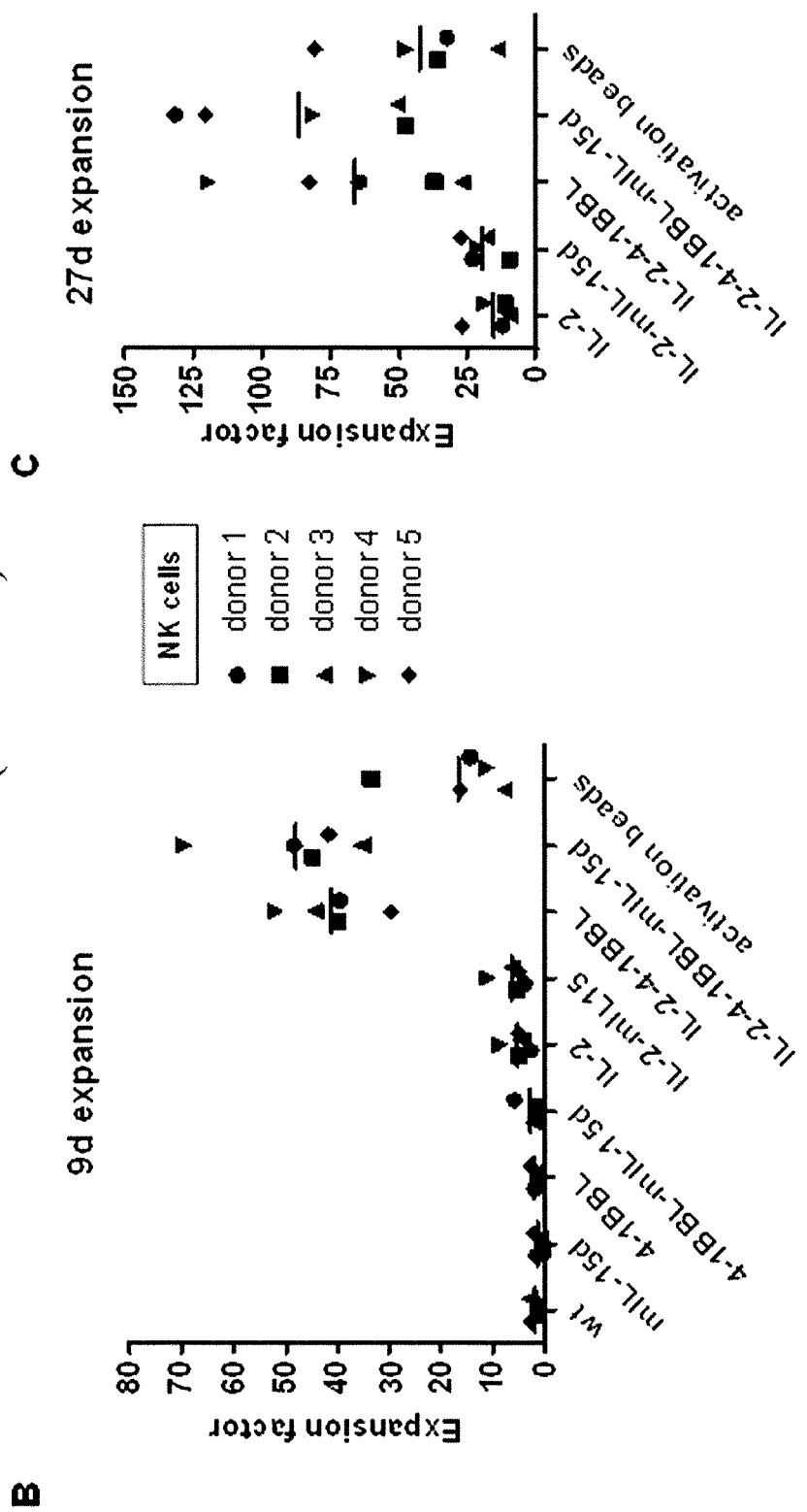

In a further preferred embodiment, step vii) of the NK cell expansion method is performed e.g. daily in the course of 27 days (FIG. 4C).

Figure 11:
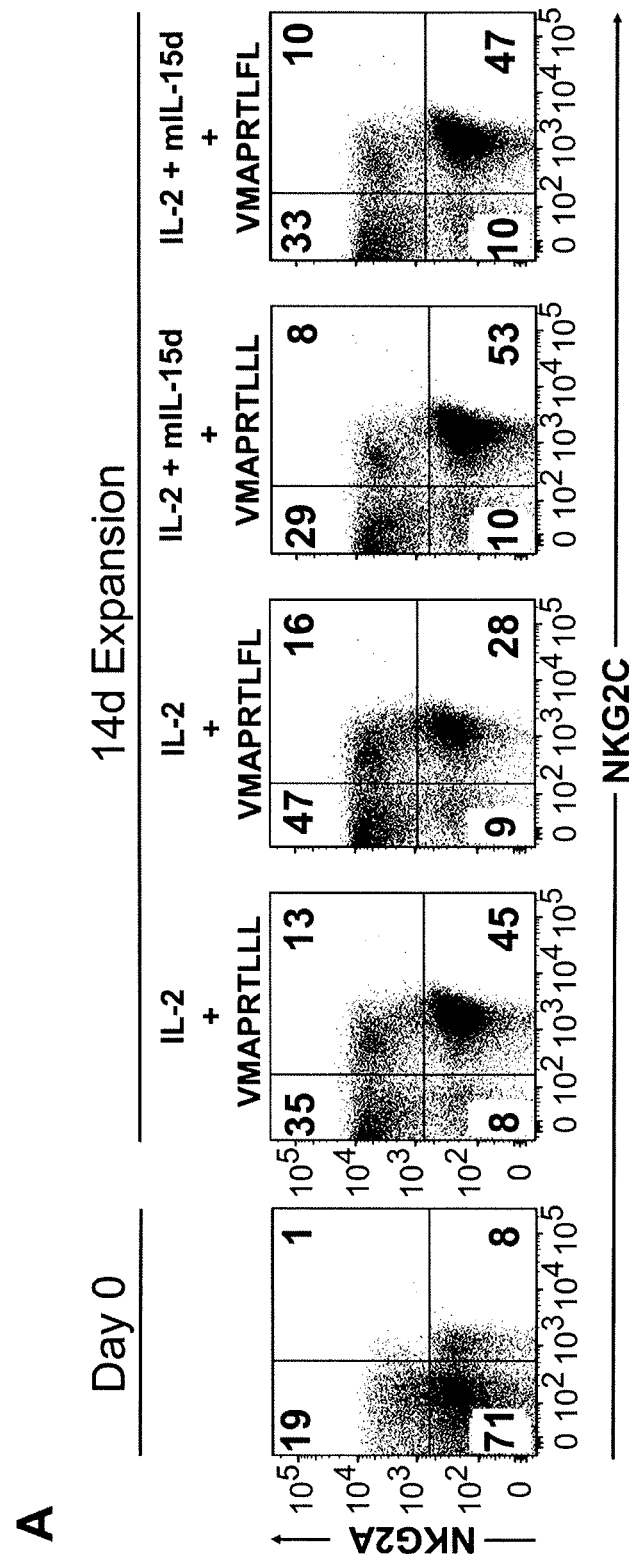
FIG. 11 shows the selective outgrowth of NKG2C+ cells from bulk CD56+ NK cell populations of three donors measured after 14 days of co-cultivation with VMAPRTLFL- (SEQ ID NO: 2) and VMAPRTLLL- (SEQ ID NO: 1) loaded PC3$^{PSCA}$-IL-2 and PC3$^{PSCA}$-IL-2-mIL-15d feeder cells. VMAPRTLFL is present in UL40 signal peptide from HCMV strain BE/1/2010 [61] but also is found in the signal peptide of the non-classical HLA-G molecule. VMAPRTLLL is present in UL40 signal peptides from various hCMV strains [44] and in signal peptides of human HLA class I molecules A*01, A*03, A*11, A*29, A*30, A*31, A*32, A*33, A*36, A*74 and of HLA C alleles Cw*02 and Cw*15 [44]. Both peptides enabled outgrowth of NKG2C+ NK cells. A shows a representative example of selective expansion of NKG2C+ NK cells. Unexpectedly, double-positive NKG2C+/NKG2A+ NK cells were detected indicating that the NKG2C+ NK cell product develop from early NKG2C−/NKG2A+ and NKG2C+/NKG2A+ intermediate states. B shows expansion factors for NKG2C+ NK cells using the peptide-loaded PC3$^{PSCA}$-IL-2 and PC3$^{PSCA}$-IL-2-mIL-15d feeder cells, respectively. Included are expansion rates of NKG2C+ NK cells using corresponding feeder cells without activating peptides. Expansion rates were calculated by dividing the numbers of NKG2C+ NK cells and NKG2C− NK cells at day 14 to measured initial NKG2C+ and NKG2C− cell numbers, respectively, at start of the experiment (day 0).
Figure 11:
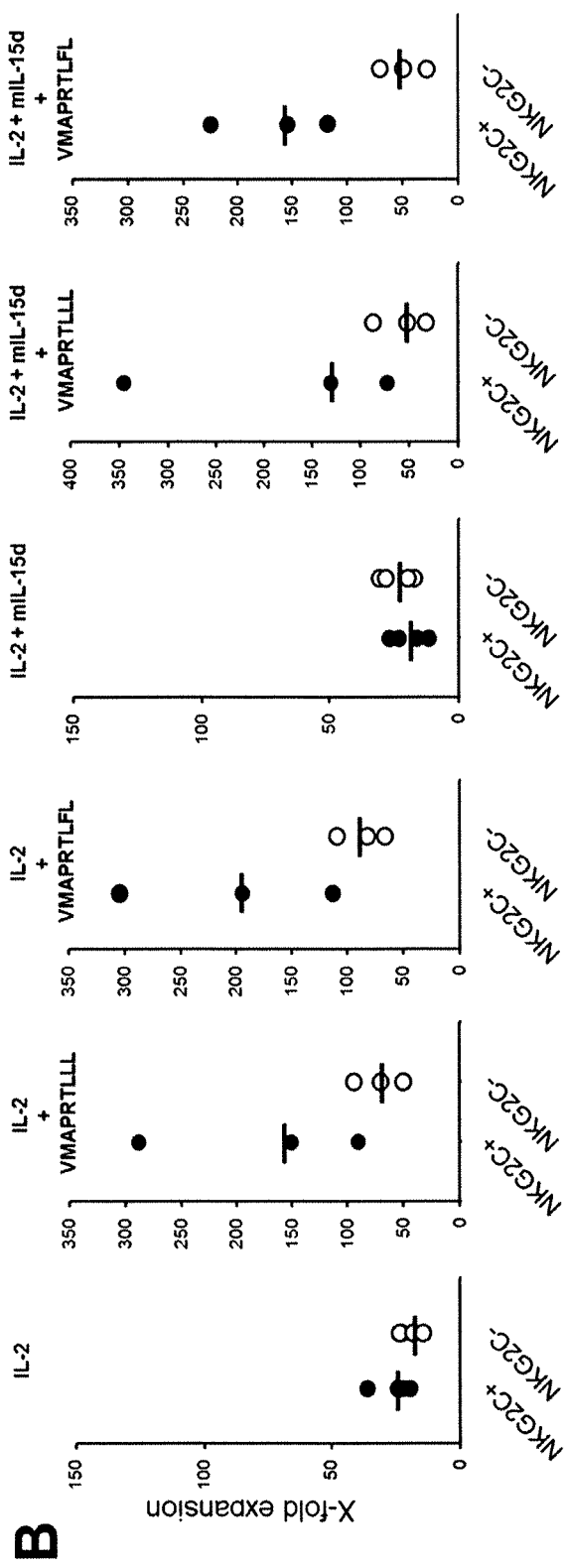

In a further preferred embodiment, optional step ix) of the NK cell expansion method is performed by staining the cells e.g. with anti-CD56-APC (Miltenyi Biotec, Germany); including IgG isotype staining, plus staining for the desired NK subset (i.e. anti-NKG2C for NKG2C+NK cells (FIG. 11, 12), anti-c-myc or analysed for EGFP reporter gene expression for CAR-transduced cells (FIG. 14, 17) and subsequent flow cytometry using a MACSQUANT Analyzer 10 flow cytometer (Miltenyi Biotec, Germany) and FLOWJO version X.0.7 software (Tree Star, USA).

EXAMPLES OF THE INVENTION

The following examples are provided for the sole purpose of illustrating various embodiments of the present invention and are not meant to limit the present invention in any fashion.

Example 1: Generation of NK-Feeder Cell Lines

Figure 1:
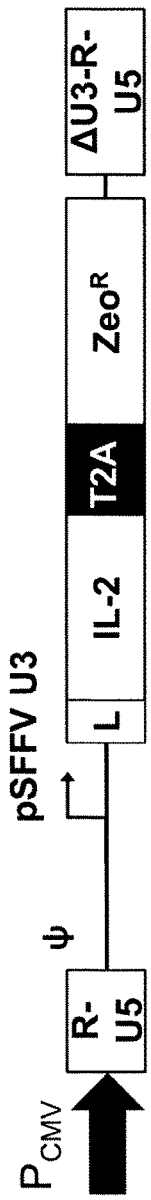
FIG. 1 shows the generation of PC3$^{PSCA}$ feeder cell lines. (A) Schematic representation of IL-2, 4-1 BBL and membrane-bound IL-15 (mIL-15d) lentiviral proportions of vector constructs. 4-1 BBL was fused to a VSV-G epitope tag for detection (SEQ ID NO: 11). The mIL-15d coding sequence consists of IL-15, a c-myc epitope tag fused to the non-functional signal adapter protein DAP12 (mutDAP12) which harbors T91S and T102S mutations in its ITAM (SEQ ID NO: 10). (B) HLA-alleles of PC3$^{PSCA}$ cells and flow cytometry analysis showing the surface expression levels of HLA-ABC and HLA-E of PC3$^{PSCA}$ cells (C) Overview of the stepwise generation of the different PSCA$^{PSCA}$-derived feeder cell lines by lentiviral transduction.
Figure 1:
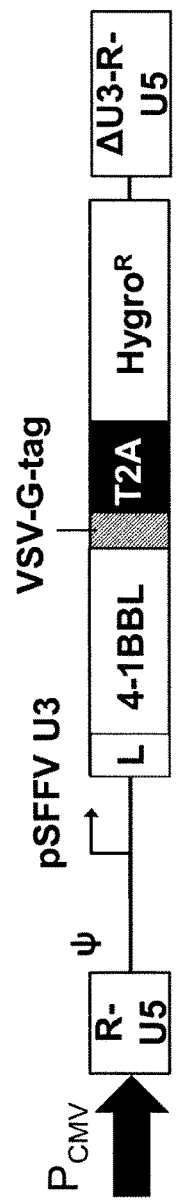
Figure 1:
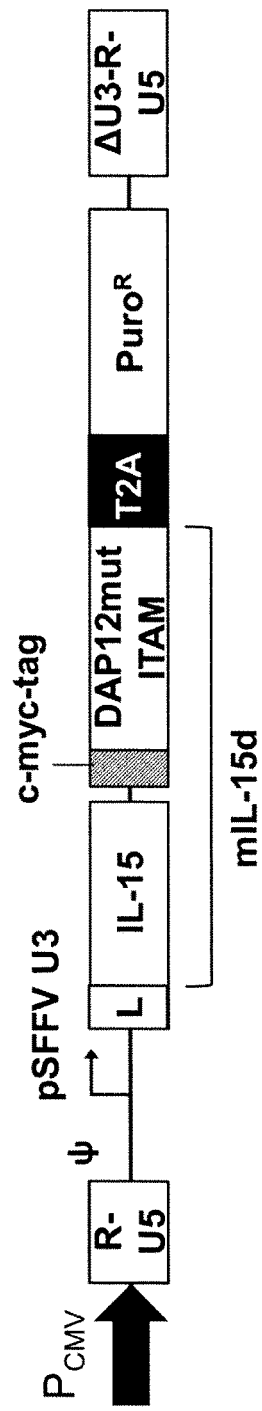
Figure 1:
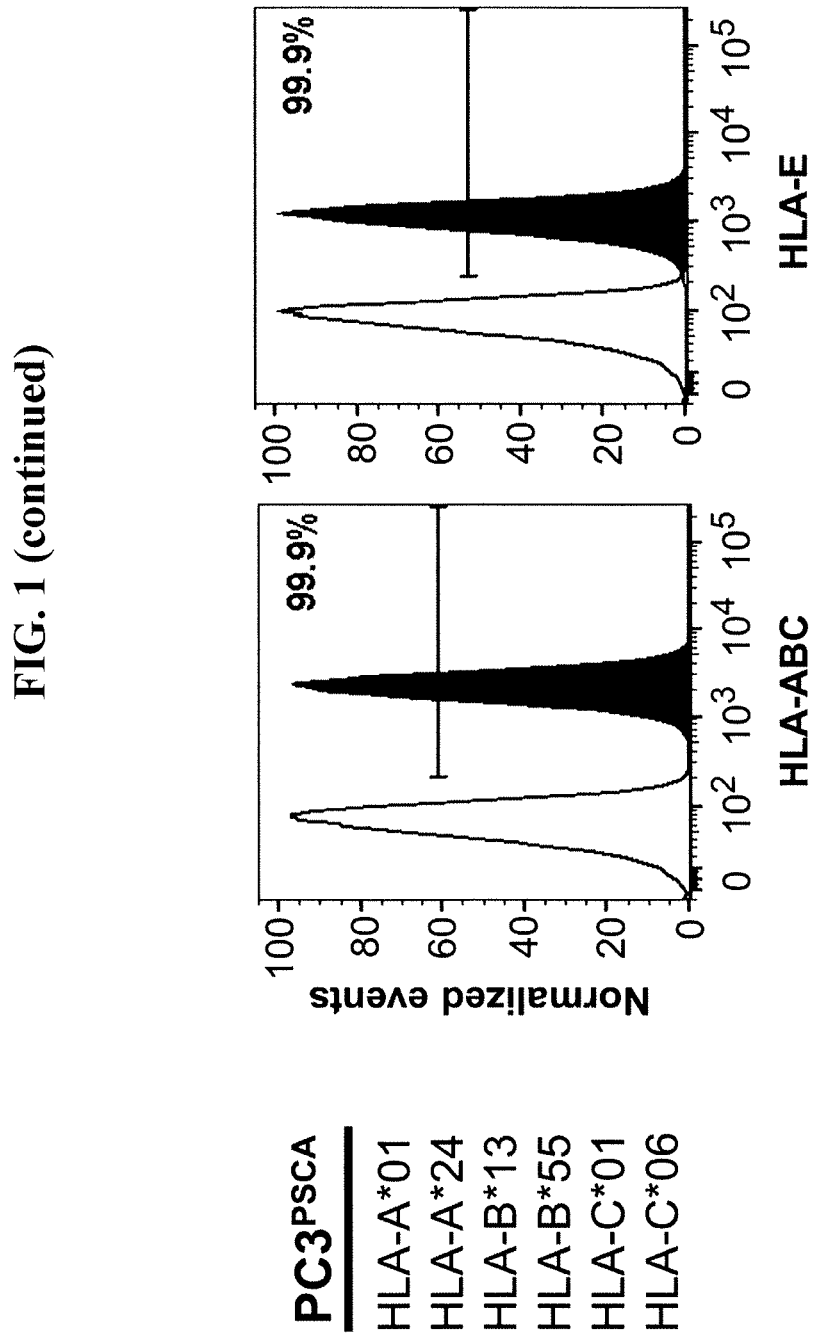
Figure 1:
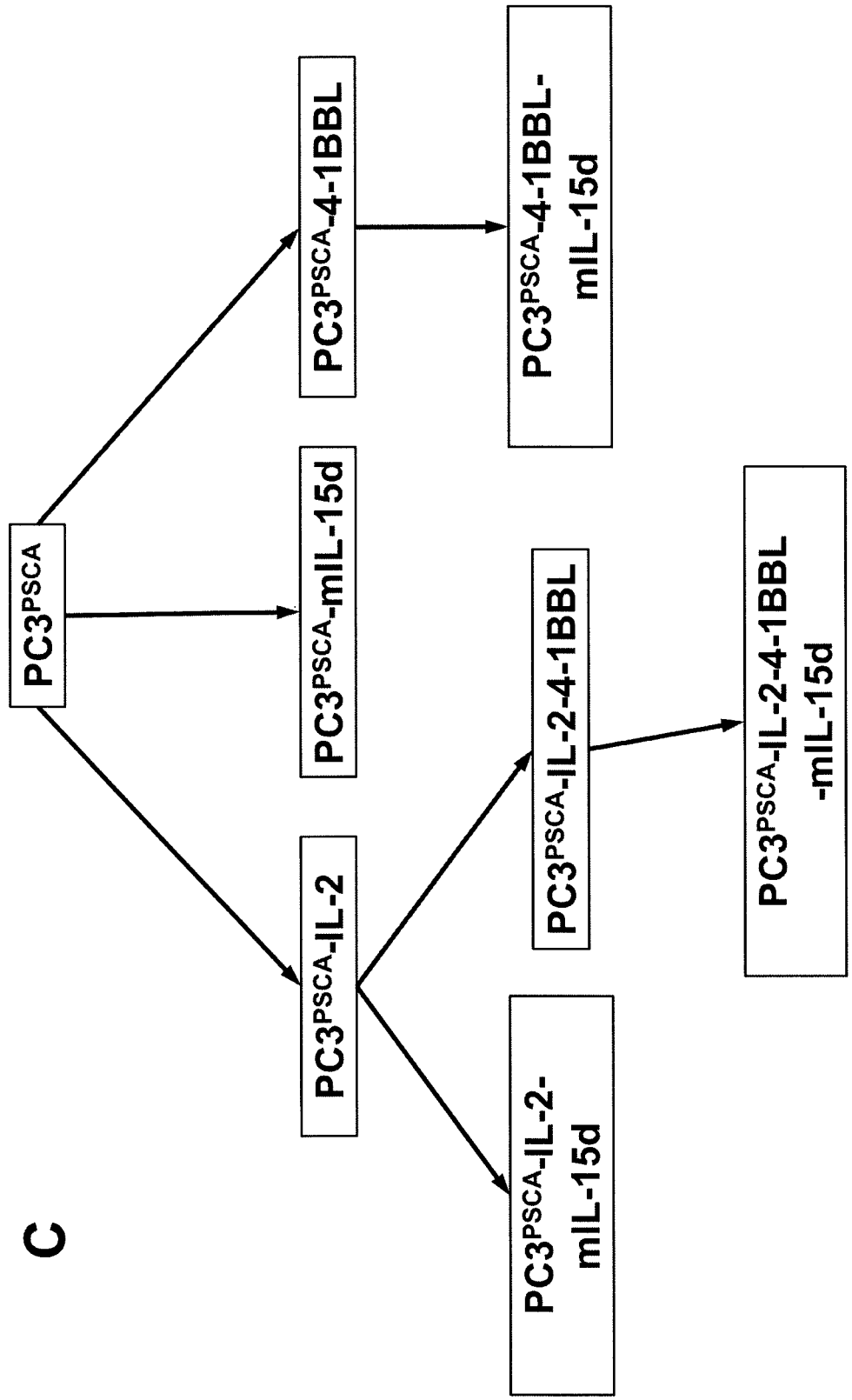

The human prostate cancer cell line $PC3^{PSCA}$ genetically-engineered to express the prostate stem cell antigen (PSCA), has been described previously [65]. $C3^{PSCA}$ cells endogenously express HLA-ABC alleles and HLA-E depicted in FIG. 1b and transgenic human PSCA according to SEQ ID NO: 7. For the generation of the desired feeder cells, the self-inactivating lentiviral pHATtrick vector backbone [65, 66] devoid of the woodchuck hepatitis virus posttranscriptional regulatory element (WPRE), and containing an internal spleen focus forming virus (SFFV) U3 promoter followed by a multiple cloning site, a T2A Thosea assigna virus element fused in frame to a puromycin-, zeocin- or hygromycin B-resistance gene, respectively, was used. IL-2 amplified from cDNA reversely transcribed from PBMCs together with an added 5'-Kozak sequence and restriction sites was ligated in frame to the T2A-site of pHATtrick-T2A-ZEO resulting in pHATtrick-IL-2-T2A-ZEO. A full-length cDNA of membrane-bound 4-1 BBL containing a 5'-Kozak sequence and fused with a VSV-G epitope tag was chemically synthesized and ligated in frame to the T2A-site of pHATtrick-HYGRO resulting in pHATtrick-4-1BBL-HYGRO. A full length cDNA of human IL-15 and including a Kozak sequence, a short C-terminal linker (Gly2Ser1) was chemically synthesized and ligated into MR1.1-DAP12mut-PURO [3] replacing the MR1.1 fragment to generate the lentiviral vector pHATtrick-m-IL15-DAP12mut-T2A-PURO encoding for a membrane-bound IL-15-DAP12mut fusion protein (mIL-15d). Schematic drawings of all constructs are depicted in FIG. 1a.

Lentiviral particles for transduction of $C3^{PSCA}$ cells were produced by a transient three vector packaging protocol as described previously [65]. IL-2, mIL-15d and 4-1BBL were consecutively transduced with respective lentiviral vectors resulting in cell lines depicted in FIG. 1C.

Figure 2:
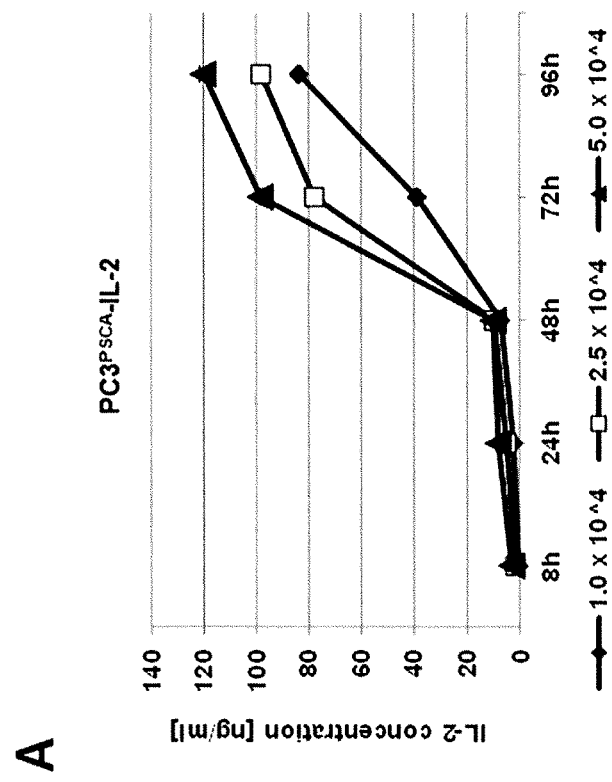
FIG. 2 shows (A) analysis of IL-2 secretion of PC3$^{PSCA}$-IL-2 feeder cells by sandwich ELISA. Cells were seeded at densities of 1.0, 2.5, or 5.0×10$^4$ cells and cell culture supernatants were analyzed at the indicated times. (B) Immunoblot analysis of total protein lysates of wildtype (control) and 4-1 BBL-engineered feeder cells demonstrating ectopic 4-1 BBL expression using a VSV-G-specific antibody and HRP-labeled anti-mouse secondary antibody. (C) Surface expression levels of the membrane-bound mIL-15d were determined by flow cytometry analysis using an APC-coupled anti-c-myc antibody (filled areas). Cells stained with APC-coupled IgG isotype antibody (open areas) served as a control.
Figure 2:
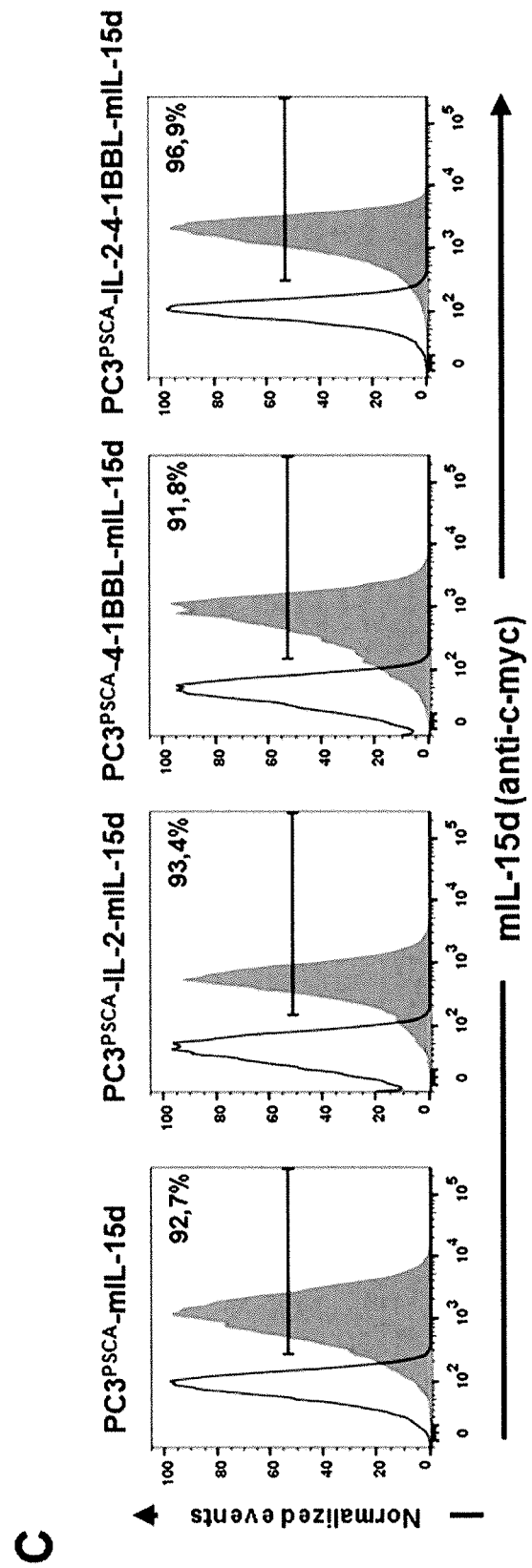

Transductions were performed incubating $5\times10^4$ $C3^{PSCA}$ cells in a 24-well with 2 ml lentiviral supernatants and was repeated on two subsequent days. All $C3^{PSCA}$ feeder cells were selected with respective antibiotics. Expression of secreted IL-2 and membrane-anchored mIL-15d and of 4-1BBL was assessed using supernatants for IL-2 ELISA, Western blot analyses for 4-1 BBL and fluorescence flow cytometry analysis for mIL-15d as depicted in FIG. 2.

Example 2: Expansion of NK Cells Using $C3^{PSCA}$-Derived Feeder Cell Lines Human NK cells were isolated from fresh blood of five healthy donors by BIOCOLL gradient centrifugation (Biochrom, Germany) and subsequent magnet-activated cell sorting using a negative NK Cell Isolation Kit (Miltenyi Biotec, Germany). HLA genotyping and subsequent analysis of KIR/KIR-ligand settings using EMBL/EBI KIR Ligand Calculator confirmed KIR-ligand match of the $PC3^{PSCA}$-derived feeder cells to all donor NK cells (FIG. 3). Staining with anti-CD3-FITC and anti-CD56-APC antibodies (Miltenyi Biotec, Germany) routinely confirmed >90% purity of CD56+ and depletion of CD3+cells. The capability to stimulate NK cell proliferation of $PC3^{PSCA}$ feeder cell lines differently engineered to express IL-2, mIL-15-d, 4-1BB-L, IL-2-mIL-15d, IL-2-4-1 BBL, 4-1BBL-mIL-15d, and IL-2-4-1BBL-mIL-15d were tested by co-culture with isolated NK cells. For this, $2.5\times10^4$ feeder cells in 1 ml complete RPMI-1640 medium were cultivated in 24 well plates for 24h in a humidified incubator at 5% $CO_2$ and 37° C.

Figure 9:
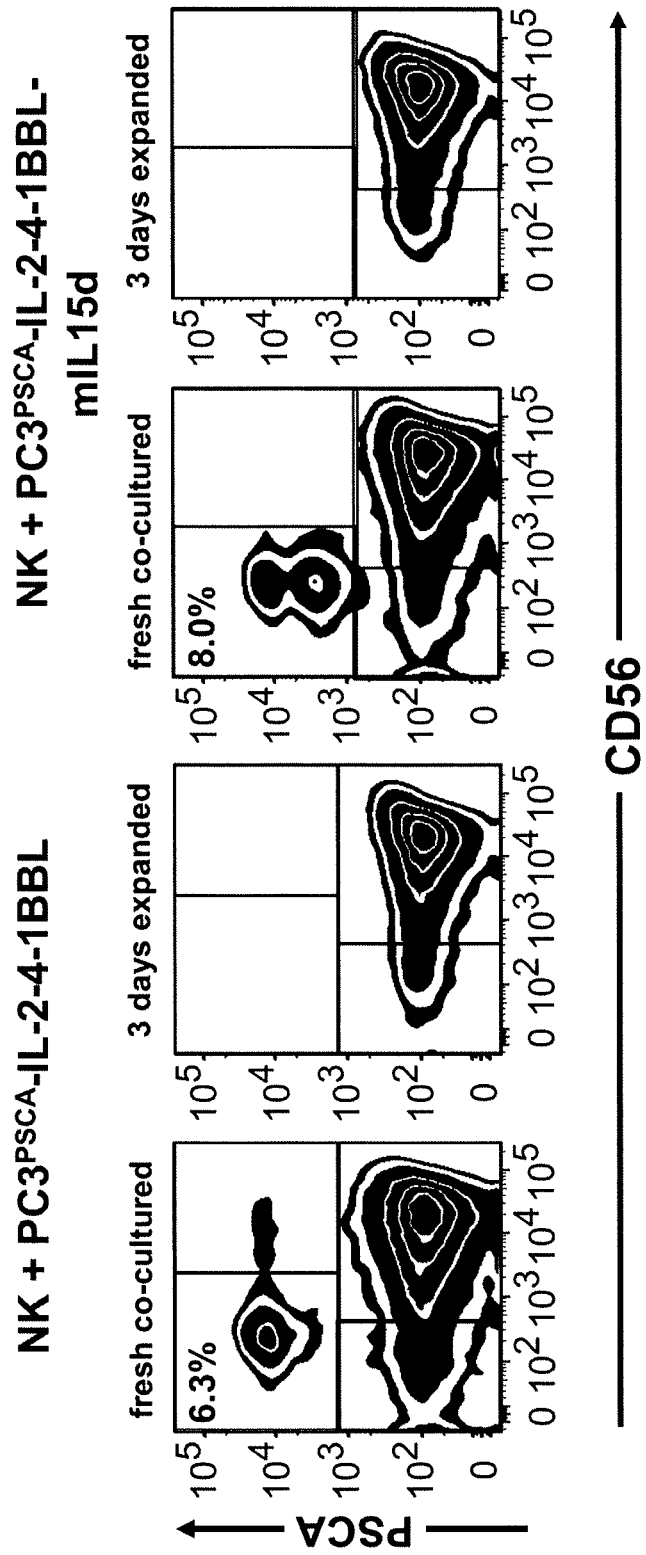
FIG. 9 demonstrates elimination of PSCA-positive PC3$^{PSCA}$-IL-2-4-1 BBL and PC3$^{PSCA}$-IL-2-4-1BBL-mIL-15d feeder cells during 3-day expansion of co-cultivated NK cells using FACS-assisted analysis of PSCA-marker expression on feeder cells.
Figure 10:
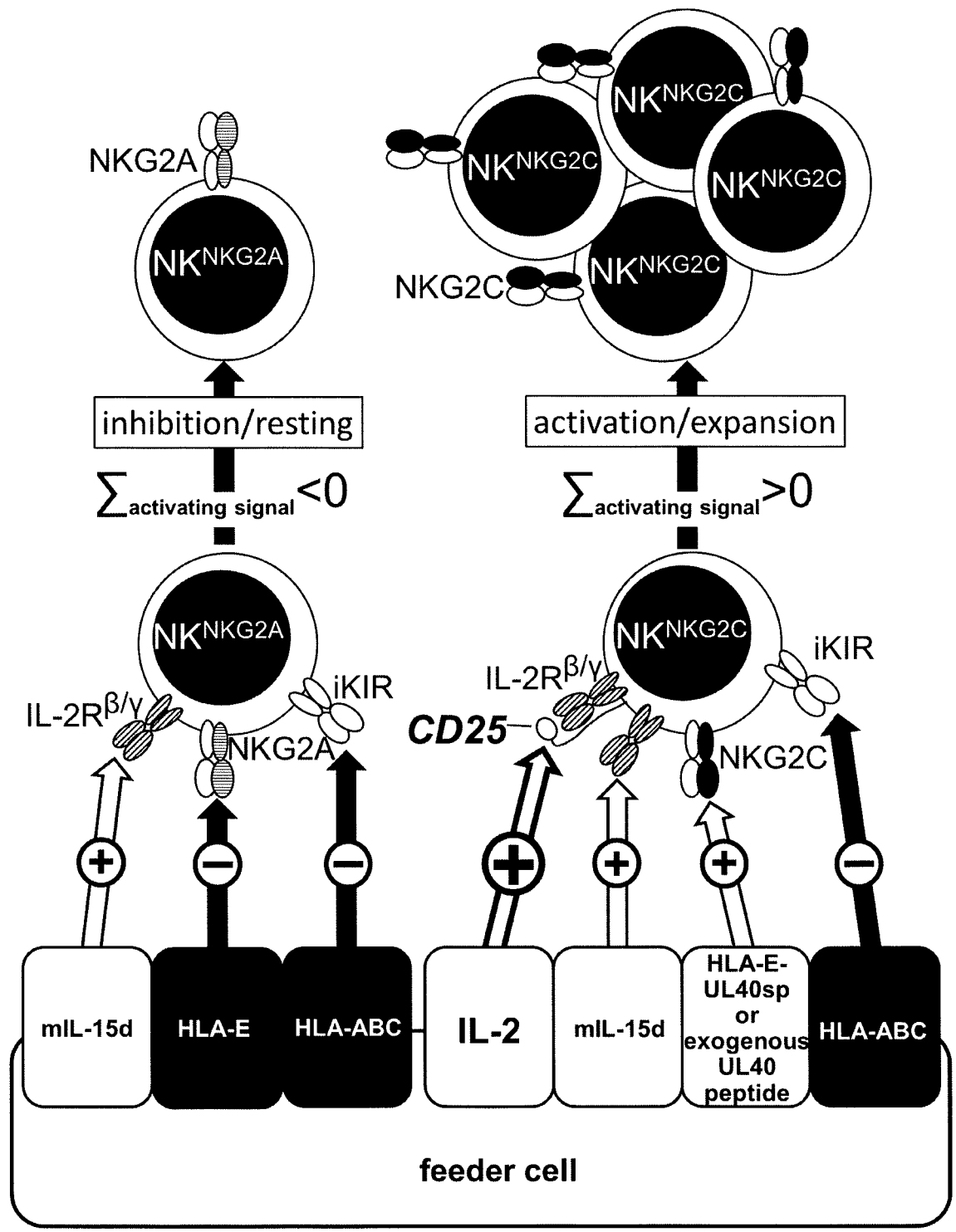
FIG. 10 depicts the scheme for activation and expansion of a NKG2C+-cell population out of the bulk cell NK population using activating peptides derived from HCMV UL40 loaded on HLA-E molecules of PC3$^{PSCA}$-IL-2 and PC3$^{PSCA}$-IL-2-mIL-15d feeder cells or using these feeder cells genetically engineered to express artificial β2microglobulin-HLA-E-protein (HLA-E-UL40sp) fused to an activating VMAPRTLIL and VMAPRTLFL peptide, respectively. At first, NK cells expressing NKG2A and/or and an inhibitory KIR and are devoid of NKG2C are considered to receive strong inhibitory signals through HLA-E and KIR-ligands, which hold them in a resting state. Yet, signaling through NKG2C is considered to induce CD25 expression leading to assembly of high affinity IL-2 receptor. Lastly, secreted IL-2 from feeder cells enables the selective expansion of NKG2C+ NK cells.

The next day the medium was substituted with 1-2 ml NK MACS medium (Miltenyi Biotec, Germany) supplemented with 2% NK MACS supplement (Miltenyi Biotec, Germany) and 5% human AB serum (c.c. pro, Germany). After 4-8 h $5\times10^5$ NK cells were added to the NK feeder cells. Every 3-4 days the plate was changed by resuspending the NK cells in new conditioned medium on newly seeded feeder cells. When using activation beads instead of feeder cells for expansion of NK cells, additionally 1000 U/ml PROLEUKIN S (Novartis, Germany) and 20 ng/ml IL-21 (Miltenyi Biotec, Germany) were added to the medium. To investigate the NK cell proliferation $1\times10^7$ fresh isolated NK cells were stained with CFSE (BioLegend, USA) according to the manufacturer's protocol. The CFSE-intensity of $1\times10^5$ NK cells was measured daily in the course of 6 days via flow cytometry (FIG. 4A). Total cell numbers of expanded NK cells were counted by staining cells with anti-CD56-APC (Miltenyi Biotec, Germany). IgG isotype controls were included by all measurements. Stained cells were measured by MACSQUANT Analyzer 10 flow cytometer (Miltenyi Biotec, Germany) and analyzed by FLOWJO version X.0.7 software (Tree Star, USA). As depicted in FIGS. 4A and B, unexpectedly only feeder cell lines genetically engineered to secret IL-2 were capable of expanding NK cells. In particular, this indicates that expression of mIL-15d in feeder cells alone cannot induce expansion but instead may provide survival signals. A strong expansion rate of NK cells, which was significantly greater than the expansion rate of NK cells activated with activation beads and concomitant exogenous cytokine treatment, were observed when using IL-2-4-1BBL-modified feeder cells, which was even more increased when using IL-2-4-1BBL-mIL-15d-modified feeder cells. (FIG. 4B, C). Noteworthy, staining of IL-2-4-1 BBL-modified feeder cells and IL-2-4-1BBL-mIL-15d-modified feeder cells with PSCA and staining of co-cultured NK cells with CD56 showed complete eradication of feeder cells after 3 days of NK expansion as depicted in FIG. 9. Staining of PSCA was accomplished using a biotinylated anti-PSCA scFv (scFv(AM1)-P-BAP, [67]) and secondary anti-biotin-VIOBLUE. CD56 on NK cells was detected using monoclonal anti CD56-APC.

Example 3: Surface Markers of Expanded NK Cells

Figure 5:
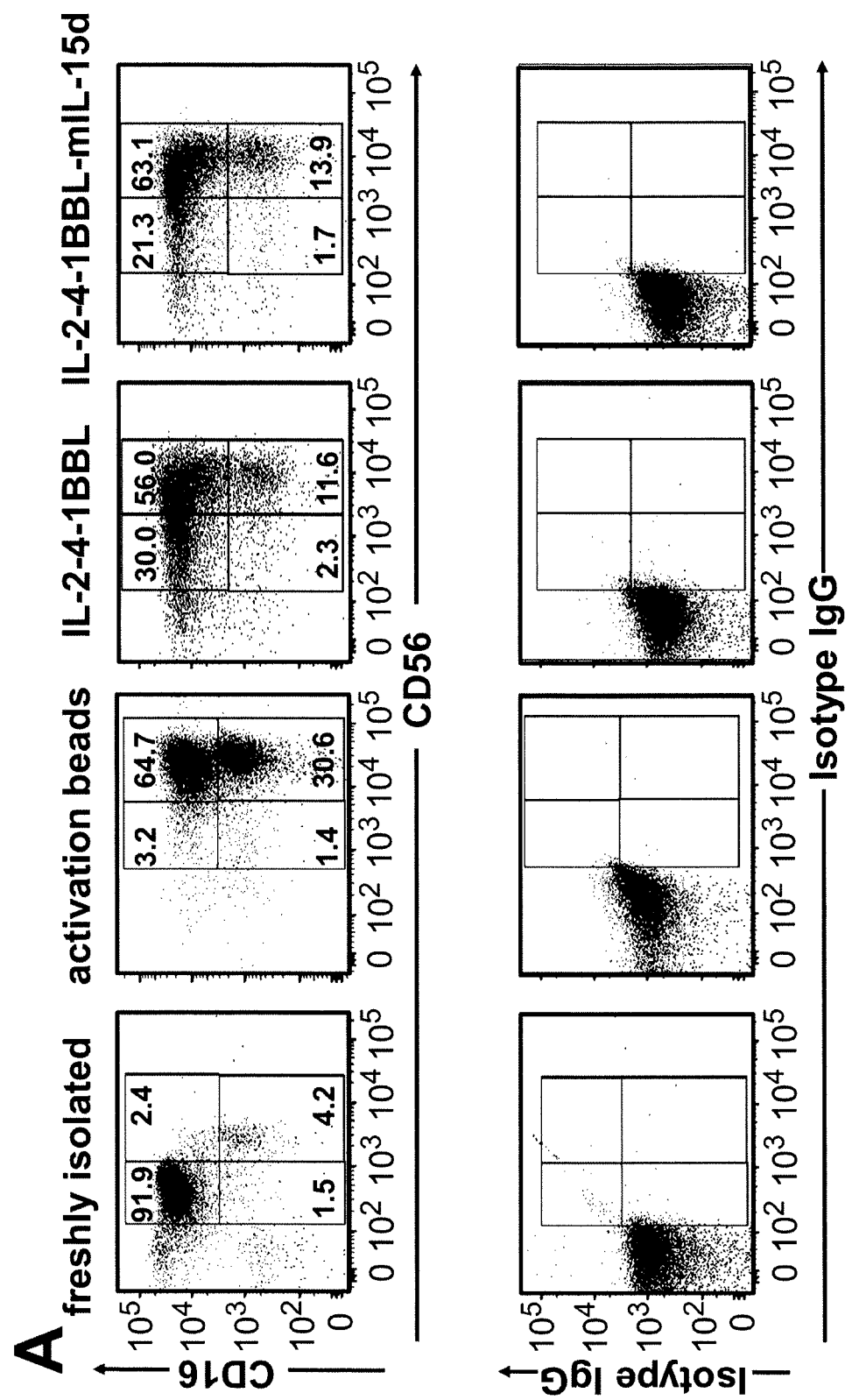
FIG. 5 shows investigation of NK cell subpopulations by flow cytometry. Freshly isolated NK cells, IL-2-4-1 BBL and IL-2-4-1 BBL-mIL15d modified feeder cell-expanded NK cells as well as activation bead-expanded NK cells 10 days after expansion from five healthy donors were analyzed. (A) Representative CD56/CD16 staining of NK cells from one donor is shown. NK cells stained with IgG isotype antibodies (bottom) served as a control. (B) Overview of the CD56bright/CD16+, CD56bright/CD16−, CD56dim/CD16+ and CD56dim/CD16− NK cell subpopulations before and 10 days after expansion. Displayed are mean values and standard derivation of two independent experiments using five donors.
Figure 5:
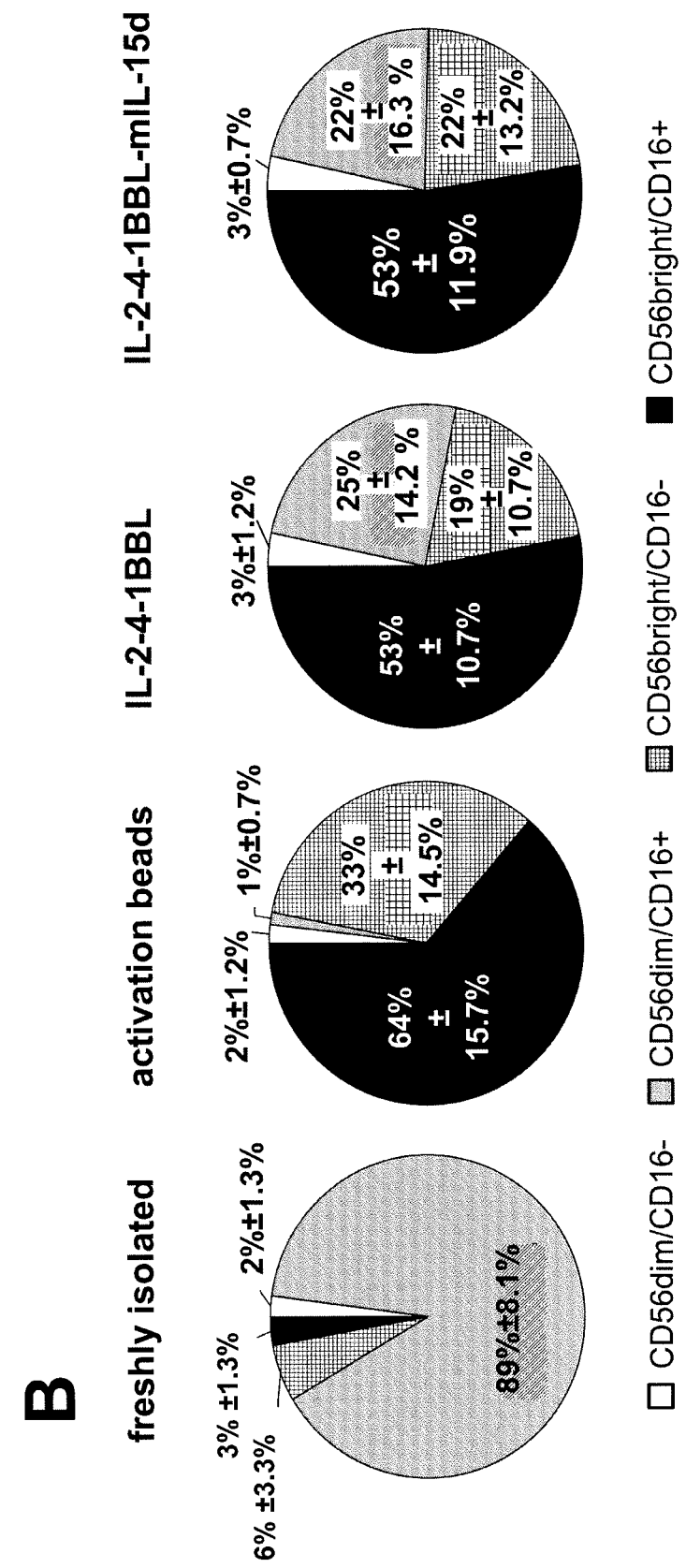

For phenotypic analysis $2\times10^5$ NK freshly isolated NK cells and NK cells expanded for 10 days with IL-2-4-1BBL-modified and IL-2-4-1BBL-mIL-15d-modified feeder cells were stained with anti-CD56-APC (Miltenyi Biotec, Germany) and anti-CD16-PE (eBioscience, Germany) and analyzed by flow cytometry. As depicted in FIG. 5, expansion of NK cells from five different donors using IL-2-4-1BBL-modified and IL-2-4-1BBL-mIL-15d-modified feeder cells, unexpectedly resulted in the outgrowth of three major NK subpopulations, namely CD56bright/CD16high, CD56dim/CD16high and CD56bright/CD16- cells, which in both settings comprise approximately 97% of the NK cells. CD56dim/CD16high NK cells have a high cytotoxic potential whereas CD56bright/CD16-NK cells have been described as immunomodulatory NK cells [35]. In contrast, expansion of NK cells using anti-CD2/NKp46-labeled activation beads resulted in the expansion of only CD56bright/CD16high NK cells and CD56bright/CD16- cells, whereas a CD56dim/CD16high NK cell fractions were barely seen (FIG. 5A, B).

Figure 7:
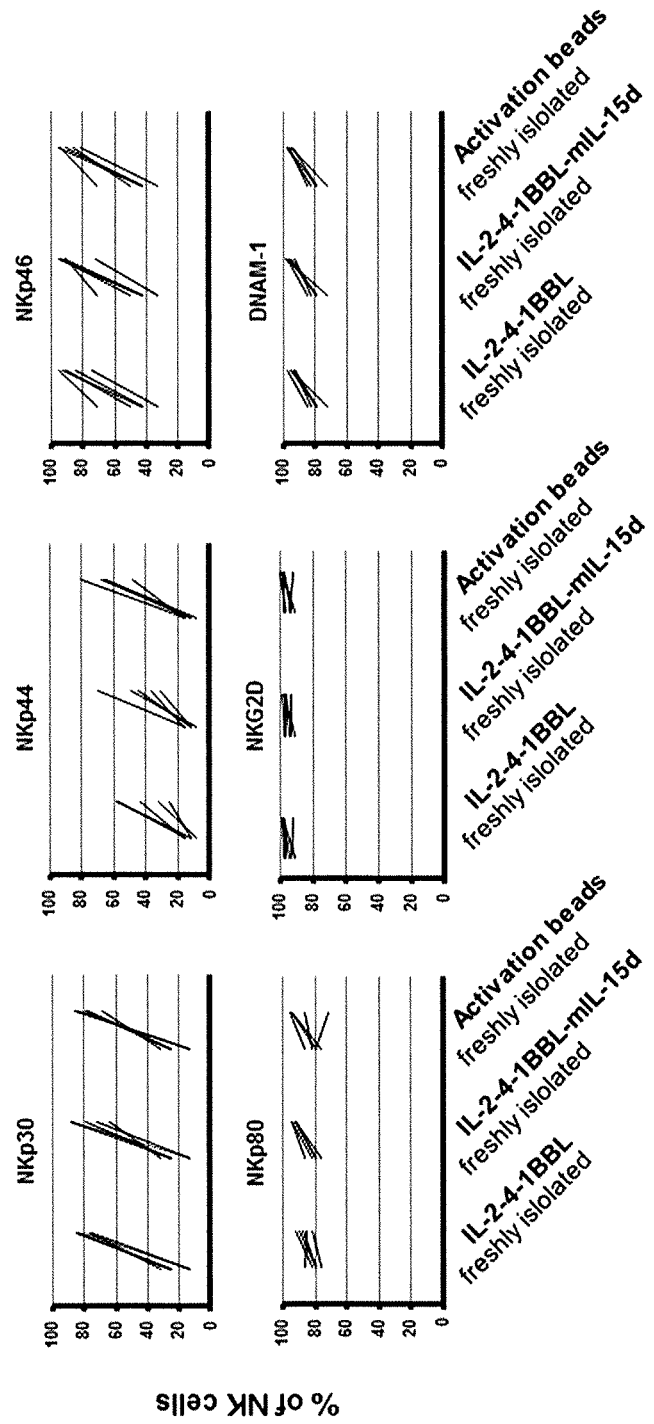
FIG. 7 shows NK cell surface marker expression of isolated NK cells expanded with IL-2-4-1 BBL-, and IL-2-4-1 BBL-mIL-15d feeder cells. Anti-CD2/NKp46-activation beads-expanded NK cells were included in the experiments. Results were obtained from five healthy donors 10 days after start of the expansions. Depicted are expression levels of activating and co-activating receptors (A), inhibitory and co-inhibitory receptors (B) as well as immune checkpoint and activation markers (C). Displayed are mean values of three independent experiments for each donor.
Figure 7:
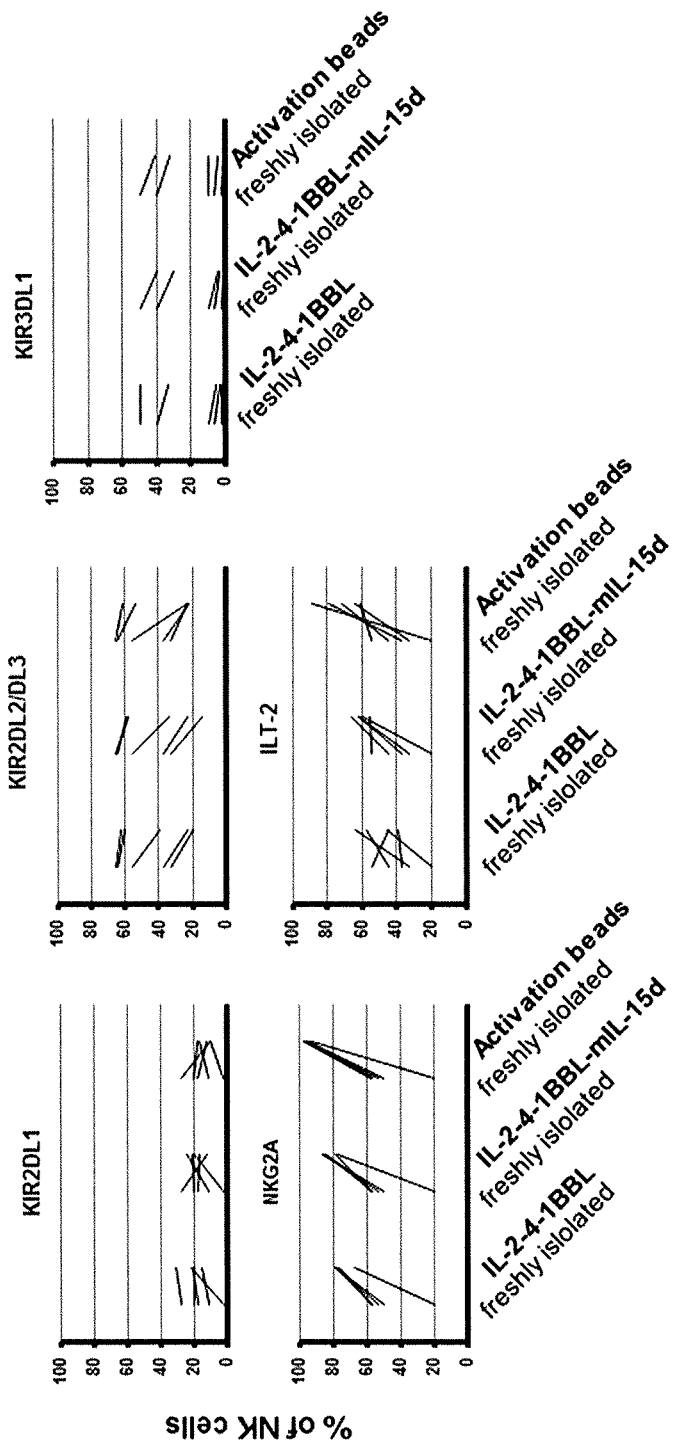
Figure 7:
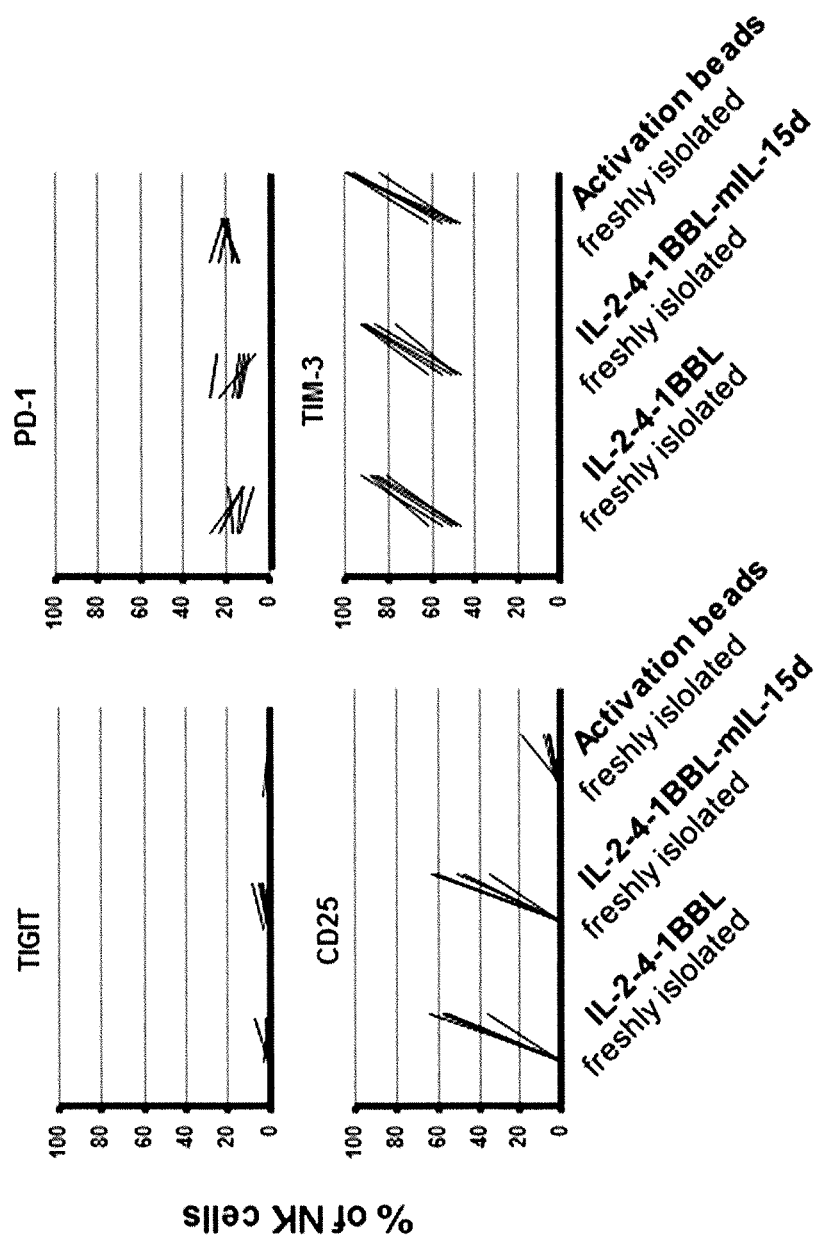

Further staining of expanded NK cells and of freshly isolated NK cells from peripheral blood, respectively, included anti-CD337(NKp30)-PE, anti-CD336(NKp44)-PE, anti-NKp46-PE, anti-NKp80-PE, anti-CD226(DNAM-1)-PE (Miltenyi Biotec, Germany), anti-CD314 (NKG2D), anti-CD158a-PE (BD Pharmingen, USA), anti-CD158b (KIR2DL2/DL3)-PE, anti-CD158e(KIR3DL1)-PE, anti-CD159a(NKG2A)-APC, anti-CD85j(ILT2)-APC (Miltenyi Biotec, Germany), anti-TIM-3-PE, anti-CD279(PD1)-PE, anti-TIGIT-Biotin plus anti-Biotin-PE (Miltenyi Biotec, Germany), and anti-CD25-APC (Miltenyi Biotec, Germany) for the high affinity alpha-chain of the IL-2Rα/β/γ. All staining procedures were performed according to the instructions of the provider. Isotype controls were included in all measurements. Stained cells were examined by a MACSQUANT 10 flow cytometer (Miltenyi Biotec, Germany) and analyzed by FLOWJO software version X.0.7 (Tree Star, USA). Irrespective of the used expansion method, activating and co-activating receptors including NKp30, NKp44, NKp46, NKp80, NKG2C and DNAM-1 were up-regulated in expanded NK cells (FIG. 7A). However, no dissimilarities between the differentially expanded NK cells, with the exception of NKp44, which was slightly broader expressed after expansion with activation beads, were detected. NK cells from all expansion groups contained NKG2D NK cell fractions >90% which did not significantly differ to those observed in freshly isolated NK cells (FIG. 7A). The fraction of NK cells expressing KIR2DL2/L3/S2 decreased in all expansion groups (FIG. 7B). In accordance with KIR genotyping, no signals for KIR3DL1 were observed for NK cells from donor 4. The frequency of KIR3DL1-positive NK cells from all other donors were slightly reduced in all expansion groups. The frequency of KIR2DL1/S1/S4-positive NK cells in all groups of differentially expanded NK cells remained in the mean below 25%. Yet, expansion using feeder cells revealed slight donor-dependent increases in relative amounts of KIR2DL1/S1/S4-positive NK cells which might be related to differential compositions of KIR2DL1/S1/S4 alleles. In particular, the percentage of KIR2DL1/S1/S4-positive NK cells from donor 1, which lack inhibitory KIR2DL1 alleles and instead contains KIR2DS1, moderately increased during expansion with feeder cells. Yet, the fraction of CD94/NKG2A-positive cells as well as of NK cells expressing the co-inhibitory ILT2 receptor was strongly increased in all groups of expanded NK cells when compared to corresponding freshly isolated NK cells (FIG. 7B). Activation beads-expanded NK cells showed a significant higher frequency of CD94/NKG2A and partially of ILT2-positive cells when compared to NK cells expanded by feeder cells (FIG. 7B). Additional analysis of the fraction of cells expressing TIGIT and PD-1 associated with exhaustion of lymphocytes revealed unexpected low frequencies of PD-1- and TIGIT-positive cells in all groups of expanded NK cells (FIG. 7C).

In contrast, the relative number of TIM-3-positive cells, which is associated with cytokine induced activation and maturation of NK cells, was strongly amplified after expansion of NK cells using feeder cells or activation beads. Surprisingly, in feeder cell-expanded NK cells from different donors, 35% to 64% of NK cells were found to express the alpha chain (CD25) for high affinity IL-2 receptor (CD25). Noteworthy, no such strong increase in CD25-positive cells was observed in NK cells which were expanded by the use of activation beads (FIG. 7C).

Altogether, PC3$^{PSCA}$-IL2-4-1BBL and PC3$^{PSCA}$-IL2-4-1BBL-mIL15 expanded NK cells showed a promising upregulation of CD25, indicating a shift to high affinity IL-2 receptor as well as unaffected levels of the immune checkpoint molecules PD1 and TIGIT.

Figure 6:
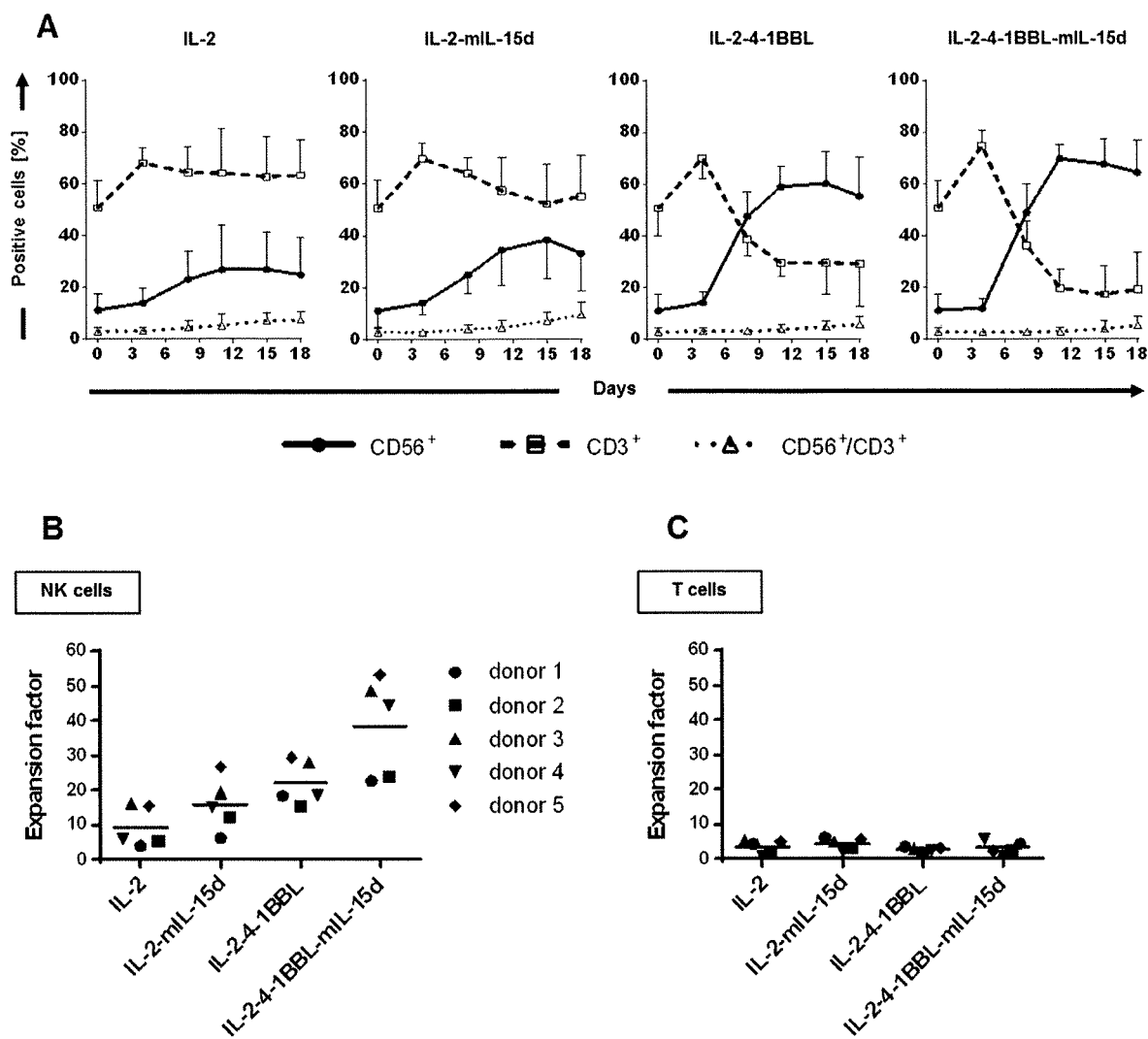
FIG. 6 shows expansion of NK cell fractions from PBMC samples using IL-2-secreting PC3$^{PSCA}$-derived feeder cell lines. (A) Percentage of NK cells (CD56+/CD3−), T cells (CD56−/CD3+) and NKT cells (CD56+/CD3+) relative to the total number of leucocytes (gate on living cells) were revealed by flow cytometry over 18 days of expansion using anti-CD56 and anti-CD3 antibodies. Results are shown as mean+/−SD of PBMCs from five different donors. (B) Graph depicting the maximal expansion factors of primary NK cells and means. Maximal expansion factor is calculated via the maximum cell count within the cultivation of 18 days, relative to the cell count at the start of the experiment (day 0). Note, that only feeder cell lines genetically modified with IL-2 plus 4-1BBL and modified with IL-2, 4-1BBL plus mIL-15d, respectively, stimulate a strong and selective expansion of NK cells without concomitant expansion of T cells (see (C)).

Example 4: Selective Expansion of NK Cells Out of Peripheral Blood Mononuclear Cells (PBMCs) Using IL-2-Secreting Feeder Cell Lines Human PBMCs were isolated from fresh blood of five healthy donors by BIOCOLL gradient centrifugation (Biochrom, Germany). For investigating selective expansion of NK cells from PBMCs, PBMCs were co-cultured with PC$^{PSCA}$-derived artificial NK feeder cell lines. For this, $2.5 \times 10^4$ feeder cells in 1 ml complete RPMI-1640 medium were cultivated in 24 well plates for 24h in a humidified incubator at 5% $CO_2$ and 37° C. The next day the medium was substituted with 1-2 ml NK MACS medium (Miltenyi Biotec, Germany) supplemented with 2% NK MACS supplement (Miltenyi Biotec, Germany) and 5% human AB serum (c.c. pro, Germany). After 4-8 h $5 \times 10^6$ PBMCs were added to the NK feeder cells. Every 3-4 days the plate was changed by resuspending the PBMCs in new conditioned medium on newly seeded feeder cells. When using activation beads instead of feeder cells for expansion of NK cells, additionally 1000 U/ml PROLEUKIN S (Novartis, Germany) and 20 ng/ml IL-21 (Miltenyi Biotec, Germany) were added to the medium. Cell numbers and percentages of NK cell, T cell and NKT cell fractions during PBMC expansion was analyzed by staining of $2 \times 10^5$ PBMCs with anti-CD56-APC and anti-CD3-PE (Miltenyi Biotec, Germany) and subsequent analysis using a MACSQUANT Analyzer 10 flow cytometer and FLOWJO version X.0.7 software. As depicted in FIG. 6A, selective NK cell expansion was achieved when using PC3$^{PSCA}$-IL-$_2$-4-1BBL and PC3$^{PSCA}$-IL-2-4-1BBL-mIL-15d cells. Best expansion rates of NK cells were seen when using the PC3$^{PSCA}$-IL-2-4-1 BBL-mIL-15d feeder cell line (FIG. 6B). As shown in FIG. 6C all feeder cell lines failed to promote expansion of T cells.

Example 5: Cytotoxicity and Tolerance to Self of Expanded NK Cells

The cytotoxicity NK cells, expanded for 3 and 4 weeks, respectively, from four different donors toward K562 cells (devoid of protective HLA-ABC and HLA-E expression) was tested by chromium-release assays. Briefly, $2 \times 10^6$ target cells were labeled with 1.5 MBq sodium $^{51}$chromate (HARTMANN ANALYTIC, Germany) and incubated at 37° C. and 5% CO2. After 1 h, cells were washed with PBS and seeded as triplicates in a round bottom 96-well plate (2×103 cells per well). Expanded NK cells were added to labeled target cells at effector to target ratios of 7.5:1 and 15:1. After 4 h of co-cultivation, 25 µl of cell supernatant was mixed with 150 µl of scintillation solution ULTIMA GOLD (PerkinElmer, USA) in a 96-well plate by shacking for 3×5 min at room temperature. The chromium release was measured using a WALLACE 1450 MICROBETA TRILUX Liquid Scintillation and Luminescence Counter (PerkinElmer, USA). Maximal releases were measured by treating target cells with 5% TRITON X-100 (Serva, Germany) and minimum releases by cultivation of target cells with medium alone.

Figure 8:
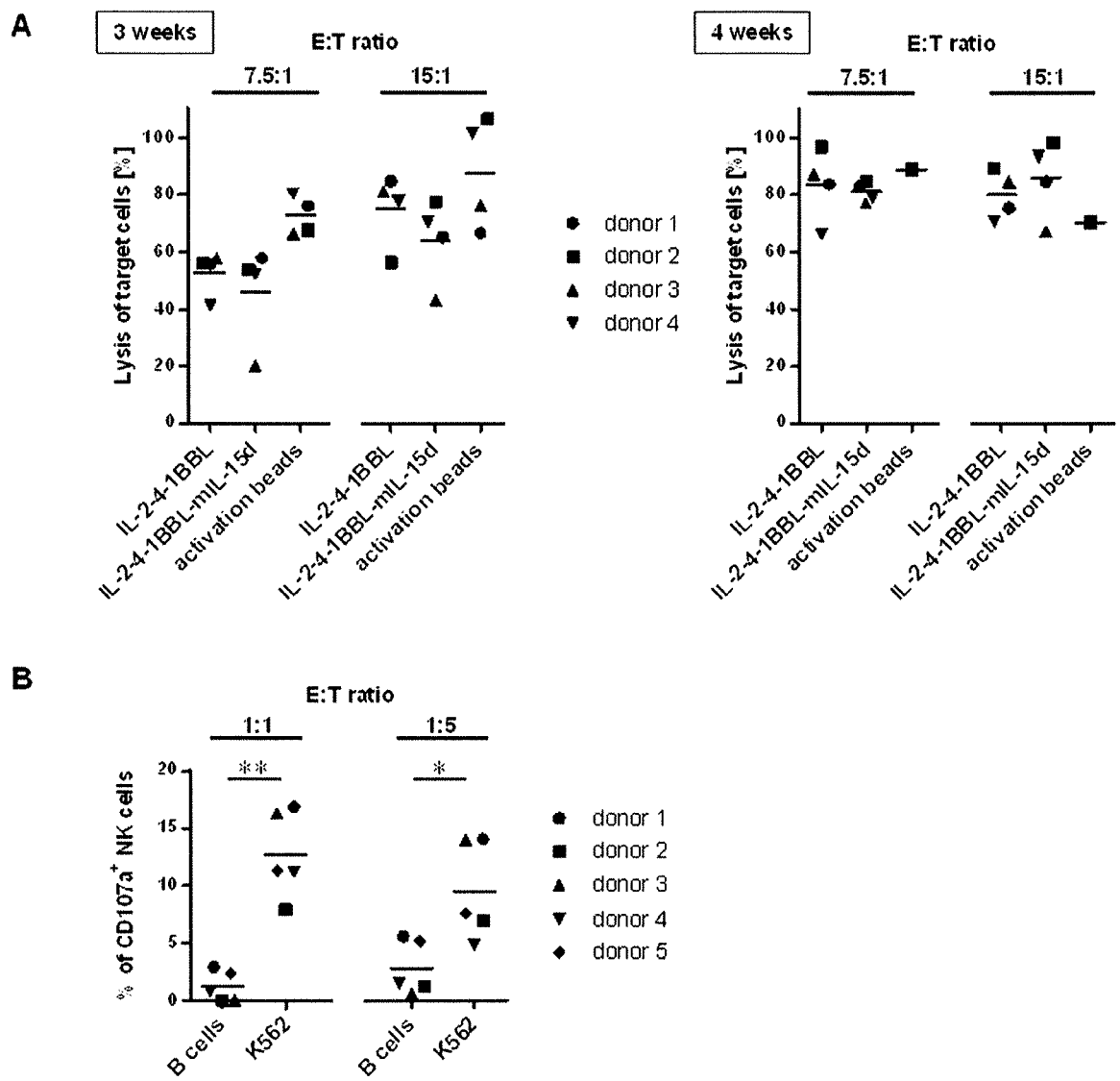
FIG. 8 shows that NK cells are tolerant for self, are not hyper-activated but can be hyper-activated when treated with exogenous IL-2, and are able to develop cytotoxic responses upon missing self-recognition as well as after induction of ADCC. (A) PC3$^{PSCA}$-IL-2-4-1 BBL, PC3PSCA-IL-2-4-1BBL-mIL-15d feeder cell- or activation bead-expanded NK cells from four healthy donors 3 weeks and 4 weeks after isolation were co-cultured with $^{51}$chromium-loaded K562 cells at different effector to target (E/T) ratios for 4 h. The mean of specific cell lysis of triplets of one representative chrome release assay is shown. In contrast to NK cells expanded using feeder cells, the viability of NK cells expanded by the use of activation beads including continuous exogenous cytokine support decreased after 4 weeks. Therefore, only expanded NK cells from one donor could be included for testing cytotoxicity against K562 targets. (B) shows cytotoxicity of expanded NK cells against autologous cells analyzed by CD107a degranulation assay. PC3PSCA-IL-2-4-1BBL-mIL-15d feeder cell-expanded NK cells from five healthy donors were co-cultivated with autologous B cells or K562 cells (positive control) at indicated effector to target (E/T) ratios for 4 h. NK cells in medium alone served as an internal control. Percentage of CD107a positive NK cells in medium alone was subtracted from percentage of CD107a positive NK cells co-cultivated with B cells or K562 (*p<0.05, **p<0.01). (C) depicts cytotoxicity of expanded NK cells from four different donors when confronted with allogeneic primary GBM cells from patient HT18223 or patient HT18199. Cytotoxicity of NK cells was analyzed using chromium-release assay at an effector to target ratio of 5:1. All donors contained licensed NK cells for C1 and non-licensed NK cells for Bw4 indicated by grey boxes. Additionally, donors 2 and 5 contained licensed NK cells for C2, which missed its C2 ligand in HT18199 cells indicated by black boxes. Donor 3 contained non-licensed KIR2DL1-NK cells missing its C2 ligand in HT18199 cells indicated by a grey box. Note the increased lytic cytotoxicity of activation beads-expanded NK cells whereas NK cells expanded by PC3PSCA-IL-2-4-1BBL-mIL-15d remained unresponsive (*p<0.05). (D) Cytotoxicity towards HT18223 and HT18199 GBM cells was induced by hyper-activation of expanded NK cells with 50 IU/ml rhIL-2 (*p<0.05). (E) shows expression of HLA-ABC and of EGFR on GBM target cells measured by flow cytometry (filled areas). EGFR surface expression was assessed using cetuximab and secondary APC-conjugated antibody. Cells stained with isotype antibody (open areas) served as a control. (F) depicts induction of ADCC of NK cells towards cetuximab-marked primary GBM cells. Cytotoxicity was assessed using chromium-release assay at an effector to target ratio of 5:1. Note, that the strength of the ADCC is directly correlated to amount of EGFR surface expression on target cells (mean±SD; *p<0.05, ns; not significant).
Figure 8:
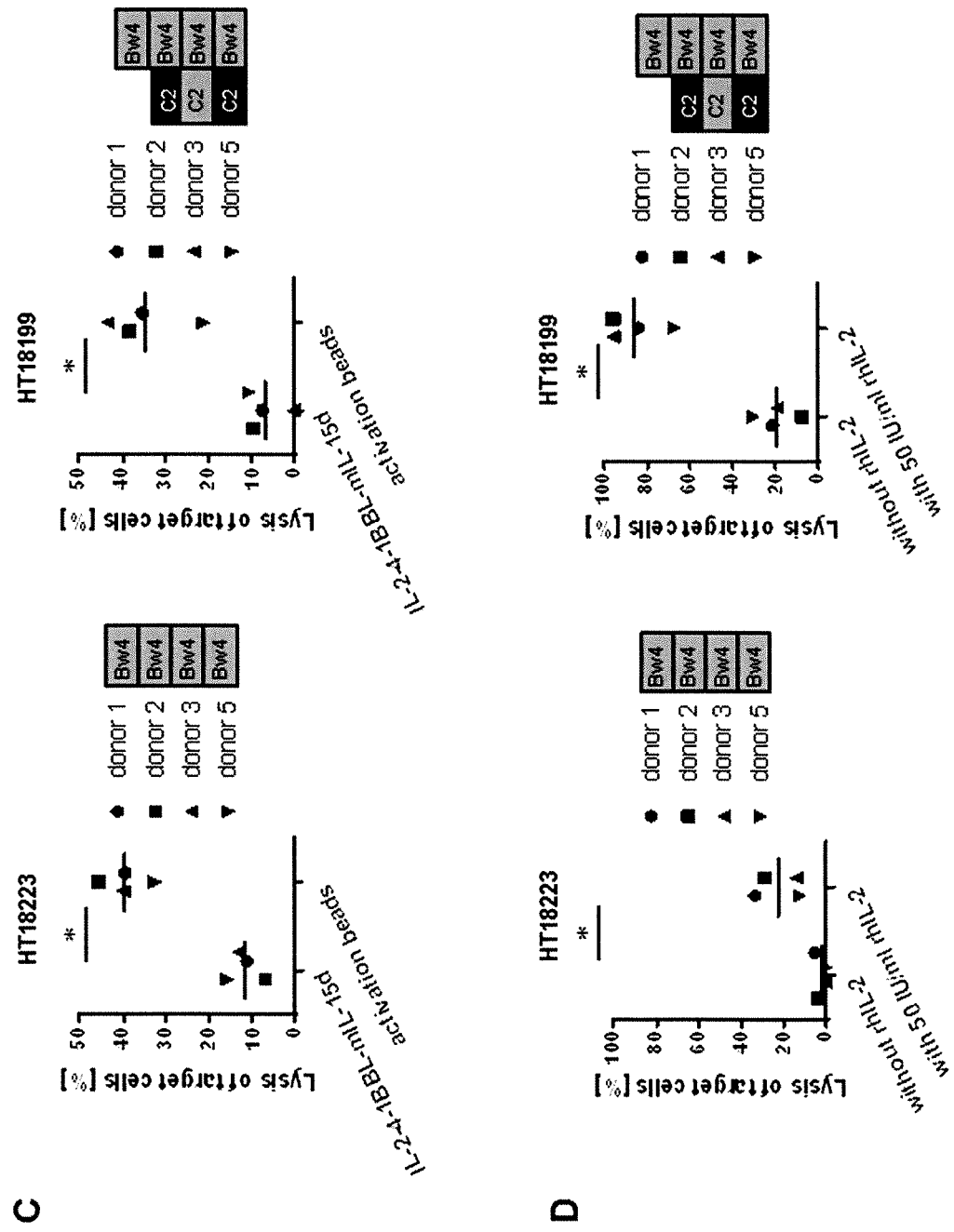
Figure 8:
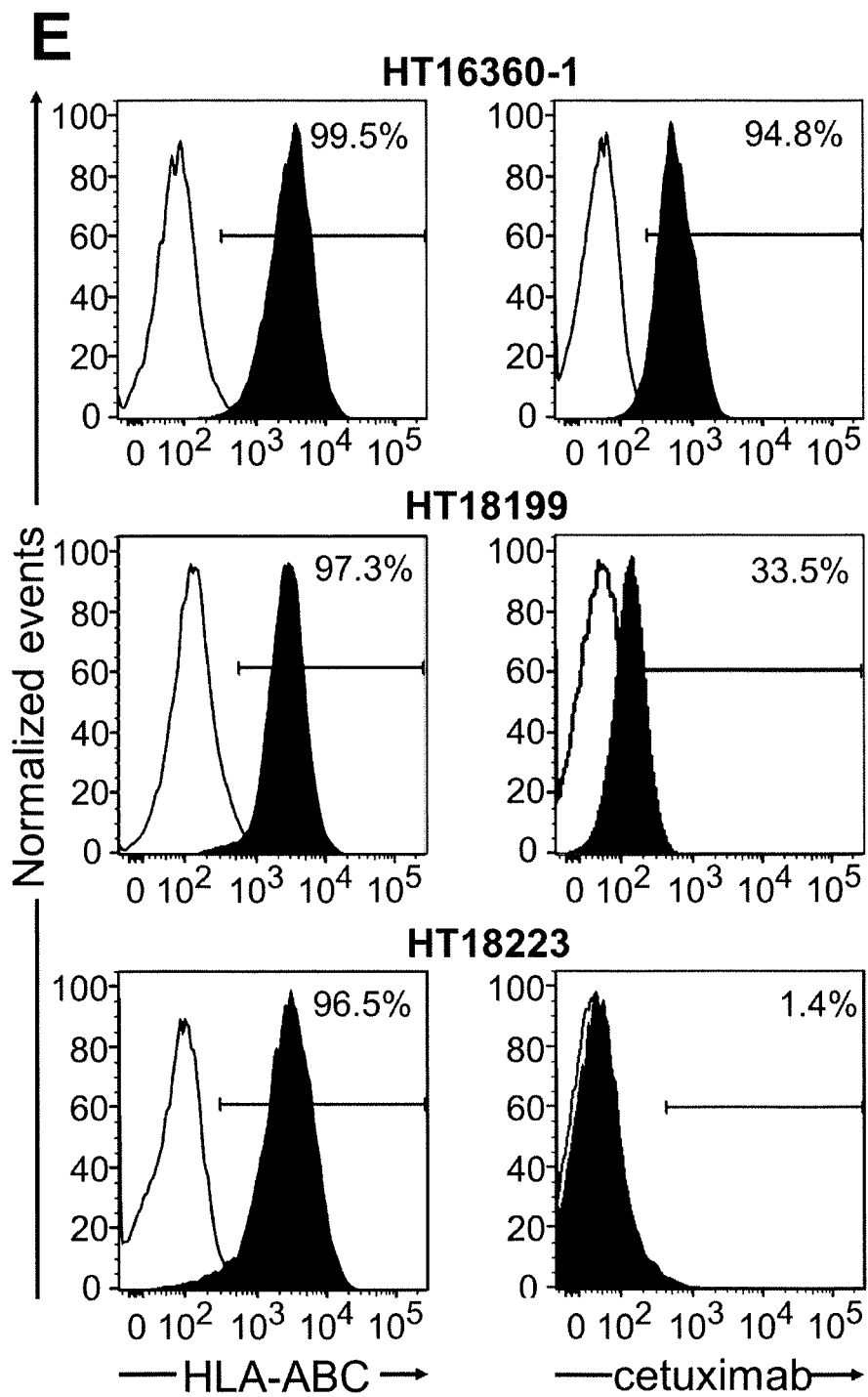
Figure 8:
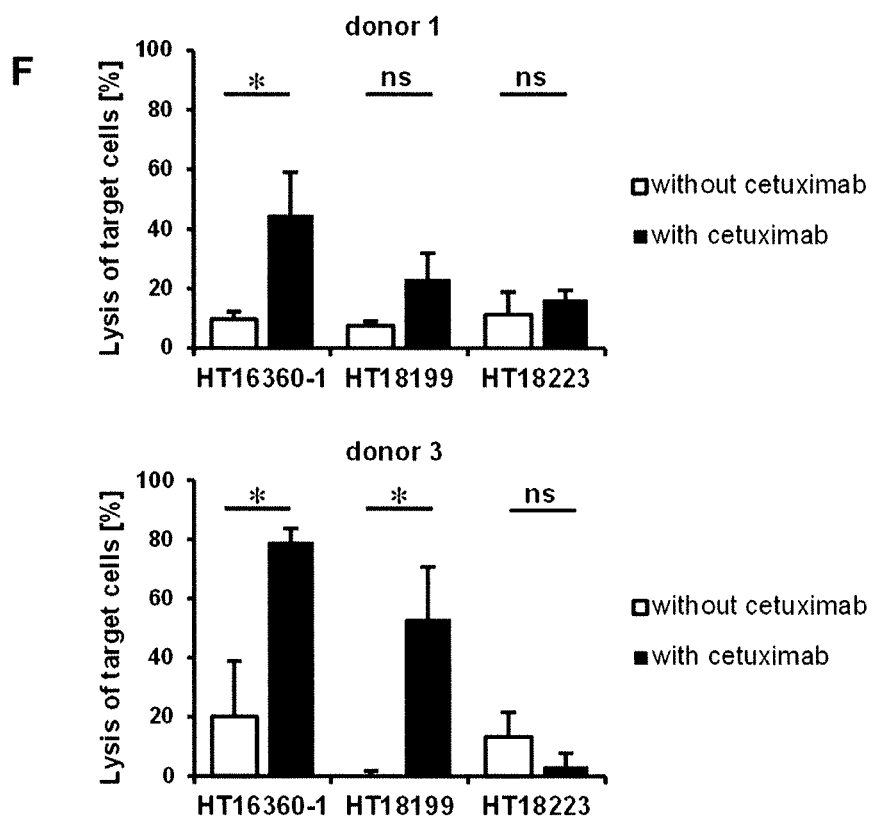

Percentage of specific lysis was calculated using the standard formula: 100 ×(cpm release target cells–cpm minimum release)/(cpm maximum release–cpm minimum release). As depicted in FIG. 8A, NK cells either expanded by feeder cells or expanded by activation beads and exogenous IL-2/IL-21 were capable of killing K562 target cells.

Self-tolerance of NK cells from five healthy donors expanded for 24 days using PC3$^{PSCA}$-IL2-4-1 BBL-mIL15 feeder cells and activation beads plus exogenous IL-2/IL-21, respectively, were analyzed by CD107a degranulation assay. Therefore, NK cells were co-cultivated with fresh isolated autologous B cells in an effector to target ratio of 1:1 and 1:5 in 200 µl complete NK MACS medium in a V-bottom 96-well plate. NK cells in medium alone served as negative control. NK-sensitive K562 cells were used as positive control. After 1 h of co-cultivation, 2 mM monensin (dilution 1:40, Sigma-Aldrich, Germany) and anti-CD107a (LAMP-1)-VIOBLUE (Miltenyi Biotec, Germany) were added to the wells and incubated for additional 3 h. Afterwards, sell-surface staining was performed against CD56 using the antibody mentioned in the previous section. IgG isotype controls were included. As shown in FIG. 8B the CD56-positive NK cells expanded by PC3$^{P}$SCA-IL2-4-1BBL-mIL15 feeder cells remained unresponsive against autologous B cells but show strong degranulation (CD107a-staining) when confronted with K562 erythroleukemia cells.

Cytotoxicity of the feeder cell-expanded NK cells towards allogeneic HT18223 and HT18199 primary glioblastoma cells was assessed using chromium-release assay (FIG. 8C). Calculated KIR:KIR-ligand mismatches of HLA/KIR-genotyped NK cells to HLA-genotyped HT18223 and HT18199 GBM cells and licensing status are depicted as inlets in FIG. 8C. All target cells expressed C1 ligand for KIR2DL2/3 expressed by all donors. When expanded NK cells from four donors, having a KIR:KIR-ligand match based upon analysis of HLA alleles, yet having non-licensed NK cells missing Bw4 on target cells, were confronted to HT18223 GBM cells no substantial cytotoxic response was observed. In contrast, NK cells which were expanded by activation beads, yet displayed similar expression of activating and inhibitory NK cell receptors as feeder cell-expanded NK cells (see FIG. 7) robustly killed HT18233 cells indicating a hyper-activated state. A similar outcome was obtained when using HT18199 target cells (FIG. 8C). In this experiment feeder cell-expanded NK cells from donor 1, having non-licensed KIR3DL1 which misses a cognate ligand on the target cells, remained unresponsive. NK cells from donor 3 containing non-licensed KIR3DL1 and containing non-licensed KIR2DL1, both missing their cognate ligands on target cells, also remained unresponsive. Unexpectedly, feeder cell-expanded NK cells from donors 2 and 4, which both contained non-licensed Bw4 missing its cognate ligand in the target cells and additionally exhibited a C2-mismatch in the target cell direction also remained non-responsive to HT18199 GBM cells. Since the inhibitory receptors NKG2A and ILT2 were expressed in 82.5% (77.8-86.2%) and in 61.2% (55.4-66.6%) of polyclonal feeder cell-expanded NK cells (see FIG. 7), respectively, it can be anticipated that the expanded NK cell product from donors 2 and 4 is devoid of potentially alloreactive CD94/NKG2A-negative and ILT2-negative single KIR2DL1-positive NK cells. Surprisingly, cytotoxicity towards HT18223 and HT18199 GBM cells was unleashed by pre-treatment of feeder cell-expanded NK cells with 50 IU/ml rhIL-2 (FIG. 8D).

The antibody dependent cellular cytotoxicity of the expanded NK cells from donors 1 and 3 was tested using HLA-ABC-positive primary glioblastoma cell lines HT16360-1, HT18199 and HT18223. HLA-genotyping of these cells revealed KIR-Ligand/KIR matches with the exception of non-licensed Bw4 in the GvH direction. Staining of these cancer cells with the therapeutic antibody cetuximab, which is specific for the epidermal growth factor receptor (EGFR) and secondary anti-human IgG-APC showed different expression levels of EGFR (high, low expression and not detectable) (FIG. 8E). Differentially expanded NK cells were co-cultured with or without cetuximab (75 µg/ml) and induction of ADCC was investigated using a 20h standard chromium-release assay. As shown in FIG. 8F the NK cells expanded by IL-2-4-1BBL- and IL-2-4-1BBL-mIL-15d-expressing feeder cells responded in direct correlation to the different levels of cetuximab bound on target cells.

Altogether, these examples show the prospect for educated NK cells generated in this manner for adoptive cell transfer. Said NK cells should be less hazardous in inducing damage of stressed normal tissues and could prove efficacious when properly activated, both in the autologous and allogeneic setting.

Example 6: Selective Expansion of NKG2C+NK Subpopulation Using Peptide-Loaded or HLA-E-UL40sp-Modified PC3$^{PSCA}$-IL-2 and PC3$^{PSCA}$-IL-2-4-mIL-15d Feeder Cells Conceptually, for expansion of NKG2C+NK cells to clinical relevant numbers it is essential to use a cell subset with proliferative capacity, namely CD56bright NK cells, which represent 5-10% of peripheral blood NK cells and which might have the capacity to develop into NKG2A+ and into NKG2C+NK cell subsets. We demonstrated only suboptimal growth of NK cells when using the EBV-negative PC3-derived feeder cell line secreting low amounts of IL-2 and optionally genetically modified to express a membrane-bound IL-15. Using these feeder cells, we hypothesized that combined inhibiting signals for KIRs and NKG2A should selectively limit proliferation of NK cells characterized by KIR+ and NKG2A+status of surface markers. Vice versa, engaging a stochastically expressed NKG2C during differentiation of NK cells originating from the non-differentiated CD56bright/NKG2A-/NKG2C- subset should result in activating signals overcoming the dominance of the combined inhibitory signaling and should together with low doses of IL-2 result in selective proliferation NKG2C+NK cell subsets. In case of an expressed activating KIR on NK cell subsets, we hypothesized that lack of CD25 expression together with the lower binding affinity of activating KIRs to cognate HLA-ligand as well as an concomitant expression of an simultaneously-expressed inhibitory KIR keep such NK subsets cells in a resting state.

For activation and selective expansion of NKG2C+NK cell subsets, HLA-E molecules of the PC3$^{PSCA}$-2 and PC3$^{PSCA}$-IL-2-mIL-15d feeder cells were exogenously loaded with chemically synthetized activating peptides (50 µM, JPT Peptide Technologies GmbH, Berlin, Germany) VMAPRTLLL (SEQ ID NO: 1) and VMAPRTLFL (SEQ ID NO: 2) for 4h. As control, untreated feeder cells were included. Freshly isolated untouched NK cells were immediately co-cultured with peptide-loaded feeder cells. Every 3-4 days the NK cells were passaged using on feeder cell lines freshly loaded with ↓ peptides and cell samples were stained for CD56, NKG2C and NKG2A (all antibodies from Miltenyi Biotec, Germany) and analyzed using a MACSQUANT Analyzer 10 flow cytometer (Miltenyi Biotec, Germany). After gating on living and CD56+cells the relative proportion of stained NKG2C and NKG2A NK cells was determined using FLOWJO version X.0.7 software. Unexpectedly, the peptide-loaded $PC3^{PSCA}$-$_2$ and $PC3^{PSCA}$-IL-2-mIL-15d feeder cells gradually induced the outgrowth of NKG2C+NK cells from bulk NK cell preparations from different HCMV seropositive donors having NKG2C+NK cell frequencies between 5-12%. Surprisingly, NKG2C cells developed from double positive NGK2A+/NKG2C+cells. After 14 days of expansion NKG2A+/NKG2C- and NKG2A+/NKG2C+NK cell subsets were still detected using specific antibodies for NKG2A and NKG2C (FIG. 11A). All $PC3^{PSCA}$-2 and $PC3^{PSCA}$-IL-2-mIL-15d feeder cells either loaded with VMAPRTLFL (SEQ ID NO: 2) or VMAPRTLLL (SEQ ID NO: 1) favored outgrowth of NK cells expressing NKG2C with mean expansions factors between 130-fold and 190-fold when compared to relative NKG2C+cell counts at day 0 (FIG. 11B). $PC3^{PSCA}$-2 and $PC3^{PSCA}$-IL-2-mIL-15d feeder cells without peptide-loading did not promote selective outgrowth of NKG2C+NK cells (FIG. 11B). This result additionally shows that $PC3^{PSCA}$IL-$_2$ and $PC3^{PSCA}$-IL-2-mIL-15d feeder cells might be a useful tool for identifying HLA-E-associated activating peptides derived from different sources such as tumors and pathogens.

Figure 12:
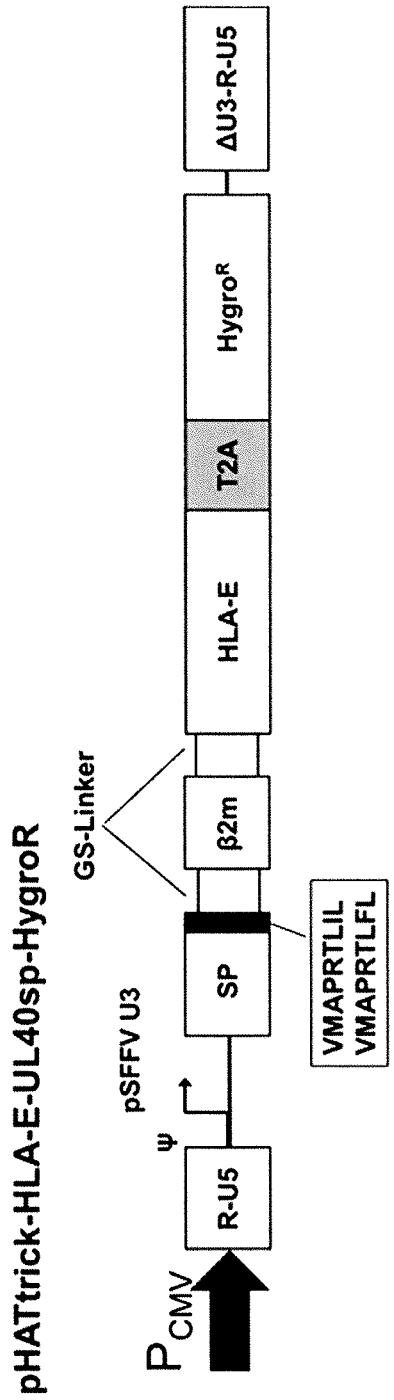
FIG. 12 (A) depicts the schematic drawing of the HLA-E-UL40sp constructs, HLA-E-UL40-VMPARTLIL (SEQ ID NO: 5) contains the VMPARTLIL (SEQ ID NO: 3) peptide from HCMV strain AD169, which is identical to a nonamer peptide derived from signal peptides from various HLA-C alleles (HLA-Cw*01, -Cw*03, -Cw*04, -Cw*05, -Cw*06, -Cw*0801-03, -Cw*12, -Cw*14, -Cw*16, and -Cw*1702) and HLA-E-UL40-VMPARTLFL (SEQ ID NO: 6) contains the VMPARTLFL (SEQ ID NO: 2) peptide from HCMV isolate BE/1/2010 (GenBank: KP745677.1) which is identical to a nonamer peptide derived from the signal peptide of human HLA-G. (B) shows a representative analysis of overexpressed HLA-E-UL40-VMPARTLIL (SEQ ID NO: 5) using FACS-assisted analysis. Overexpressed HLA-E-UL40-VMPARTLIL (SEQ ID NO: 5) is demonstrated by increased mean fluorescence intensity for HLA-E-staining when compared to non-transduced controls. Black dotted-lined histograms represent isotype staining, black-lined histograms represents HLA-E staining. (C) shows a representative example of the selective expansion of NKG2C+ NK cells at day 14 using feeder cell lines with different HLA-E-UL40sp constructs with expression of IL-2 or combinatorial expression of IL-2 and mIL-15d. Figure (D) and (E) shows expansion rates of NKG2C+/NKG2A− NK cells after 14 days of co-culture with indicated feeder cell lines. PC3PSCA-IL-2-HLA-E-UL40-VMPARTLFL (VMPARTLFL has SEQ ID NO: 2) and PC3PSCA-IL-2-mIL-15d-HLA-E-UL40-VMPARTLFL (VMPARTLFL has SEQ ID NO: 2) are superior in expanding NKG2C+NK cells enabling in the mean 100 and 115-fold expansion of NKG2C+NK cells, respectively. (F) shows a representative simultaneous staining with CD56 and NKG2C of purified NK cells expanded by co-cultivation with PC3PSCA-IL-2-HLA-E-UL40-VMPARTLFL (VMPARTLFL has SEQ ID NO: 2) and PC3PSCA-IL-2-mIL-15d-HLA-E-UL40-VMPARTLFL (VMPARTLFL has SEQ ID NO: 2) feeder cells. Freshly isolated NK cell (day 0) are mostly CD56dim and also the NKG2C+subset mostly belongs to the CD56dim NK cell population. Unexpectedly, feeder cell-expanded NKG2C+cells are mostly CD56bright indicating that those cells develop from more undifferentiated CD56bright NK cell subset from peripheral blood. (G) shows unexpected outgrowth of NKG2C+/NKG2A− NK cells from NKG2C−/NKG2A+early and NKG2C+/NKG2A+intermediate states using PC3PSCA-IL-2-HLA-E-UL40-VMPARTLFL (VMPARTLFL has SEQ ID NO: 2) and PC3PSCA-IL-2-mIL-15d-HLA-E-UL40-VMPARTLFL (VMPARTLFL has SEQ ID NO: 2) feeder cells during 14 days of expansion. (H), (I), (J) and (K) shows selective expansion of NKG2C+/NKG2A− NK cells from four HCMV-seropositive donors lacking pre-existing expansion of NKG2C+NK cells during 14 days of expansion using the indicated feeder cell lines. Only PC3PSCA-IL-2-HLA-E-UL40-VMPARTLFL (VMPARTLFL has SEQ ID NO: 2) and PC3PSCA-IL-2-mIL-15d-HLA-E-UL40-VMPARTLFL (VMPARTLFL has SEQ ID NO: 2) enabled production of nearly pure (>90% purity) NKG2C+NK cell products (L) depicts a representative analysis of surface markers of NKG2C+cells. NK cell purity was routinely in greater than 95% (CD56+ with gate on living cells, data not shown) after 14 days of expansion with indicated feeder cells demonstrating lack of T cell and NKT cell contamination (CD3) but showing NK phenotype associated with induced self-recognition capacity (NKG2D) and ADCC (CD16). Surprisingly, the majority of expanded NK cells lack signs of exhaustion (TIGIT, PD-1). (M) depicts FACS data from the same expanded NK cells demonstrating a shift to terminal differentiation of NKG2C+NK cells (KIRs, CD57) and unexpectedly shows that a significant fractions of expanded NK cells robustly express high affinity IL-2 receptor (CD25). (N) shows mean expression levels of CD25, PD-1 and TIGIT of expanded NK cells from 5 donors using the indicated feeder cell lines. (O) shows FACS analysis of purified (day 0) and expanded NK cells (day 14) from peripheral blood of a glioblastoma patient (gate on living cells). Cells were stained for NKG2C together with CD25 and PD-1, respectively. (P) shows that patient's derived NKG2C+NK cells unexpectedly lysed allogeneic HLA-E+/HLA-G+glioblastoma cell irrespective of KIR:KIR-ligand setting. NKG2C+NK cells failed in killing of autologous tumor cells lacking expression of HLA-E and HLA-G indicating that cytotoxicity of NKG2C+NK cells can be induced by surface expression of its cognate ligand HLA-E, presumably loaded with activating peptides derived from HLA-G or other activating peptides derived from tumor cells.
Figure 12:
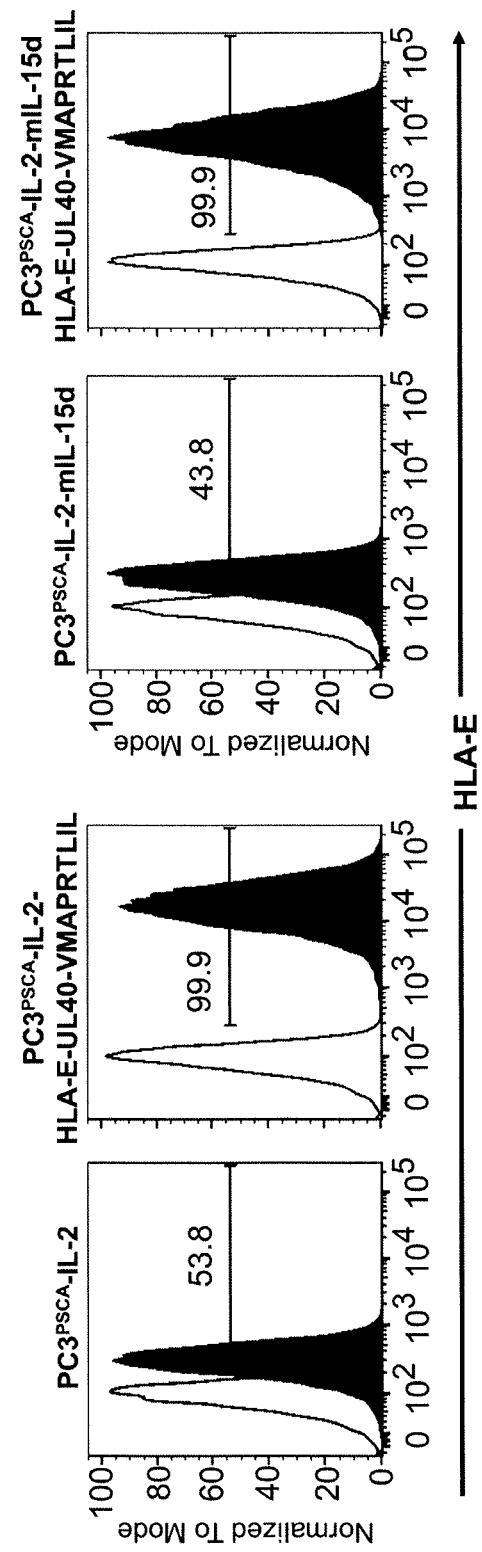
Figure 12:
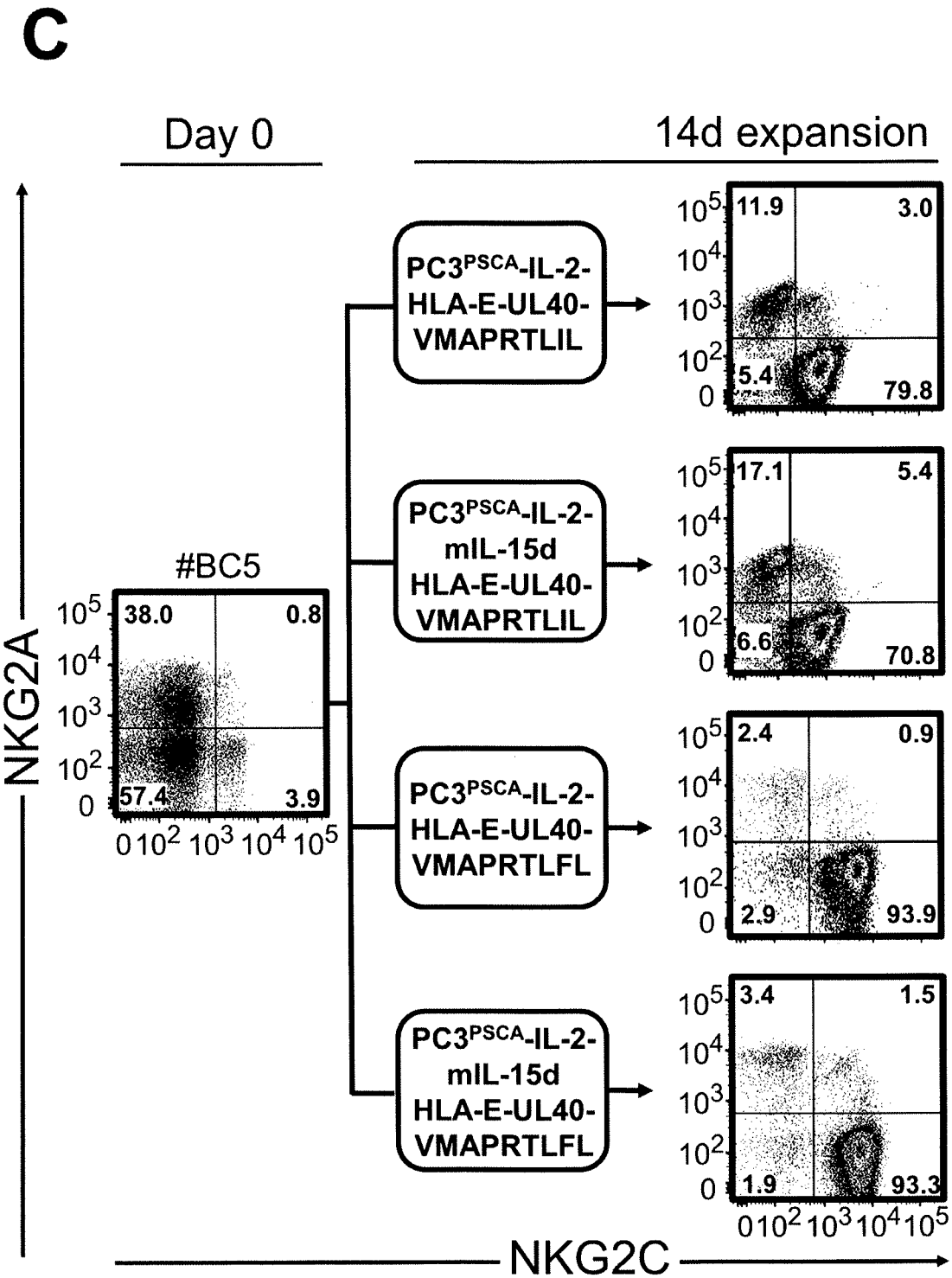
Figure 12:
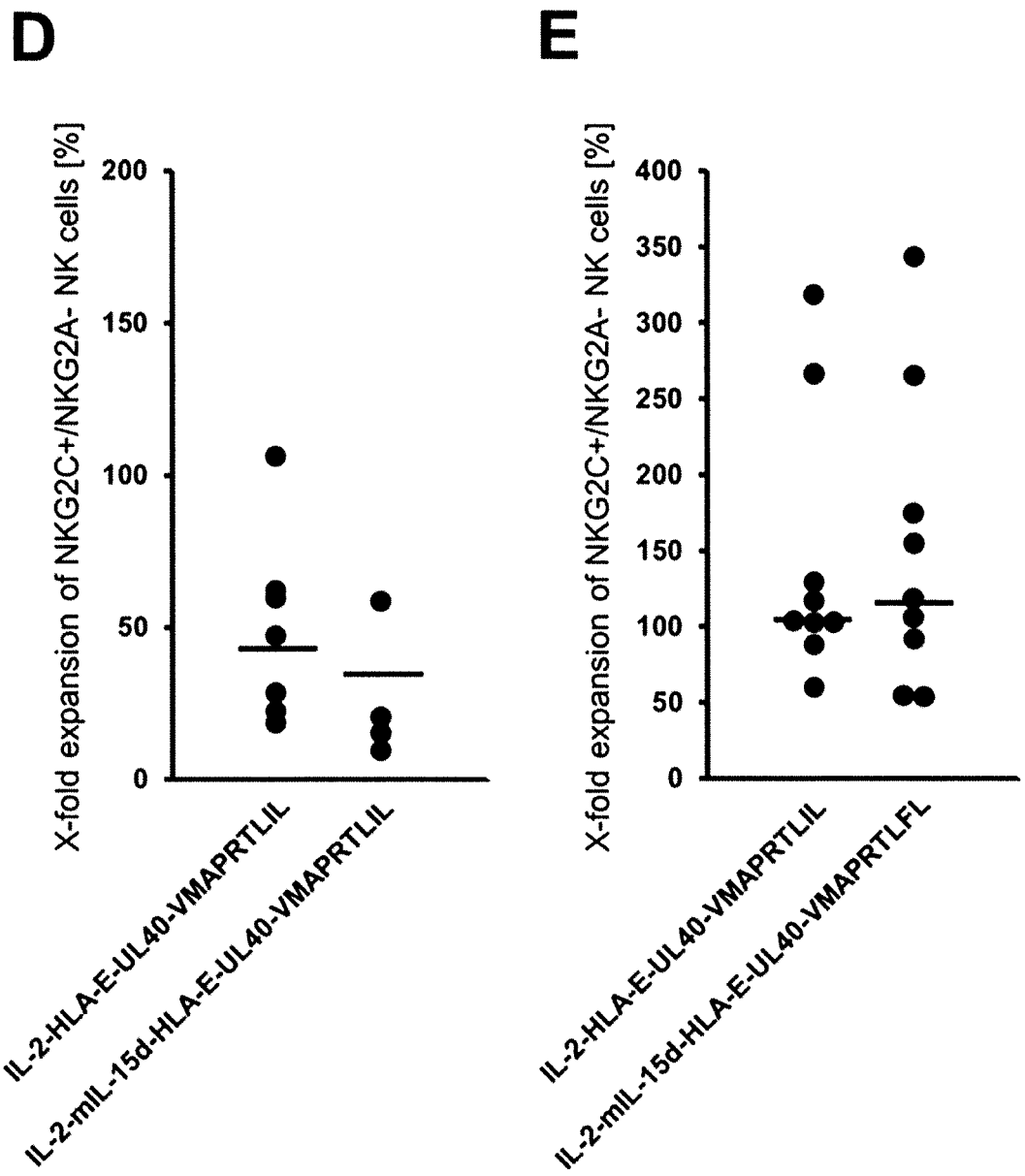
Figure 12:
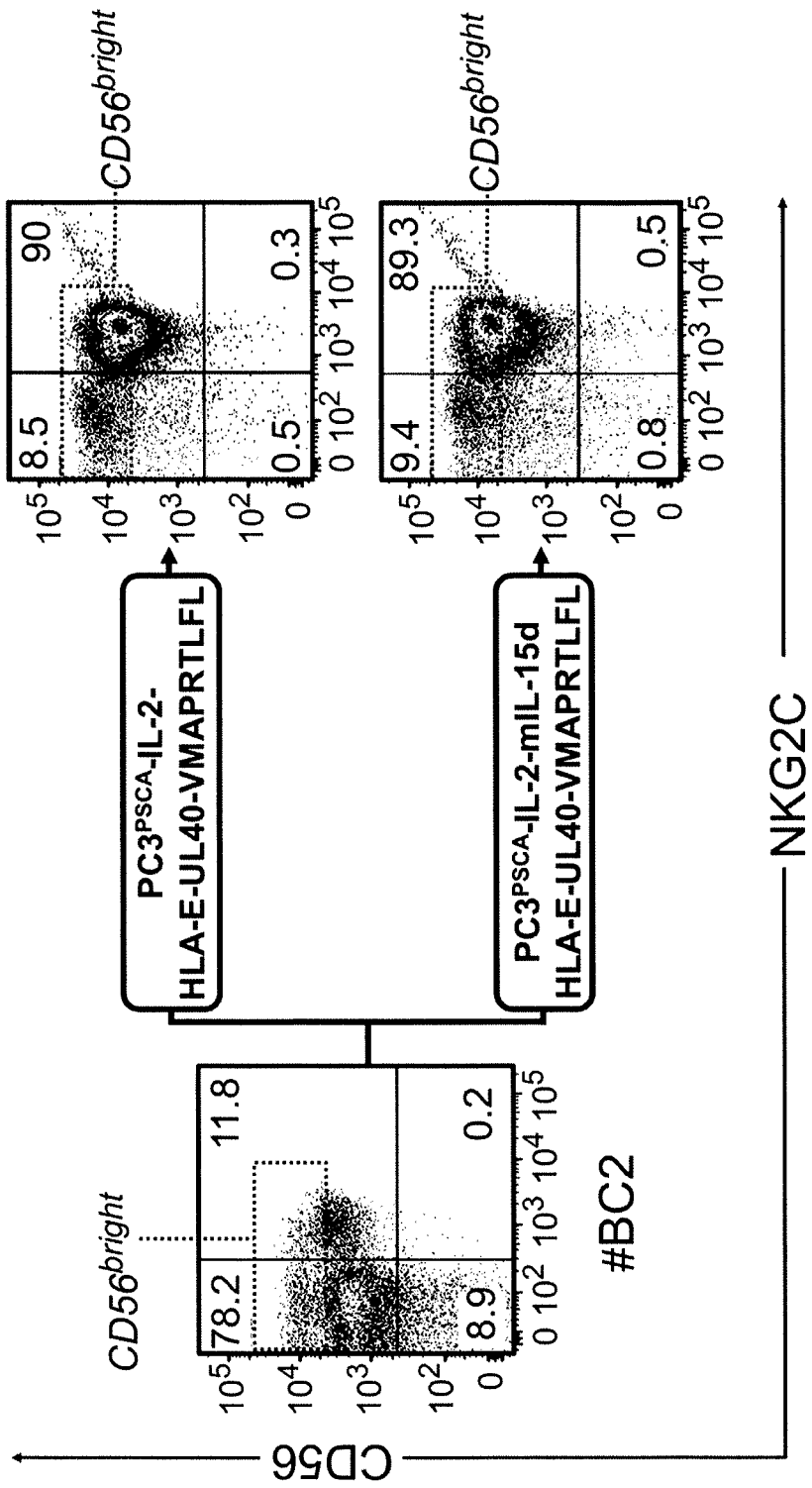
Figure 12:
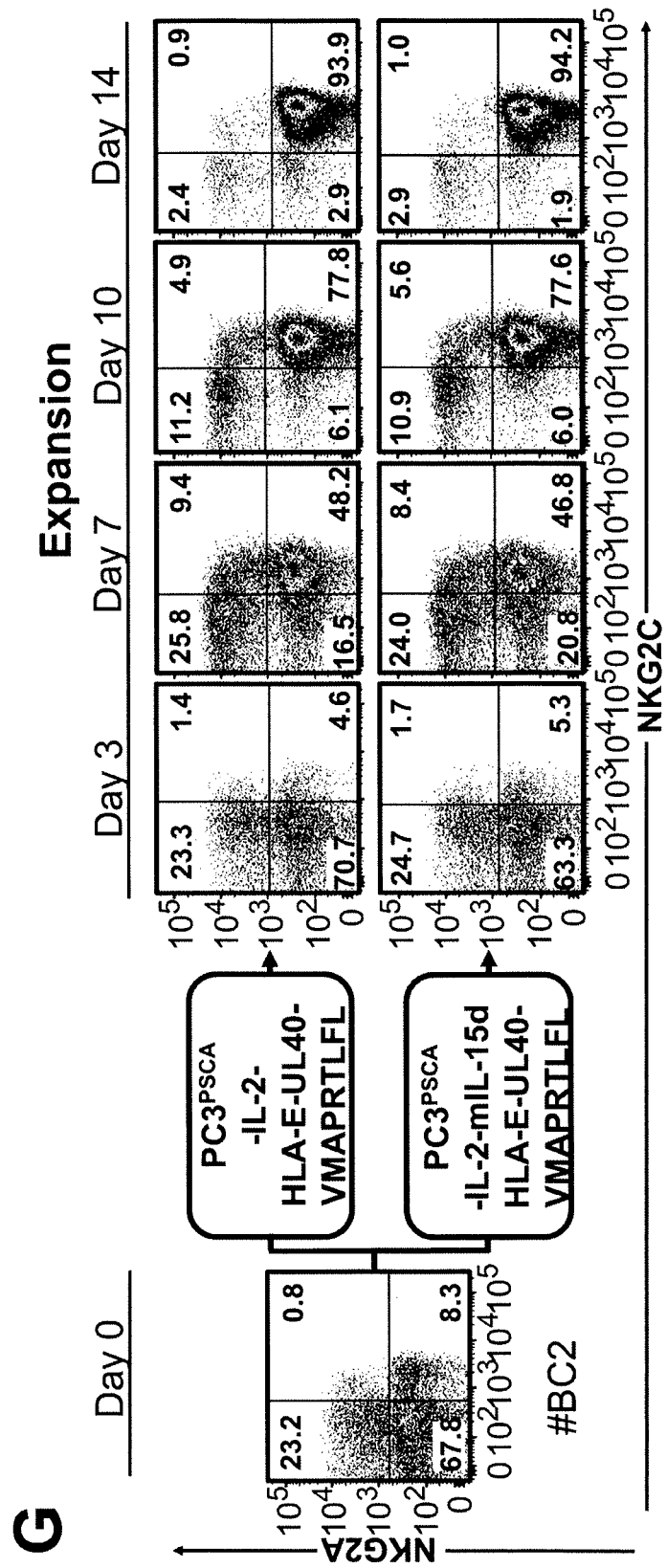
Figure 12:
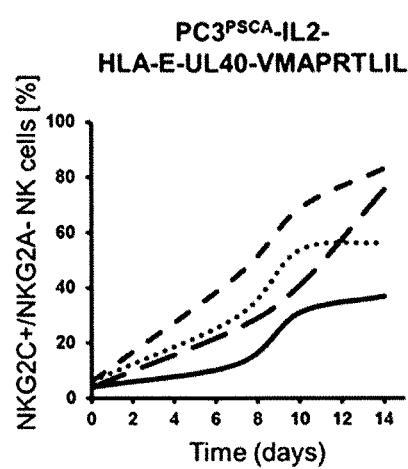
Figure 12:
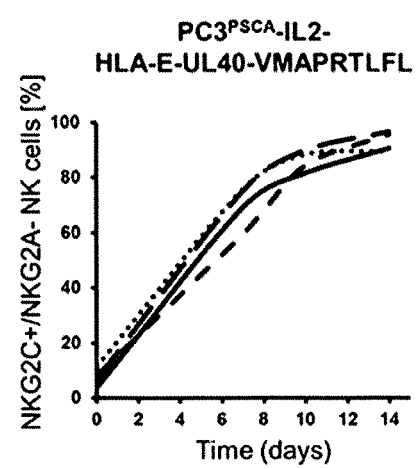
Figure 12:
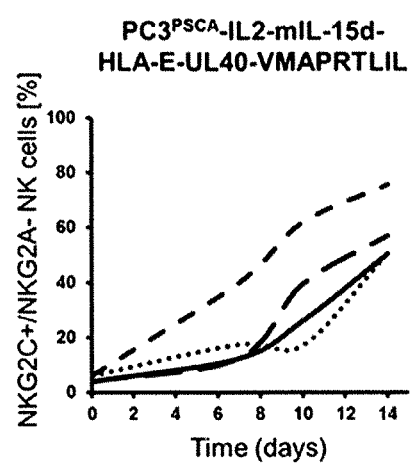
Figure 12:
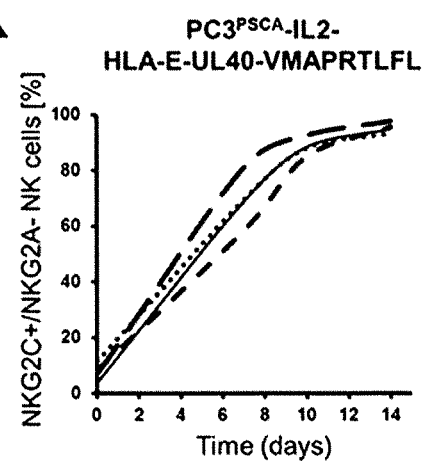
Figure 12:
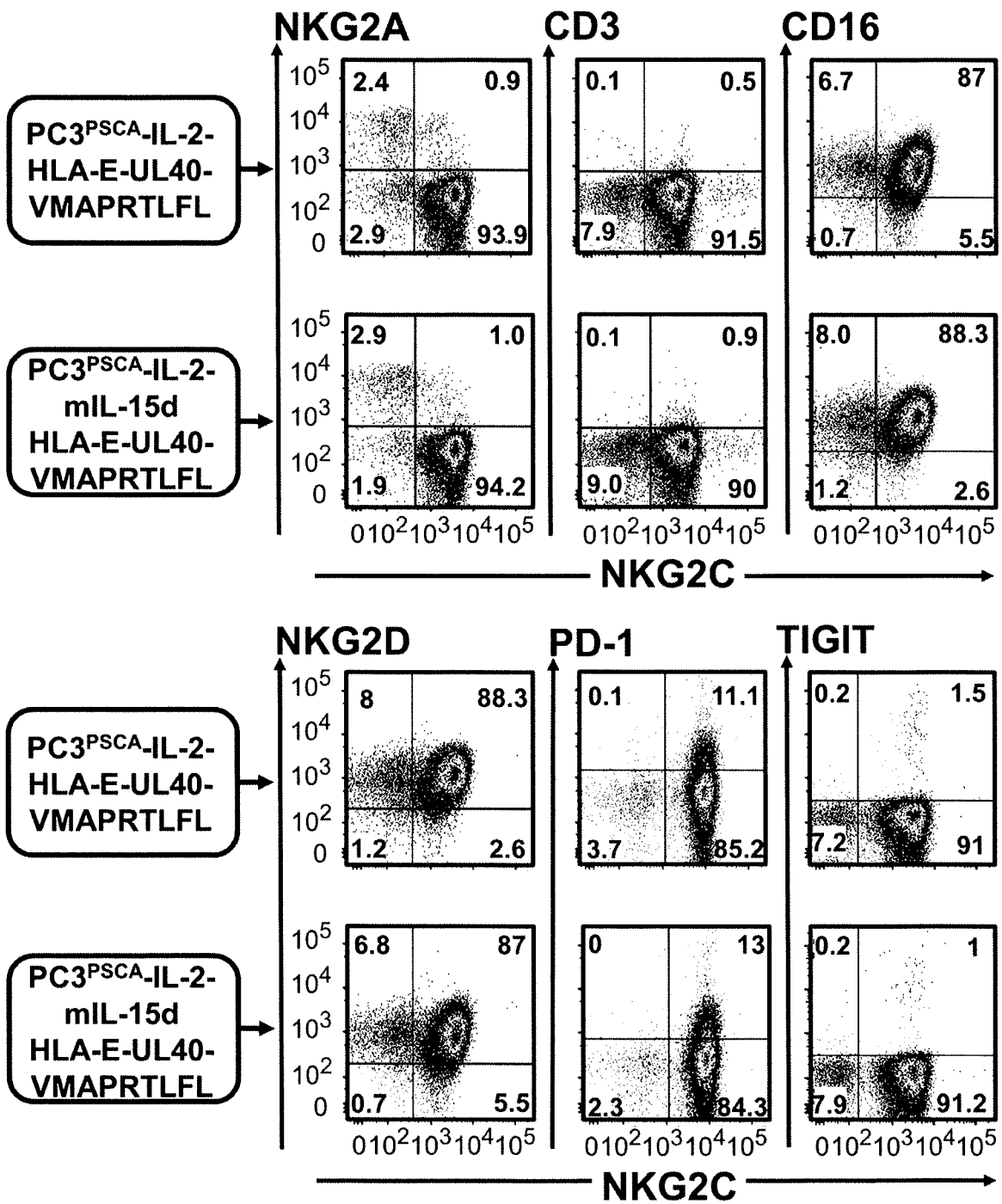
Figure 12:
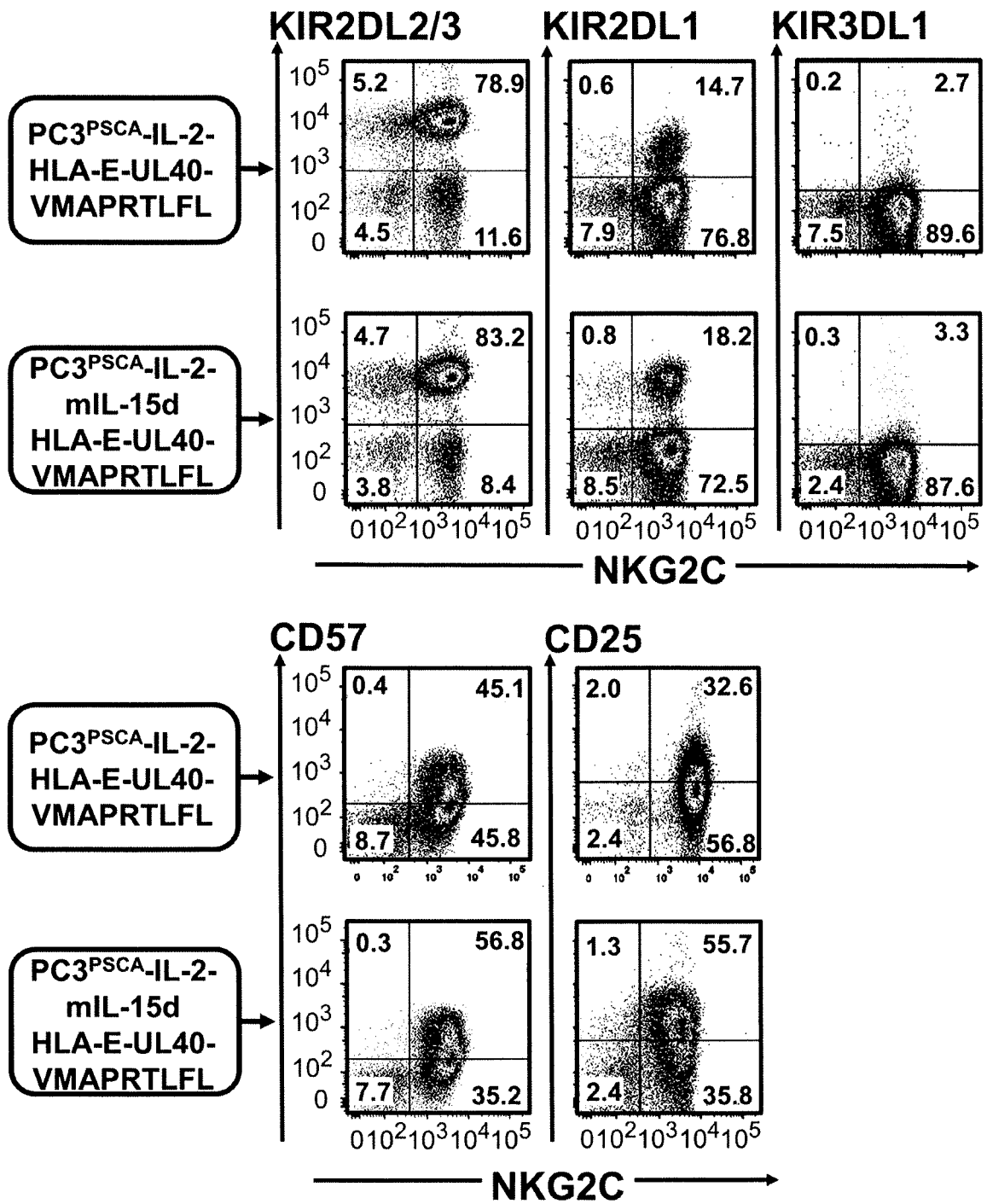
Figure 12:
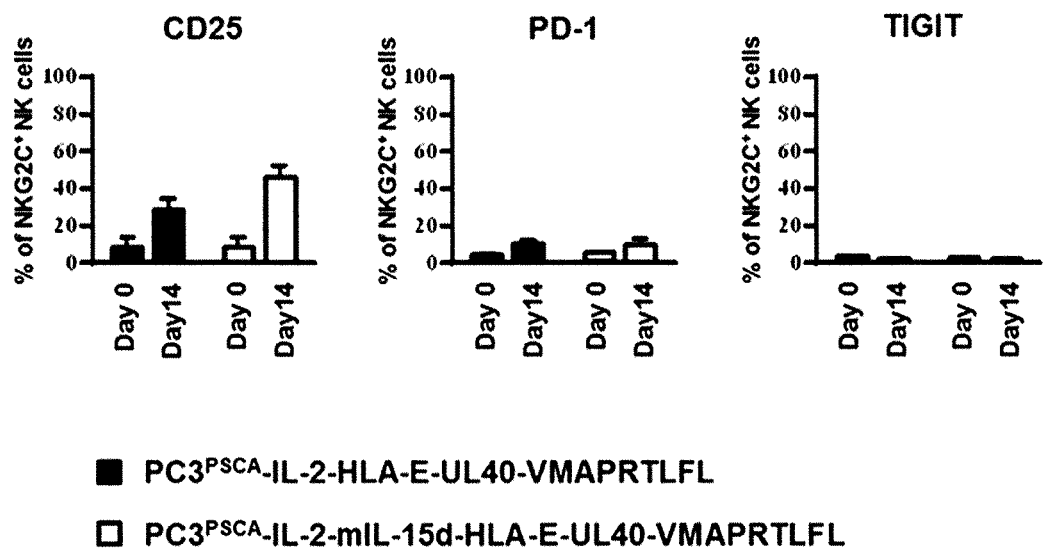
Figure 12:
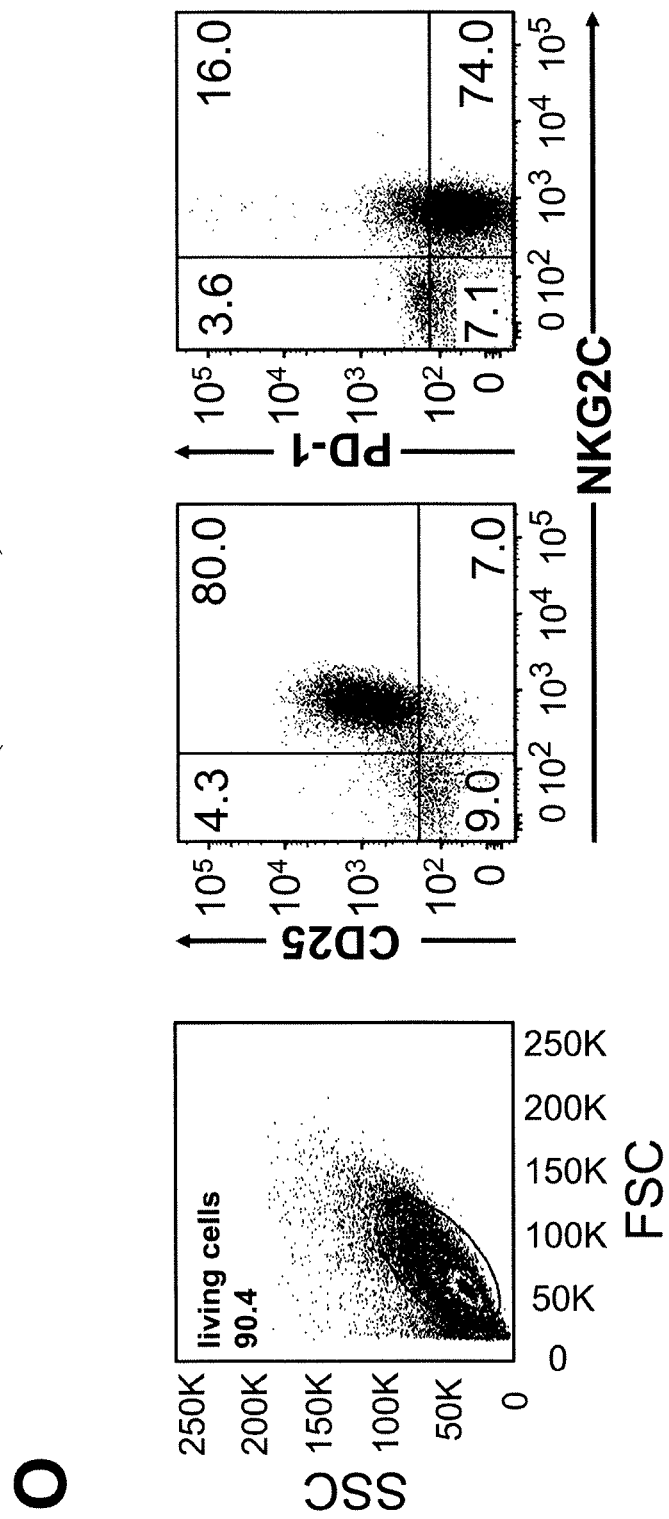
Figure 12:
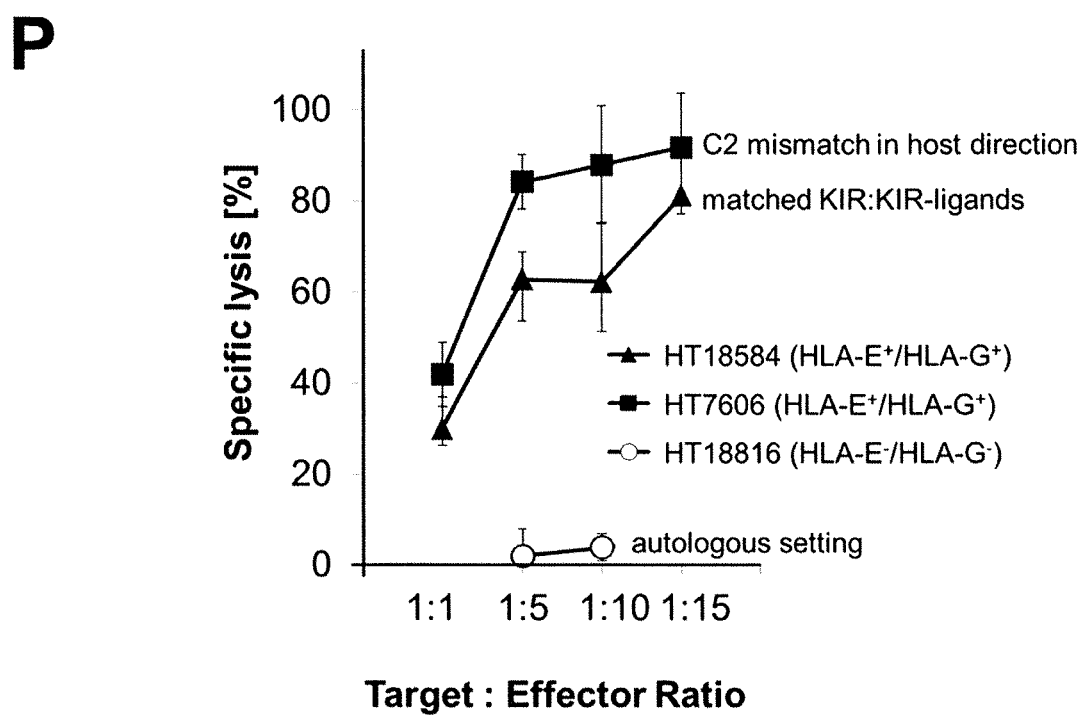
Figure 13:
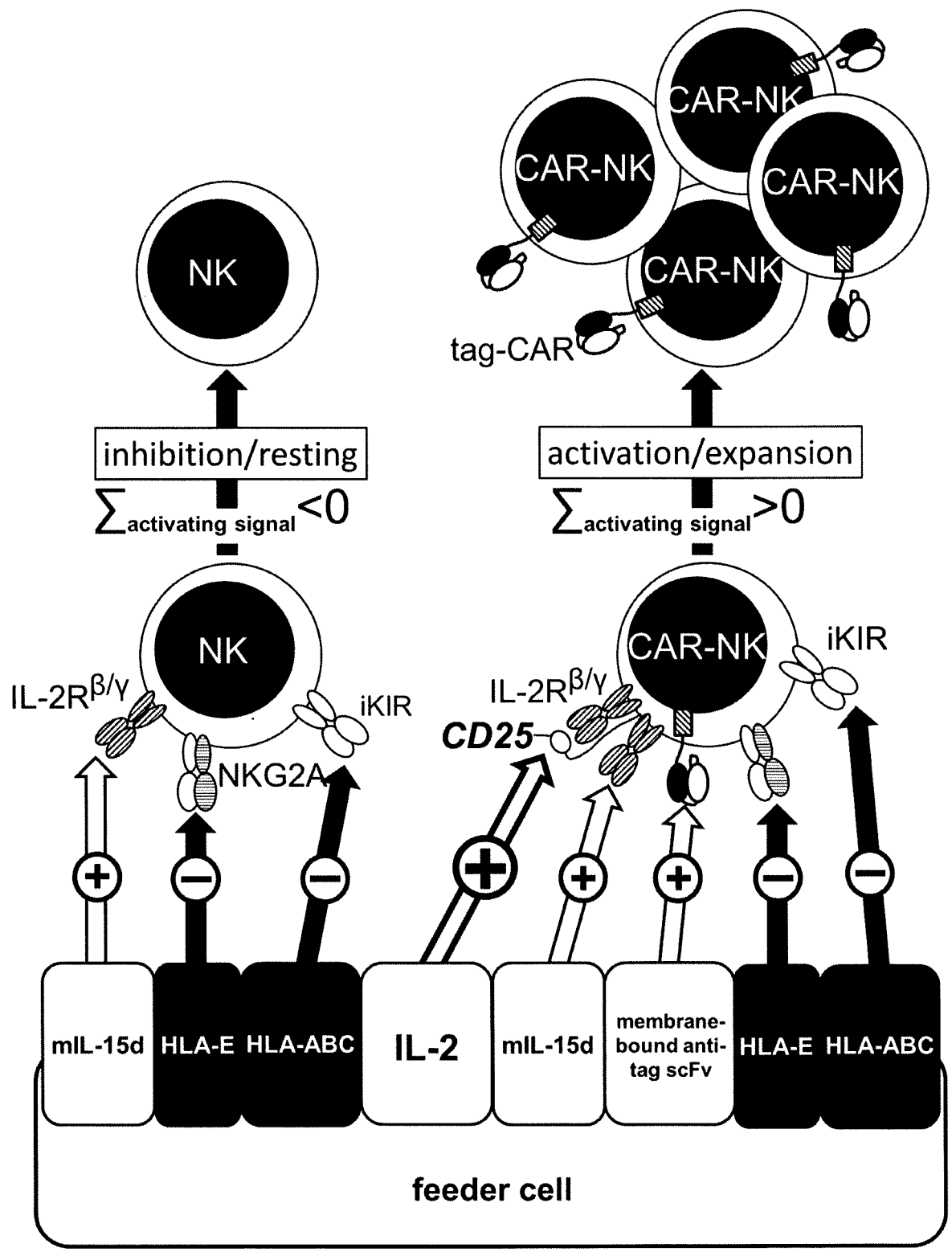
FIG. 13 shows the scheme for selective expansion of epitope-tagged CAR-NK cells. Non-transduced CAR-negative cells are considered to receive strong inhibitory signals through NKG2A and KIRs, which hold them in a resting state. Activation of NK cells through binding of the anti-epitope antibody to the CAR is considered to induce CD25 expression leading to assembly of high affinity IL-2 receptor. Secreted IL-2 of feeder cells then enables the selective expansion of CAR+NK cells.

In a further approach, $PC3^{PSCA}$-IL-$_2$ and $PC3^{PSCA}$-IL-2-mIL-15d feeder cells were successfully genetically modified using a lentiviral vector encoding artificial HLA-E-UL40sp constructs containing VMAPRTLFL (SEQ ID NO: 2) and VMAPRTLIL (SEQ ID NO: 3), respectively, which serve as artificial ligand for NKG2C (FIG. 12A, B). The artificial HLA-E-fusion proteins constructs were chemically synthesized and ligated in frame to the T2A-HYGRO cassette of the pHATtrick-HYGRO lentiviral vector. Lentiviral particles for transduction of $PC3^{PSCA}$-IL-2 and $PC3^{PSCA}$-IL-2-mIL-15d feeder cells were produced by a transient three vector packaging protocol as described previously [65]. Transduced cells were selected with hygromycin treatment for 4 weeks and used for selective expansion of NKG2C+ NK cells by passaging every three to four days as described in Example 2. Surprisingly, all feeder cell lines promoted the selective growth of NKG2C+/NKG2A- NK cells during co-cultivation with feeder cell lines for 14 days (FIG. 12 C). Unexpectedly PC3PSCA-IL-2-HLA-E-UL40-VM-PARTLFL (VMPARTLFL has SEQ ID NO: 2) and PC3PSCA-IL-2-mIL-15d-HLA-E-UL40-VMPARTLFL (VMPARTLFL has SEQ ID NO: 2) feeder cells produced NKG2C+/NKG2A- NK cells with purity higher than 90% (see FIG. 12C). The feeder cell lines expressing HLA-E-UL40-VMPARTLIL (SEQ ID NO: 5) also promoted the outgrowth of NKG2C+/NKG2A- NK cells but surprisingly contained significant fractions of unsolicited NKG2C-/NKG2A+ and double positive NKG2A+/NKG2C+NK cells again indicating the NKG2C+/NKG2A- NK cells develop from NKG2C-/NKG2A+ and double positive NKG2C+/NKG2C+intermediate states (see FIG. 12C). The $PC3^{PSCA}$-IL-2-HLA-E-UL40-VMAPRTLFL (VMPARTLFL has SEQ ID NO: 2) and $PC3^{PSCA}$- IL-2-mIL-15d-HLA-E-UL40-VMAPRTLFL (VMPARTLFL has SEQ ID NO: 2) feeder cells enabled superior production of NKG2C+/NKG2A- NK cells ranging from 100-fold to 115-fold expansion rates (FIG. 12 E) when compared to $PC3^{PSCA}$- IL-2-HLA-E-UL40-VMAPRTLIL (VMPARTLIL has SEQ ID NO: 3) and $PC3^{PSCA}$- IL-2-mIL-15d-HLA-E-UL40-VMAPRTLIL (VMPARTLIL has SEQ ID NO: 3) feeder cells which lead to 47-fold and 37-fold expansions rates (FIG. 12 D), respectively. Further FACS analysis revealed that expanded NKG2C+cells were mostly CD56bright and therefore were raised from the CD56bright population of peripheral blood (FIG. 12F). That NKG2C+/A- NK cells developed in a time dependent manner from NKG2A+/NKG2C- and double-positive NKG2A+/NKG2C+intermediate stages was confirmed using a MACSQUANT Analyzer 10 flow cytometer (Miltenyi Biotec, Germany) assisted analysis of CD56-positive NK cells stained with specific anti NKG2A-FITC and anti-NKG2C-APC antibodies (both from Miltenyi Biotec, Germany). (FIG. 12G). That $PC3^{PSCA}$-IL-2-HLA-E-UL40-VMPARTLFL (VMPARTLFL has SEQ ID NO: 2) and $PC3^{PSCA}$-IL-2-mIL-15d-HLA-E-UL40-VMPARTLFL (VMPARTLFL has SEQ ID NO: 2) feeder cells enabled the production of nearly pure NKG2C+/NKG2A- NK cells during 14 days of expansion was confirmed using purified NK cells from buffy coats of 4 donors (FIG. 12I, K).

Again the $PC3^{PSCA}$-IL-2-HLA-E-UL40-VMPARTLIL (VMPARTLIL has SEQ ID NO: 3) and $PC3^{PSCA}$-IL-2-mIL-15d-HLA-E-UL40-VMPARTLIL (VMPARTLIL has SEQ ID NO: 3) feeder cells were less suitable for producing pure NKG2C+/NKG2A- NK cell products (FIG. 12H, J).

Example 7: Phenotype and Cytotoxicity of Expanded NKG2C+NK Cells

The purity and functional status and differentiation as well as cytotoxicity of expanded NKG2C+/NKG2A- NK cells were assessed by FACS assisted analyses of surface markers and chrome release assay. For phenotypic analysis $2\times10^5$ expanded NK cells were stained with fluorochrome-couple antibodies for CD56, NKG2C, CD3, CD16, NKG2D, PD-1, TIGIT, KIRs, CD57 and CD25 (all provided by Miltenyi Biotec, Germany) and analyzed. IgG isotype controls were included by all measurements. Stained cells were measured by MACSQUANT Analyzer 10 flow cytometer (Miltenyi Biotec, Germany) and analyzed by FLOWJO version X.0.7 software (Tree Star, USA). NK cell purity of the expanded cell product was routinely >95% as determined by CD56/CD3 analysis (Data not shown). As depicted in FIG. 12L NK cells (gate on living cells and CD56) were simultaneously stained for NKG2C and markers. Staining with anti-CD3 showed lack of T cell and NKT cell contamination. Staining for NKG2D and CD16 revealed a NK phenotype associated with induced self-recognition capacity and ADCC.

Surprisingly, the majority of expanded NK cells lack signs of exhaustion (TIGIT, PD-1). (FIG. 12M) depicts FACS data from the same expanded NK cells demonstrating the appearance of terminally differentiated NKG2C+NK cells expressing KIRs and CD57, and unexpectedly shows that a significant fractions of expanded NK cells robustly express high affinity IL-2 receptor (CD25). That PC3PSCA-IL-2-HLA-E-UL40-VMPARTLFL (VMPARTLFL has SEQ ID NO: 2) and PC3PSCA-IL-2-mIL-15d-HLA-E-UL40-VMPARTLFL (VMPARTLFL has SEQ ID NO: 2) feeder cells lead to the expansion of NK cells characterized by a high frequency of affinity IL-2 receptor (CD25+NK cells) and with no induction of immune checkpoint markers PD-1 and TIGIT was confirmed using purified NK cells from 5 buffy coats (FIG. 12N). The cytotoxicity of expanded NKG2C+NK cells prepared from a glioblastoma patient was investigated using primary cell cultures of autologous and allogeneic GBM target cells, which were prepared by a brain tumor dissociation kit and cultivated in DMEM medium. The purity of expanded NKG2C cells was approximately 90%, frequency of CD25 was found to be 80%, and frequency of PD-1 was below 20%. Whereas the allogeneic GBM target cells endogenously expressed HLA-E and HLA-G, the autologous GBM cells were devoid of HLA-E and HLA-G (see FIG. 12O). The patient's derived NKG2C+NK cells unexpectedly lysed allogeneic HLA-E+/HLA-G+glioblastoma cell irrespective of KIR:KIR-ligand setting. More specifically, NKG2C+NK cells lysed allogeneic GBM cells expressing protective C1 and C2 ligands for KIRs. On the other hand, NKG2C+NK cells failed in killing of autologous tumor cells lacking expression of HLA-E and HLA-G. This unexpected result indicates that cytotoxicity of NKG2C+NK cells can be unleashed by surface expression of its cognate ligand HLA-E, presumably loaded with activating peptides derived from tumor cell-associated HLA-G or other activating peptides derived from tumor cells.

Figure 14:
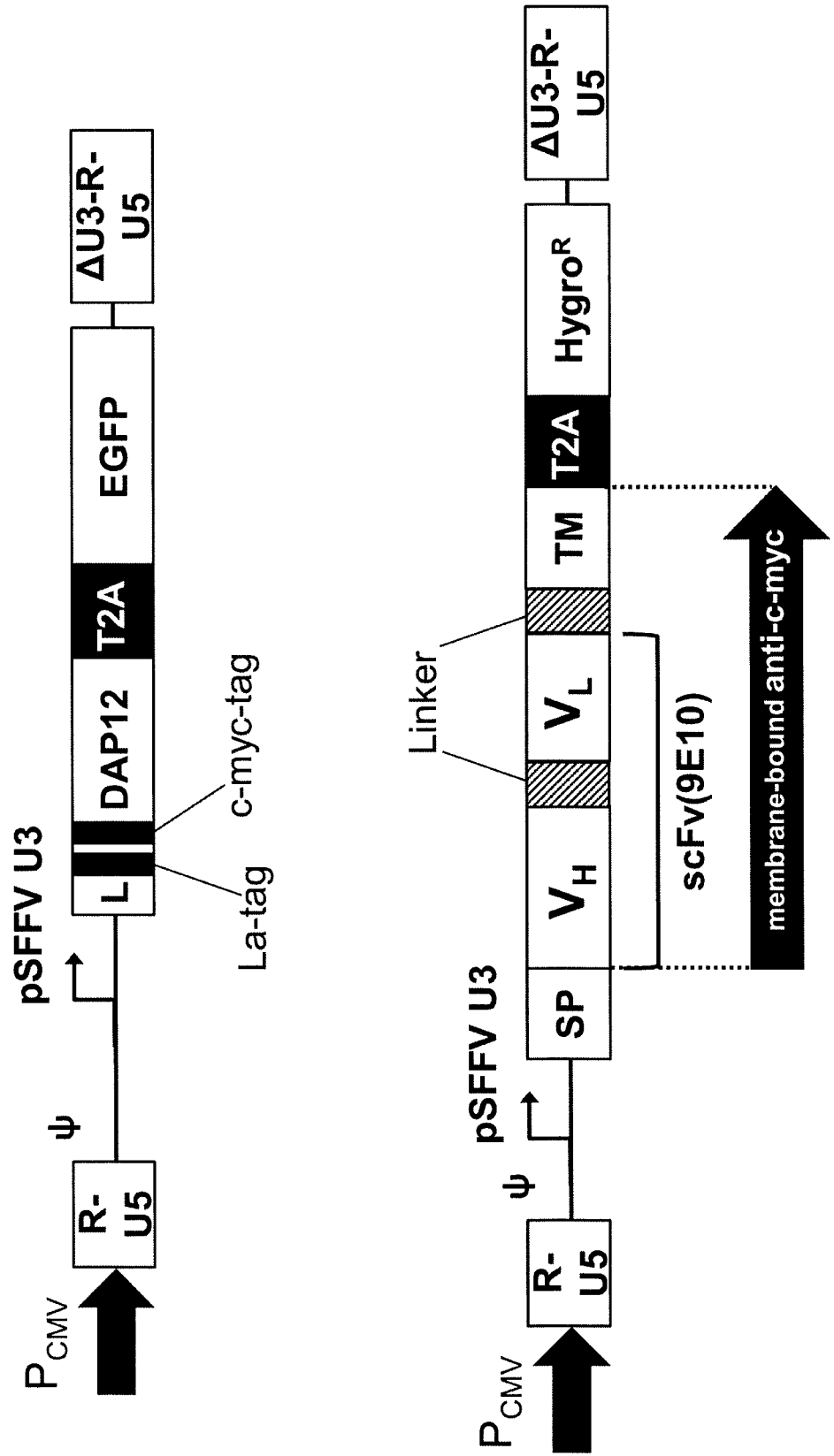
FIG. 14 (A) depicts schematic drawings for the epitope-tagged la-tag-c-myc-tag-DAP12 construct (SEQ ID NO: 18) expressed in NK cells and the membrane-bound anti-c-myc-tag scFv (scFv(9E10)-tm) (SEQ ID NO: 12) expressed in feeder cells. (B) shows Western Blot analysis of feeder cells genetically engineered with scFv(9E10)-tm. Lysates of membrane fractions were subjected to SDS-PAGE electrophoresis. Blotted proteins were detected using an anti-VSV-G antibody and secondary HRP-coupled antibody. (C) shows expansion factors of DAP12-La-tag-myc-tag-transduced NK cells from three donors over time. Expansion rates were calculated by dividing the numbers of c-myc-positive cells to measured initial myc+cell numbers 2 days after transduction (day 0). (D) shows selective enrichment of NK cells transduced with DAP12-La-tag-myc-tag CAR construct in the NK cell population over time.
Figure 14:
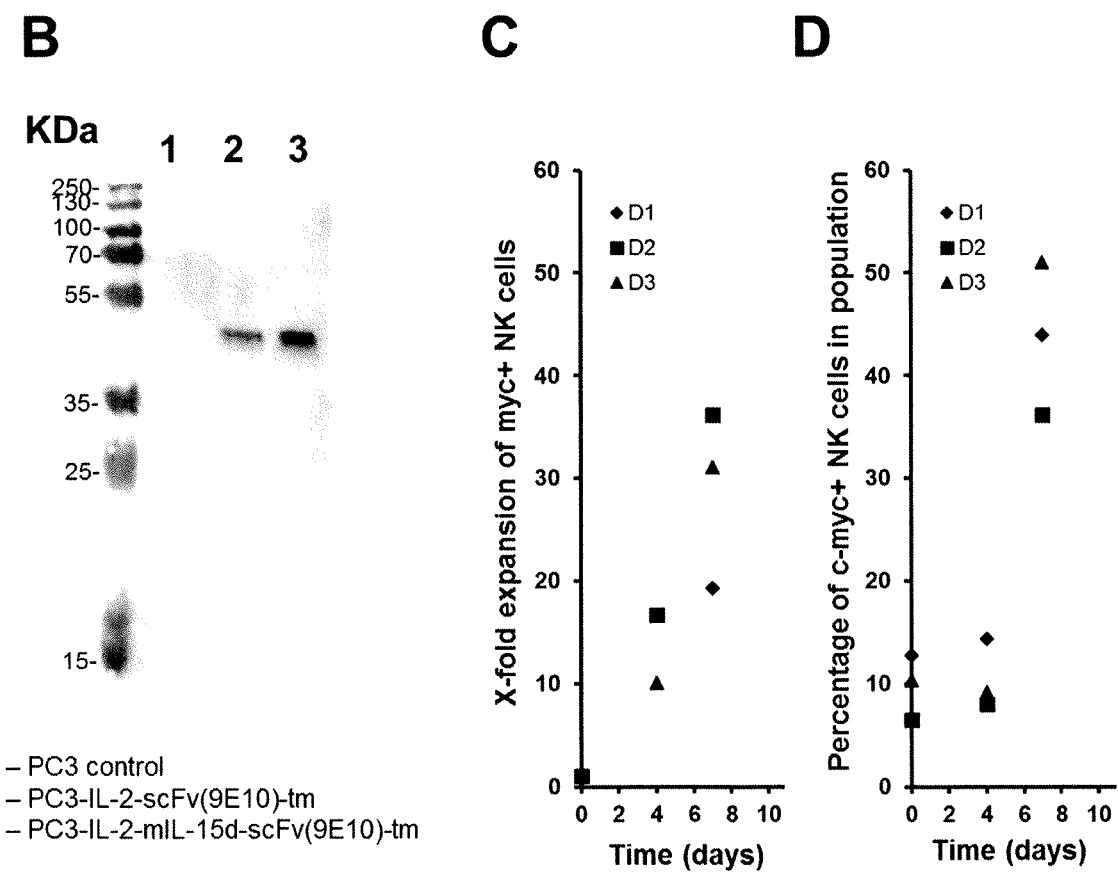

Example 8: Selective Expansion of CAR-NK Cells Containing a Myc-Tag in the CAR Ectodomain Using scFv(9E10)-Tm Modified Feeder Cells The coding sequence for DAP12-la-tag-myc-tag was chemically synthesized and ligated in frame to the T2A-EGFP cassette of pHATtrick-T2A-EGFP lentiviral vector [65]. The membrane bound anti-c-myc scFv (scFv(9E10)-tm) was chemically synthesized and ligated in frame with the T2A-HYGRO cassette of pHATtrick-HYGRO. All new vector inserts were verified by DNA sequencing. Lentiviral particles for transduction of NK cells and of NK-feeder cells, respectively, were produced by a transient three vector packaging protocol as described previously [65]. Transduced feeder cells were selected with hygromycin treatment for 4 weeks and used for selective expansion of transduced NK cells. Every 3-4 days the plate was changed by resuspending the PBMCs in new conditioned medium on newly seeded scFv(9E10)-tm-modified feeder cells. The c-myc-tagged NK cells, expressing the reporter gene EGFP, were analyzed at indicated time points by staining with anti-c-myc-APC (Miltenyi Biotec, Germany) and using a MACSQUANT Analyzer 10 flow cytometer (Miltenyi Biotec, Germany) and FLOWJO version X.0.7 software (Tree Star, USA). Expression of transgenic scFv(9E10)-tm was verified in Western Blot analysis (FIG. 14 B) As depicted in FIGS. 14 C and 14D, PC3$^{PSCA}$-IL-2-scFv(9E10)-tm feeder cells, although known to display inhibitory HLA class I molecules, surprisingly promoted the selective outgrowth and expansion of EGFP-positive DAP12-la-tag-myc-tag-transduced NK cells.

Example 9: Selective Expansion of CAR-NK Cells Using PC3$^{PSCA}$-IL-2 and PC3$^{PSCA}$-IL-2-4-mIL-15d Feeder Cells Genetically Modified to Express Cognate TAA PC3$^{PSCA}$IL-2 and PC3$^{PSCA}$-IL-2-mIL-15d feeder cells were directly used for expansion of NK cells transduced with an anti-PSCA-CAR. Therefore, 2.5×10⁴ feeder cells were plated 24h prior co-cultivation with NK cells. NK cells were continuously transferred to fresh feeder cells after 3 days. The lentiviral construct for the DAP12-based anti-PSCA-CAR is depicted in FIG. 16A. Unexpectedly, co-cultivation of anti-PSCA-CAR-transduced NK cells with PC3$^{PSCA}$IL-$_2$ and PC3$^{PSCA}$-IL-2-mIL-15d feeder cells resulted in increased expression of CD25 on CAR-positive NK cells when analyzed by flow cytometry (FIG. 16B), indicating a shift to the high affinity IL-2 receptor. Moreover, when compared to anti-PSCA-CAR-transduced NK cells which were expanded by activation beads plus exogenous IL-2/IL-21 or expanded by PC3$^{PSCA}$-feeder cell lines expressing IL-2-4-1BBL and IL-2-4-1BBL-mIL-15d, only those CAR-NK cells selectively expanded (FIG. 16C). Strikingly, the relative amount and numbers of CAR-positive NK cells were not improved and even diminished when using the activation bead-expansion method or when using PC3$^{PSCA}$-IL-2-4-1BBL and PC3$^{PSCA}$-IL-2-4-1BBL-mIL-15d feeder cell lines. As depicted in FIG. 16D the PC3$^{PSCA}$-IL-2-4-1BBL and PC3$^{PSCA}$-IL-$_2$-4-1BBL-mIL-15d feeder cells promoted an up to 23-35-fold expansion rates of anti-PSCA-CAR NK cells during 14 days of co-cultivation.

In a further approach, PC3$^{PSCA}$ IL-2 and PC3$^{PSCA}$-IL-2-mIL-15d feeder cells were successfully genetically modified using a lentiviral vector encoding the EGFRvIII mutant form of the EGFR [66]. The lentiviral constructs for expression of EGFRvIII in feeder cells and expression of the c-myc-tagged anti-EGFRvIII-CAR are depicted in FIG. 17A. EGFRvIII-expression levels on feeder cells were analyzed by flow cytometry using biotinylated scFv(MR1.1)-BAP and secondary and biotin-APC-staining. Staining only with secondary antibody was included as control (FIG. 17B). Similar to the above mentioned results, PC3$^{PSCA}$IL-2-EGFRvIII and PC3PSCA-IL-2-mIL-15d-EGFRvIII feeder cells, selectively promoted the growth of NK cells expressing the cognate CAR as determined by FACS-assisted analysis of CD56+/EGFP+cells (FIGS. 17C, D, E).

REFERENCES

[1] M. Yawata, N. Yawata, M. Draghi, F. Partheniou, A. M. Little, and P. Parham, MHC class I-specific inhibitory receptors and their ligands structure diverse human NK-cell repertoires toward a balance of missing self-response. Blood 112 (2008) 2369-2380.

[2] M. Uhrberg, Shaping the human NK cell repertoire: an epigenetic glance at KIR gene regulation. Mol Immunol. 42 (2005) 471-475.

[3] L. L. Lanier, Up on the tightrope: natural killer cell activation and inhibition. Nat. Immunol. 9 (2008) 495-502.

[4] M. G. Morvan and L. L. Lanier, NK cells and cancer: you can teach innate cells new tricks. Nat Rev. Cancer 16 (2015) 7-19.

[5] K. Karre, Express yourself or die: peptides, MHC molecules, and NK cells. Science 267 (1995) 978-979.

[6] L. Moretta and A. Moretta, Unravelling natural killer cell function: triggering and inhibitory human NK receptors. EMBO J. 23 (2004) 255-259.

[7] A. G. Brooks, P. E. Posch, C. J. Scorzelli, F. Borrego, and J. E. Coligan, NKG2A complexed with CD94 defines a novel inhibitory natural killer cell receptor. J Exp. Med 185 (1997) 795-800.

[8] E. J. Petrie, C. S. Clements, J. Lin, L. C. Sullivan, D. Johnson, T. Huyton, A. Heroux, H. L. Hoare, T. Beddoe, H. H. Reid, M. C. Wilce, A. G. Brooks, and J. Rossjohn, CD94-NKG2A recognition of human leukocyte antigen (HLA)-E bound to an HLA class I leader sequence. J Exp. Med 205 (2008) 725-735.

[9] A. M. Martin, E. M. Freitas, C. S. Witt, and F. T. Christiansen, The genomic organization and evolution of the natural killer immunoglobulin-like receptor (KIR) gene cluster. Immunogenetics 51 (2000) 268-280.

[10] M. J. Wilson, M. Torkar, A. Haude, S. Milne, T. Jones, D. Sheer, S. Beck, and J. Trowsdale, Plasticity in the organization and sequences of human KIR/ILT gene families. Proc Natl Acad Sci USA 97 (2000) 4778-4783.

[11] M. Colonna, G. Borsellino, M. Falco, G. B. Ferrara, and J. L. Strominger, HLA-C is the inhibitory ligand that determines dominant resistance to lysis by NK1- and NK2-specific natural killer cells. Proc. Natl. Acad. Sci. U. S A 90 (1993) 12000-12004.

[12] L. Ruggeri, M. Capanni, E. Urbani, K. Perruccio, W. D. Shlomchik, A. Tosti, S. Posati, D. Rogaia, F. Frassoni, F. Aversa, M. F. Martelli, and A. Velardi, Effectiveness of donor natural killer cell alloreactivity in mismatched hematopoietic transplants. Science 295 (2002) 2097-2100.

[13] L. Ruggeri, A. Mancusi, K. Perruccio, E. Burchielli, M. F. Martelli, and A. Velardi, Natural killer cell alloreactivity for leukemia therapy. J. Immunother. 28 (2005) 175-182.

[14] P. Hansasuta, T. Dong, H. Thananchai, M. Weekes, C. Willberg, H. Aldemir, S. Rowland-Jones, and V. M. Braud, Recognition of HLA-A3 and HLA-A11 by KIR3DL2 is peptide-specific. Eur. J. Immunol. 34 (2004) 1673-1679.

[15] M. Uhrberg, N. M. Valiante, B. P. Shum, H. G. Shilling, K. Lienert-Weidenbach, B. Corliss, D. Tyan, L. L. Lanier, and P. Parham, Human diversity in killer cell inhibitory receptor genes. Immunity 7 (1997) 753-763.

[16] L. Ruggeri, A. Mancusi, E. Burchielli, K. Perruccio, F. Aversa, M. F. Martelli, and A. Velardi, Natural killer cell recognition of missing self and haploidentical hematopoietic transplantation. Semin. Cancer Biol. 16 (2006) 404-411.

[17] M. Colonna, F. Navarro, T. Bellon, M. Llano, P. Garcia, J. Samaridis, L. Angman, M. Cella, and M. Lopez-Botet, A common inhibitory receptor for major histocompatibility complex class I molecules on human lymphoid and myelomonocytic cells. J Exp. Med 186 (1997) 1809-1818.

[18] A. G. Freud and M. A. Caligiuri, Human natural killer cell development. Immunol. Rev. 214 (2006) 56-72.

[19] L. Moretta, Dissecting CD56dim human NK cells. Blood 116 (2010) 3689-3691.

[20] C. Romagnani, K. Juelke, M. Falco, B. Morandi, A. D'Agostino, R. Costa, G. Ratto, G. Forte, P. Carrega, G. Lui, R. Conte, A. Strowig, A. Moretta, C. Munz, A. Thiel, L. Moretta, and G. Ferlazzo, CD56bright. J Immunol. 178 (2007) 4947-4955.

[21] F. Simonetta, M. Alvarez, and R. S. Negrin, Natural Killer Cells in Graft-versus-Host-Disease after Allogeneic Hematopoietic Cell Transplantation. Front Immunol. 8 (2017) 465.

[22] J. Yu, J. M. Venstrom, X. R. Liu, J. Pring, R. S. Hasan, R. J. O'Reilly, and K. C. Hsu, Breaking tolerance to self, circulating natural killer cells expressing inhibitory KIR for non-self HLA exhibit effector function after T cell-depleted allogeneic hematopoietic cell transplantation. Blood 113 (2009) 3875-3884.

[23] X. Y. Zhao, Y. J. Chang, and X. J. Huang, Conflicting impact of alloreactive NK cells on transplantation outcomes after haploidentical transplantation: do the reconstitution kinetics of natural killer cells create these differences? Biol Blood Marrow Transplant 17 (2011) 1436-1442.

[24] G. F. Torelli, A. Guarini, G. Palmieri, M. Breccia, A. Vitale, A. Santoni, and R. Foa, Expansion of cytotoxic effectors with lytic activity against autologous blasts from acute myeloid leukaemia patients in complete haematological remission. Br. J Haematol. 116 (2002) 299-307.

[25] M. Berg, A. Lundqvist, P. McCoy, Jr., L. Samsel, Y. Fan, A. Tawab, and R. Childs, Clinical-grade ex vivo-expanded human natural killer cells up-regulate activating receptors and death receptor ligands and have enhanced cytolytic activity against tumor cells. Cytotherapy 11 (2009) 341-355.

[26] P. S. Becker, G. Suck, P. Nowakowska, E. Ullrich, E. Seifried, P. Bader, T. Tonn, and C. Seidl, Selection and expansion of natural killer cells for NK cell-based immunotherapy. Cancer Immunol. Immunother. 65 (2016) 477-484.

[27] V. Beziat, L. L. Liu, J. A. Malmberg, M. A. Ivarsson, E. Sohlberg, A. T. Bjorklund, C. Retiere, E. Sverremark-Ekstrom, J. Traherne, P. Ljungman, M. Schaffer, D. A. Price, J. Trowsdale, J. Michaelsson, H. G. Ljunggren, and K. J. Malmberg, NK cell responses to cytomegalovirus infection lead to stable imprints in the human KIR repertoire and involve activating KIRs. Blood 121 (2013) 2678-2688.

[28] D. A. Knorr, V. Bachanova, M. R. Verneris, and J. S. Miller, Clinical utility of natural killer cells in cancer therapy and transplantation. Semin. Immunol. 26 (2014) 161-172.

[29] H. Fujisaki, H. Kakuda, N. Shimasaki, C. Imai, J. Ma, T. Lockey, P. Eldridge, W. H. Leung, and D. Campana, Expansion of highly cytotoxic human natural killer cells for cancer cell therapy. Cancer Res. 69 (2009) 4010-4017.

[30] H. Zhang, Y. Cui, N. Voong, M. Sabatino, D. F. Stroncek, S. Morisot, C. I. Civin, A. S. Wayne, B. L. Levine, and C. L. Mackall, Activating signals dominate inhibitory signals in CD137L/IL-15 activated natural killer cells. J Immunother. 34 (2011) 187-195.

[31] N. N. Shah, K. Baird, C. P. Delbrook, T. A. Fleisher, M. E. Kohler, S. Rampertaap, K. Lemberg, C. K. Hurley, D. E. Kleiner, M. S. Merchant, S. Pittaluga, M. Sabatino, D. F. Stroncek, A. S. Wayne, H. Zhang, T. J. Fry, and C. L. Mackall, Acute GVHD in patients receiving IL-15/4-1BBL activated NK cells following T-cell-depleted stem cell transplantation. Blood 125 (2015) 784-792.

[32] D. Cho and D. Campana, Expansion and activation of natural killer cells for cancer immunotherapy. Korean J Lab Med 29 (2009) 89-96.

[33] W. Gong, W. Xiao, M. Hu, X. Weng, L. Qian, X. Pan, and M. Ji, Ex vivo expansion of natural killer cells with high cytotoxicity by K562 cells modified to co-express major histocompatibility complex class I chain-related protein A, 4-1BB ligand, and interleukin-15. Tissue Antigens 76 (2010) 467-475.

[34] C. J. Denman, V. V. Senyukov, S. S. Somanchi, P. V. Phatarpekar, L. M. Kopp, J. L. Johnson, H. Singh, L. Hurton, S. N. Maiti, M. H. Huls, R. E. Champlin, L. J. Cooper, and D. A. Lee, Membrane-bound IL-21 promotes sustained ex vivo proliferation of human natural killer cells. PLoS One 7 (2012) e30264.

[35] S. Michen and A. Temme, Genetically Engineered Natural Killer Cells as a Means for Adoptive Tumor Immunotherapy. Crit Rev. Immunol. 36 (2016) 329-347.

[36] L. L. Lanier, NKG2D Receptor and Its Ligands in Host Defense. Cancer Immunol. Res 3 (2015) 575-582.

[37] S. O. Ciurea, J. R. Schafer, R. Bassett, C. J. Denman, K. Cao, D. Willis, G. Rondon, J. Chen, D. Soebbing, I. Kaur, A. Gulbis, S. Ahmed, K. Rezvani, E. J. Shpall, D. A. Lee, and R. E. Champlin, Phase 1 clinical trial using mbIL21 ex vivo-expanded donor-derived NK cells after haploidentical transplantation. Blood 130 (2017) 1857-1868.

[38] K. J. Malmberg, Y. T. Bryceson, M. Carlsten, S. Andersson, A. Bjorklund, N. K. Bjorkstrom, B. C. Baumann, C. Fauriat, E. Alici, M. S. Dilber, and H. G. Ljunggren, NK cell-mediated targeting of human cancer and possibilities for new means of immunotherapy. Cancer Immunol. Immunother. 57 (2008) 1541-1552.

[39] M. Llano, N. Lee, F. Navarro, P. Garcia, J. P. Albar, D. E. Geraghty, and M. Lopez-Botet, HLA-E-bound peptides influence recognition by inhibitory and triggering CD94/NKG2 receptors: preferential response to an HLA-G-derived nonamer. Eur J Immunol. 28 (1998) 2854-2863.

[40] L. L. Liu, A. Pfefferle, V. O. Yi Sheng, A. T. Bjorklund, V. Beziat, J. P. Goodridge, and K. J. Malmberg, Harnessing adaptive natural killer cells in cancer immunotherapy. Mol Oncol 9 (2015) 1904-1917.

[41] Q. Hammer, T. Ruckert, E. M. Borst, J. Dunst, A. Haubner, P. Durek, F. Heinrich, G. Gasparoni, M. Babic, A. Tomic, G. Pietra, M. Nienen, I. W. Blau, J. Hofmann, I. K. Na, I. Prinz, C. Koenecke, P. Hemmati, N. Babel, R. Arnold, J. Walter, K. Thurley, M. F. Mashreghi, M. Messerle, and C. Romagnani, Peptide-specific recognition of human cytomegalovirus strains controls adaptive natural killer cells. Nat Immunol. 19 (2018) 453-463.

[42] H. T. Reyburn, O. Mandelboim, M. Vales-Gomez, D. M. Davis, L. Pazmany, and J. L. Strominger, The class I MHC homologue of human cytomegalovirus inhibits attack by natural killer cells. Nature 386 (1997) 514-517.

[43] A. Rolle, M. Meyer, S. Calderazzo, D. Jager, and F. Momburg, Distinct HLA-E Peptide Complexes Modify Antibody-Driven Effector Functions of Adaptive NK Cells. Cell Rep 24 (2018) 1967-1976.

[44] G. Pietra, C. Romagnani, C. Manzini, L. Moretta, and M. C. Mingari, The emerging role of HLA-E-restricted CD8+T lymphocytes in the adaptive immune response to pathogens and tumors. J Biomed Biotechnol. 2010 (2010) 907092.

[45] L. L. Liu, V. Beziat, V. Y. S. Oei, A. Pfefferle, M. Schaffer, S. Lehmann, E. Hellstrom-Lindberg, S. Soderhall, M. Heyman, D. Grander, and K. J. Malmberg, Ex Vivo Expanded Adaptive NK Cells Effectively Kill Primary Acute Lymphoblastic Leukemia Cells. Cancer Immunol. Res 5 (2017) 654-665.

[46] M. Guma, A. Angulo, C. Vilches, N. Gomez-Lozano, N. Malats, and M. Lopez-Botet, Imprint of human cytomegalovirus infection on the NK cell receptor repertoire. Blood 104 (2004) 3664-3671.

[47] M. Cartellieri, M. Bachmann, A. Feldmann, C. Bippes, S. Stamova, R. Wehner, A. Temme, and M. Schmitz, Chimeric antigen receptor-engineered T cells for immunotherapy of cancer. J. Biomed. Biotechnol. 2010 (2010) 956304.

[48] S. A. Feldman, Y. Assadipour, I. Kriley, S. L. Goff, and S. A. Rosenberg, Adoptive Cell Therapy-Tumor-Infiltrating Lymphocytes, T-Cell Receptors, and Chimeric Antigen Receptors. Semin. Oncol 42 (2015) 626-639.

[49] M. Kalos, B. L. Levine, D. L. Porter, S. Katz, S. A. Grupp, A. Bagg, and C. H. June, T cells with chimeric antigen receptors have potent antitumor effects and can establish memory in patients with advanced leukemia. Sci. Transl. Med 3 (2011) 95ra73.

[50] C. Fauriat, E. O. Long, H. G. Ljunggren, and Y. T. Bryceson, Regulation of human NK-cell cytokine and chemokine production by target cell recognition. Blood 115 (2010) 2167-2176.

[51] T. A. Fehniger, M. H. Shah, M. J. Turner, J. B. VanDeusen, S. P. Whitman, M. A. Cooper, K. Suzuki, M. Wechser, F. Goodsaid, and M. A. Caligiuri, Differential cytokine and chemokine gene expression by human NK cells following activation with IL-18 or IL-15 in combination with IL-12: implications for the innate immune response. J Immunol. 162 (1999) 4511-4520.

[52] A. Kruschinski, A. Moosmann, I. Poschke, H. Norell, M. Chmielewski, B. Seliger, R. Kiessling, T. Blankenstein, H. Abken, and J. Charo, Engineering antigen-specific primary human NK cells against HER-2 positive carcinomas. Proc. Natl. Acad. Sci. U.S.A 105 (2008) 17481-17486.

[53] R. A. Morgan, J. C. Yang, M. Kitano, M. E. Dudley, C. M. Laurencot, and S. A. Rosenberg, Case report of a serious adverse event following the administration of T cells transduced with a chimeric antigen receptor recognizing ERBB2. Mol. Ther. 18 (2010) 843-851.

[54] J. N. Brudno and J. N. Kochenderfer, Toxicities of chimeric antigen receptor T cells: recognition and management. Blood 127 (2016) 3321-3330.

[55] C. H. Lamers, S. Sleijfer, S. S. van, E. P. van, K. B. van, C. Groot, A. Vulto, B. M. den, E. Oosterwijk, R. Debets, and J. W. Gratama, Treatment of metastatic renal cell carcinoma with CAIX CAR-engineered T cells: clinical evaluation and management of on-target toxicity. Mol Ther. 21 (2013) 904-912.

[56] L. S. Wylezinski and J. Hawiger, Interleukin 2 Activates Brain Microvascular Endothelial Cells Resulting in Destabilization of Adherens Junctions. J Biol Chem 291 (2016) 22913-22923.

[57] Y. Hu, J. Sun, Z. Wu, J. Yu, Q. Cui, C. Pu, B. Liang, Y. Luo, J. Shi, A. Jin, L. Xiao, and H. Huang, Predominant cerebral cytokine release syndrome in CD19-directed chimeric antigen receptor-modified T cell therapy. J Hematol. Oncol 9 (2016) 70.

[58] N. Shimasaki, H. Fujisaki, D. Cho, M. Masselli, T. Lockey, P. Eldridge, W. Leung, and D. Campana, A clinically adaptable method to enhance the cytotoxicity of natural killer cells against B-cell malignancies. Cytotherapy. 14 (2012) 830-840.

[59] F. N. Cho, T. H. Chang, C. W. Shu, M. C. Ko, S. K. Liao, K. H. Wu, M. S. Yu, S. J. Lin, Y. C. Hong, C. H. Chen, C. H. Hung, and Y. H. Chang, Enhanced cytotoxicity of natural killer cells following the acquisition of chimeric antigen receptors through trogocytosis. PLoS One 9 (2014) e109352.

[60] M. Carlsten and R. W. Childs, Genetic Manipulation of NK Cells for Cancer Immunotherapy: Techniques and Clinical Implications. Front Immunol. 6 (2015) 266.

[61] S. Sijmons, K. Thys, N. M. Mbong, D. E. Van, J. Dvorak, L. M. Van, G. Li, R. Tachezy, L. Busson, J. Aerssens, R. M. Van, and P. Maes, High-throughput analysis of human cytomegalovirus genome diversity highlights the widespread occurrence of gene-disrupting mutations and pervasive recombination. J Virol. 89 (2015) 7673-7695.

[62] C. J. Wikstrand, L. P. Hale, S. K. Batra, M. L. Hill, P. A. Humphrey, S. N. Kurpad, R. E. McLendon, D. Moscatello, C. N. Pegram, C. J. Reist, and, Monoclonal antibodies against EGFRvIII are tumor specific and react with breast and lung carcinomas and malignant gliomas. Cancer Res. 55 (1995) 3140-3148.

[63] D. Bachmann, R. Aliperta, R. Bergmann, A. Feldmann, S. Koristka, C. Arndt, S. Loff, P. Welzel, S. Albert, A. Kegler, A. Ehninger, M. Cartellieri, G. Ehninger, M. Bornhauser, B. M. von, C. Werner, J. Pietzsch, J. Steinbach, and M. Bachmann, Retargeting of UniCAR T cells with an in vivo synthesized target module directed against CD19 positive tumor cells. Oncotarget 9 (2018) 7487-7500.

[64] L. R. Loureiro, A. Feldmann, R. Bergmann, S. Koristka, N. Berndt, C. Arndt, J. Pietzsch, C. Novo, P. Videira, and M. Bachmann, Development of a novel target module redirecting UniCAR T cells to Sialyl Tn-expressing tumor cells. Blood Cancer J 8 (2018) 81.

[65] K. Topfer, M. Cartellieri, S. Michen, R. Wiedemuth, N. Muller, D. Lindemann, M. Bachmann, M. Fussel, G. Schackert, and A. Temme, DAP12-Based Activating Chimeric Antigen Receptor for NK Cell Tumor Immunotherapy. J Immunol.2015).

[66] N. Muller, S. Michen, S. Tietze, K. Topfer, A. Schulte, K. Lamszus, M. Schmitz, G. Schackert, I. Pastan, and A. Temme, Engineering NK Cells Modified With an EGFRvIII-specific Chimeric Antigen Receptor to Overexpress CXCR4 Improves Immunotherapy of CXCL12/SDF-1alpha-secreting Glioblastoma. J Immunother. 38 (2015) 197-210.

[67] S. Tietze, I. Schau, S. Michen, F. Ennen, A. Janke, G. Schackert, A. Aigner, D. Appelhans, and A. Temme, A Poly(Propyleneimine) Dendrimer-Based Polyplex-System for Single-Chain Antibody-Mediated Targeted Delivery and Cellular Uptake of SiRNA. Smal12017).

The invention claimed is:

1. A method for specifically inducing the proliferation and expansion of non-hyper-activated human NK cells which are tolerant to self, said method comprising:
   (a) contacting said NK cells with feeder cells that are genetically engineered to:
   express HLA-E-ligand for inhibitory NKG2A receptor of NK cells and simultaneously express at least one inhibitory ligand for killer cell immunoglobulin-like receptors (KIRs) selected from C1 or C2 ligand and at least one ligand selected from Bw4 or Bw6 of NK cells, resulting in a KIR-ligand:KIR match to individual donor NK cells chosen for expansion;
   express and secrete interleukin-2; and
   optionally express or are genetically engineered to express additionally at least one cytokine selected from IL-15, IL-18, and IL-21; and/or at least one activating surface molecule selected from 4-1BBL, OX40L, B7-H6, CD58, CD112/Nectin-1, CD155/Necl-5, MIC-AB, ULBP1-6, a C-type lectin-like glycoprotein selected from LLT1, AICL, and KACL; a signaling lymphocytic activating molecule (SLAM) selected from CD150, CD244, and CD4; and a viral hemagglutinin; and
   (b) cultivating said NK cells and feeder cells under conditions allowing the proliferation and expansion of said NK cells.

2. The method according to claim 1, comprising the specific induction of the proliferation and expansion of a NK cell subset expressing an activating NK cell receptor chosen from Natural Cytotoxicity Receptors (NCRs), small-tailed KIRs or NKG-receptors, comprising contacting a NK bulk cell population containing the NK subpopulation of interest with the feeder cells, wherein said feeder cells are genetically engineered to comprise an expression vector comprising a nucleic acid sequence encoding the cognate NK cell ligand for the activating NK cell receptor;
   or
   wherein said feeder cells are engineered to express a membrane-bound antibody specific for the activating NK cell receptor of the NK subpopulation of interest;
   or
   wherein said feeder cells are loaded with an activating peptide on HLA-E molecules specific for an activating receptor of the CD94/NKG2 family of the NK subpopulation of interest.

3. The method of claim 1, comprising the specific induction of the proliferation and expansion of genetically engineered NK cells displaying an artificial chimeric antigen receptor (CAR), comprising contacting CAR-NK cells with feeder cells which endogenously express the cognate surface antigen for the CAR or are genetically engineered and comprise an expression vector and which express the cognate surface ligand for the CAR, wherein said cognate ligand is represented by a viral antigen and a tumor-associated antigen (TAA);
   or
   wherein the feeder cells are engineered to express a membrane-bound antibody specific for an epitope-tag implemented in the CAR.

4. The method according to claim 1, wherein said feeder cells are eukaryotic cells.

5. The method according to claim 1, wherein said feeder cells express simultaneously HLA-E, Bw4-, C1- and C2-KIR ligands for NK cells and non-KIR binding Bw6 ligand, and therefore are matched to any NK cell from different donors.

6. The method according to claim 1, wherein said feeder cells are genetically engineered to express simultaneously at least one or both of 4-1BBL and human IL-15-DAP12mut-ITAM (m1L-15d).

7. The method according to claim 1, wherein the NK cells that are expanded comprise a nucleic acid sequence encoding a CAR for NK cells, wherein said nucleic acid sequence encodes a polypeptide which comprises a signal transduction domain selected from cytoplasmic regions of CD28, CD137 (4-1BB), CD134 (0X40), DAP10, CD3zeta, CD3epsilonRI, and DAP12 signaling adaptor;

or wherein said nucleic acid sequence encodes a CAR comprising at least one single chain fragment variable (scFv) implemented in said CAR, and the scFv is selected from scFv(9E10)-tm that comprises the amino acid sequence of SEQ ID NO: 12; scFv(MR1.1) that comprises the amino acid sequence of SEQ ID NO: 14; and scFv(AM1) that comprises the amino acid sequence of SEQ ID NO: 15;

or wherein said nucleic acid sequence encodes a CAR which comprises an epitope-tag, FLAG-epitope, VSG-G-epitope, La-epitope, an influenza hemagglutinin (HA)-epitope and/or a c-myc-epitope.

8. The method according to claim 1, wherein said feeder cells comprise an expression vector which expresses artificial β2-microglobulin-HLA-E fused to the UL40 leader sequence of HCMV strain AD169 that consists of SEQ ID NO: 3 or wherein the feeder cells are loaded with a nonamer peptide that consists of SEQ ID NO: 2 derived from the HLA-G leader sequence and the UL40 leader sequence from HCMV strain BE/1/2010.

9. The method according to claim 1, wherein said feeder cells comprise an expression vector which encodes the cognate surface-antigen for a CAR, wherein said cognate antigen is at least one tumor-associated antigen; or wherein the feeder cells are engineered to express a membrane-bound c-myc-single chain antibody specific for an epitope-tag implemented in the CAR.

10. A feeder cell, genetically engineered to:

express HLA-E-ligand for inhibitory NKG2A receptor of NK cells and simultaneously express at least one inhibitory ligand for killer cell immunoglobulin-like receptors (KIRs) selected from C1 or C2 ligand and at least one ligand selected from Bw4 or Bw6 of NK cells, resulting in a KIR-ligand:KIR match to donor NK cells chosen for expansion, and expresses and secretes interleukin-2; and optionally expresses or is genetically engineered to express additionally at least one co cytokine selected from IL-15, IL-18, and IL-21; and/or at least one activating surface molecule selected from 4-1BBL, OX40L, B7-H6, CD58, CD112/Nectin-1, CD155/Necl-5, MIC-AB, ULBP1-6, a C-type lectin-like glycoprotein belonging to the CLEC2 subfamily selected from LLT1, AICL, and KACL; a signaling lymphocytic activating molecule (SLAM) selected from CD150, CD244, and CD48; and a viral hemagglutinin.

11. The feeder cell according to claim 10, wherein said feeder cell is genetically engineered to secrete human interleukin 2 (IL-2) and expresses simultaneously at least one or both of 4-1BBL and human IL-15-DAP12mut-ITAM (m1L-15d).

12. The method according to claim 1, wherein said feeder cells are genetically engineered to express an HLA-E-UL40sp artificial ligand consisting of SEQ ID NO: 5 or consisting of SEQ ID NO: 6 on the cell surface, wherein said HLA-E-UL40sp binds specifically to the activating NKG2C NK cell receptor, resulting in the induction of the expansion of a NKG2C+subset.

13. The method according to claim 1, wherein said feeder cells are genetically engineered to express a membrane-bound antibody derivative on the cell surface or a cognate ligand for a CAR or activating NK cell receptor, wherein said membrane-bound antibody derivative or cognate ligand binds specifically to an activating NK cell receptor or to a CAR, resulting in the induction of the expansion of a NK subset of interest or CAR-NK cells.

14. The method of claim 1, wherein the NK cells expanded in step b) are selected from NKG2C+NK subsets and CAR-NK cells.

15. The method according to claim 4, wherein said feeder cells are eukaryotic cells from the prostate cancer cell line PC3.

16. The feeder cell according to claim 10, wherein said feeder cell is genetically engineered to express an HLA-E-UL40sp artificial ligand consisting of SEQ ID NO: 5 or consisting of SEQ ID NO: 6 on the cell surface, and wherein said HLA-E-UL40sp binds specifically to the activating NKG2C NK cell receptor.

17. The feeder cell according to claim 10, wherein said feeder cell is genetically engineered to express a membrane-bound antibody derivative on the cell surface or a cognate ligand for a CAR or activating NK cell receptor, and wherein said membrane-bound antibody derivative or cognate ligand binds specifically to an activating NK cell receptor or to a CAR.

* * * * *

SEQUENCE LISTING

```
<160> NUMBER OF SEQ ID NOS: 19

<210> SEQ ID NO 1
<211> LENGTH: 9
<212> TYPE: PRT
<213> ORGANISM: Artificial sequence
<220> FEATURE:
<223> OTHER INFORMATION: Synthetic peptide

<400> SEQUENCE: 1

Val Met Ala Pro Arg Thr Leu Leu Leu
1               5

<210> SEQ ID NO 2
<211> LENGTH: 9
<212> TYPE: PRT
<213> ORGANISM: Artificial sequence
<220> FEATURE:
<223> OTHER INFORMATION: Recombinant peptide

<400> SEQUENCE: 2

Val Met Ala Pro Arg Thr Leu Phe Leu
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic peptide

<400> SEQUENCE: 3

Val Met Ala Pro Arg Thr Leu Ile Leu
1               5

<210> SEQ ID NO 4
<211> LENGTH: 12
<212> TYPE: PRT
<213> ORGANISM: Artificial sequence
<220> FEATURE:
<223> OTHER INFORMATION: Recombinnt peptide

<400> SEQUENCE: 4

Val Gly Gly Thr Ser Asp Val Glu Val Asn Glu Lys
1               5                   10

<210> SEQ ID NO 5
<211> LENGTH: 505
<212> TYPE: PRT
<213> ORGANISM: Artificial sequence
<220> FEATURE:
<223> OTHER INFORMATION: Synthetic peptide
```

```
<400> SEQUENCE: 5

Met Ser Arg Ser Val Ala Leu Ala Val Leu Ala Leu Leu Ser Leu Ser
1               5                   10                  15

Gly Leu Glu Ala Val Met Ala Pro Arg Thr Leu Ile Leu Gly Gly Gly
            20                  25                  30

Gly Gly Gly Ser Gly Ala Pro Gly Ser Gly Gly Gly Ser Ile Gln Arg
        35                  40                  45

Thr Pro Lys Ile Gln Val Tyr Ser Arg His Pro Ala Glu Asn Gly Lys
    50                  55                  60

Ser Asn Phe Leu Asn Cys Tyr Val Ser Gly Phe His Pro Ser Asp Ile
65              70                  75                  80

Glu Val Asp Leu Leu Lys Asn Gly Glu Arg Ile Glu Lys Val Glu His
                85                  90                  95

Ser Asp Leu Ser Phe Ser Lys Asp Trp Ser Phe Tyr Leu Leu Tyr Tyr
            100                 105                 110

Thr Glu Phe Thr Pro Thr Glu Lys Asp Glu Tyr Ala Cys Arg Val Asn
        115                 120                 125

His Val Thr Leu Ser Gln Pro Lys Ile Val Lys Trp Asp Arg Asp Met
    130                 135                 140

Arg Ser Ala Ser Gly Gly Gly Ser Gly Gly Gly Ser Gly Gly
145             150                 155                 160

Gly Gly Ser Ala Ser Gly Gly Gly Ser His Ser Leu Lys Tyr Phe
            165                 170                 175

His Thr Ser Val Ser Arg Pro Gly Arg Gly Glu Pro Arg Phe Ile Ser
        180                 185                 190

Val Gly Tyr Val Asp Asp Thr Gln Phe Val Arg Phe Asp Asn Asp Ala
    195                 200                 205

Ala Ser Pro Arg Met Val Pro Arg Ala Pro Trp Met Glu Gln Glu Gly
210                 215                 220

Ser Glu Tyr Trp Asp Arg Glu Thr Arg Ser Ala Arg Asp Thr Ala Gln
225                 230                 235                 240

Ile Phe Arg Val Asn Leu Arg Thr Leu Arg Gly Cys Tyr Asn Gln Ser
            245                 250                 255

Glu Ala Gly Ser His Thr Leu Gln Trp Met His Gly Cys Glu Leu Gly
        260                 265                 270

Pro Asp Gly Arg Phe Leu Arg Gly Tyr Glu Gln Phe Ala Tyr Asp Gly
    275                 280                 285

Lys Asp Tyr Leu Thr Leu Asn Glu Asp Leu Arg Ser Trp Thr Ala Val
290                 295                 300

Asp Thr Ala Ala Gln Ile Ser Glu Gln Lys Ser Asn Asp Ala Ser Glu
305                 310                 315                 320

Ala Glu His Gln Arg Ala Tyr Leu Glu Asp Thr Cys Val Glu Trp Leu
            325                 330                 335

His Lys Tyr Leu Glu Lys Gly Lys Glu Thr Leu Leu His Leu Glu Pro
        340                 345                 350

Pro Lys Thr His Val Thr His His Pro Ile Ser Asp His Glu Ala Thr
    355                 360                 365

Leu Arg Cys Trp Ala Leu Gly Phe Tyr Pro Ala Glu Ile Thr Leu Thr
        370                 375                 380

Trp Gln Gln Asp Gly Glu Gly His Thr Gln Asp Thr Glu Leu Val Glu
385                 390                 395                 400

Thr Arg Pro Ala Gly Asp Gly Thr Phe Gln Lys Trp Ala Ala Val Val
```

```
                    405                 410                 415
Val Pro Ser Gly Glu Glu Gln Arg Tyr Thr Cys His Val Gln His Glu
            420                 425                 430

Gly Leu Pro Glu Pro Val Thr Leu Arg Trp Lys Pro Ala Ser Gln Pro
        435                 440                 445

Thr Ile Pro Ile Val Gly Ile Ile Ala Gly Leu Val Leu Leu Gly Ser
    450                 455                 460

Val Val Ser Gly Ala Val Val Ala Ala Val Ile Trp Arg Lys Lys Ser
465                 470                 475                 480

Ser Gly Gly Lys Gly Gly Ser Tyr Ser Lys Ala Glu Trp Ser Asp Ser
            485                 490                 495

Ala Gln Gly Ser Glu Ser His Ser Leu
        500                 505

<210> SEQ ID NO 6
<211> LENGTH: 505
<212> TYPE: PRT
<213> ORGANISM: Artificial sequence
<220> FEATURE:
<223> OTHER INFORMATION: Synthetic peptide

<400> SEQUENCE: 6

Met Ser Arg Ser Val Ala Leu Ala Val Leu Ala Leu Leu Ser Leu Ser
1               5                   10                  15

Gly Leu Glu Ala Val Met Ala Pro Arg Thr Leu Phe Leu Gly Gly Gly
            20                  25                  30

Gly Gly Gly Ser Gly Ala Pro Gly Ser Gly Gly Gly Ser Ile Gln Arg
        35                  40                  45

Thr Pro Lys Ile Gln Val Tyr Ser Arg His Pro Ala Glu Asn Gly Lys
    50                  55                  60

Ser Asn Phe Leu Asn Cys Tyr Val Ser Gly Phe His Pro Ser Asp Ile
65              70                  75                  80

Glu Val Asp Leu Leu Lys Asn Gly Glu Arg Ile Glu Lys Val Glu His
                85                  90                  95

Ser Asp Leu Ser Phe Ser Lys Asp Trp Ser Phe Tyr Leu Leu Tyr Tyr
            100                 105                 110

Thr Glu Phe Thr Pro Thr Glu Lys Asp Glu Tyr Ala Cys Arg Val Asn
        115                 120                 125

His Val Thr Leu Ser Gln Pro Lys Ile Val Lys Trp Asp Arg Asp Met
    130                 135                 140

Arg Ser Ala Ser Gly Gly Gly Ser Gly Gly Gly Gly Ser Gly Gly Gly
145                 150                 155                 160

Gly Gly Ser Ala Ser Gly Gly Gly Ser His Ser Leu Lys Tyr Phe
            165                 170                 175

His Thr Ser Val Ser Arg Pro Gly Arg Gly Glu Pro Arg Phe Ile Ser
        180                 185                 190

Val Gly Tyr Val Asp Asp Thr Gln Phe Val Arg Phe Asp Asn Asp Ala
    195                 200                 205

Ala Ser Pro Arg Met Val Pro Arg Ala Pro Trp Met Glu Gln Glu Gly
    210                 215                 220

Ser Glu Tyr Trp Asp Arg Glu Thr Arg Ser Ala Arg Asp Thr Ala Gln
225                 230                 235                 240

Ile Phe Arg Val Asn Leu Arg Thr Leu Arg Gly Cys Tyr Asn Gln Ser
            245                 250                 255

Glu Ala Gly Ser His Thr Leu Gln Trp Met His Gly Cys Glu Leu Gly
```

```
                260                 265                 270
Pro Asp Gly Arg Phe Leu Arg Gly Tyr Glu Gln Phe Ala Tyr Asp Gly
            275                 280                 285

Lys Asp Tyr Leu Thr Leu Asn Glu Asp Leu Arg Ser Trp Thr Ala Val
        290                 295                 300

Asp Thr Ala Ala Gln Ile Ser Glu Gln Lys Ser Asn Asp Ala Ser Glu
305                 310                 315                 320

Ala Glu His Gln Arg Ala Tyr Leu Glu Asp Thr Cys Val Glu Trp Leu
                325                 330                 335

His Lys Tyr Leu Glu Lys Gly Lys Glu Thr Leu Leu His Leu Glu Pro
            340                 345                 350

Pro Lys Thr His Val Thr His His Pro Ile Ser Asp His Glu Ala Thr
        355                 360                 365

Leu Arg Cys Trp Ala Leu Gly Phe Tyr Pro Ala Glu Ile Thr Leu Thr
370                 375                 380

Trp Gln Gln Asp Gly Glu Gly His Thr Gln Asp Thr Glu Leu Val Glu
385                 390                 395                 400

Thr Arg Pro Ala Gly Asp Gly Thr Phe Gln Lys Trp Ala Ala Val Val
                405                 410                 415

Val Pro Ser Gly Glu Glu Gln Arg Tyr Thr Cys His Val Gln His Glu
            420                 425                 430

Gly Leu Pro Glu Pro Val Thr Leu Arg Trp Lys Pro Ala Ser Gln Pro
        435                 440                 445

Thr Ile Pro Ile Val Gly Ile Ile Ala Gly Leu Val Leu Leu Gly Ser
    450                 455                 460

Val Val Ser Gly Ala Val Val Ala Ala Val Ile Trp Arg Lys Lys Ser
465                 470                 475                 480

Ser Gly Gly Lys Gly Gly Ser Tyr Ser Lys Ala Glu Trp Ser Asp Ser
                485                 490                 495

Ala Gln Gly Ser Glu Ser His Ser Leu
            500                 505

<210> SEQ ID NO 7
<211> LENGTH: 114
<212> TYPE: PRT
<213> ORGANISM: Artificial sequence
<220> FEATURE:
<223> OTHER INFORMATION: Synthetic peptide

<400> SEQUENCE: 7

Met Ala Gly Leu Ala Leu Gln Pro Gly Thr Ala Leu Leu Cys Tyr Ser
1               5                   10                  15

Cys Lys Ala Gln Val Ser Asn Glu Asp Cys Leu Gln Val Glu Asn Cys
            20                  25                  30

Thr Gln Leu Gly Glu Gln Cys Trp Thr Ala Arg Ile Arg Ala Val Gly
        35                  40                  45

Leu Leu Thr Val Ile Ser Lys Gly Cys Ser Leu Asn Cys Val Asp Asp
    50                  55                  60

Ser Gln Asp Tyr Tyr Val Gly Lys Lys Asn Ile Thr Cys Cys Asp Thr
65                  70                  75                  80

Asp Leu Cys Asn Ala Ser Gly Ala His Ala Leu Gln Pro Ala Ala Ala
                85                  90                  95

Ile Leu Ala Leu Leu Pro Ala Leu Gly Leu Leu Leu Trp Gly Pro Gly
            100                 105                 110

Gln Leu
```

<210> SEQ ID NO 8
<211> LENGTH: 982
<212> TYPE: PRT
<213> ORGANISM: Artificial sequence
<220> FEATURE:
<223> OTHER INFORMATION: Synthetic peptide

<400> SEQUENCE: 8

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
            20                  25                  30

Val Val Thr Asp His Gly Ser Cys Val Arg Ala Cys Gly Ala Asp Ser
        35                  40                  45

Tyr Glu Met Glu Glu Asp Gly Val Arg Lys Cys Lys Lys Cys Glu Gly
    50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
            100                 105                 110

Ser Phe Thr His Thr Pro Pro Leu Asp Pro Gln Glu Leu Asp Ile Leu
        115                 120                 125

Lys Thr Val Lys Glu Ile Thr Gly Phe Leu Leu Ile Gln Ala Trp Pro
    130                 135                 140

Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
                165                 170                 175

Asn Ile Thr Ser Leu Gly Leu Arg Ser Leu Lys Glu Ile Ser Asp Gly
            180                 185                 190

Asp Val Ile Ile Ser Gly Asn Lys Asn Leu Cys Tyr Ala Asn Thr Ile
        195                 200                 205

Asn Trp Lys Lys Leu Phe Gly Thr Ser Gly Gln Lys Thr Lys Ile Ile
    210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
            260                 265                 270

Asn Leu Leu Glu Gly Glu Pro Arg Glu Phe Val Glu Asn Ser Glu Cys
        275                 280                 285

Ile Gln Cys His Pro Glu Cys Leu Pro Gln Ala Met Asn Ile Thr Cys
    290                 295                 300

Thr Gly Arg Gly Pro Asp Asn Cys Ile Gln Cys Ala His Tyr Ile Asp
305                 310                 315                 320

Gly Pro His Cys Val Lys Thr Cys Pro Ala Gly Val Met Gly Glu Asn
                325                 330                 335

Asn Thr Leu Val Trp Lys Tyr Ala Asp Ala Gly His Val Cys His Leu
            340                 345                 350

Cys His Pro Asn Cys Thr Tyr Gly Cys Thr Gly Pro Gly Leu Glu Gly
        355                 360                 365
```

```
Cys Pro Thr Asn Gly Pro Lys Ile Pro Ser Ile Ala Thr Gly Met Val
    370             375                 380

Gly Ala Leu Leu Leu Leu Val Val Ala Leu Gly Ile Gly Leu Phe
385             390                 395                 400

Met Arg Arg Arg His Ile Val Arg Lys Arg Thr Leu Arg Arg Leu Leu
                405                 410                 415

Gln Glu Arg Glu Leu Val Glu Pro Leu Thr Pro Ser Gly Glu Ala Pro
                420                 425                 430

Asn Gln Ala Leu Leu Arg Ile Leu Lys Glu Thr Glu Phe Lys Lys Ile
            435                 440                 445

Lys Val Leu Gly Ser Gly Ala Phe Gly Thr Val Tyr Lys Gly Leu Trp
450                 455                 460

Ile Pro Glu Gly Glu Lys Val Lys Ile Pro Val Ala Ile Lys Glu Leu
465                 470                 475                 480

Arg Glu Ala Thr Ser Pro Lys Ala Asn Lys Glu Ile Leu Asp Glu Ala
                485                 490                 495

Tyr Val Met Ala Ser Val Asp Asn Pro His Val Cys Arg Leu Leu Gly
            500                 505                 510

Ile Cys Leu Thr Ser Thr Val Gln Leu Ile Thr Gln Leu Met Pro Phe
        515                 520                 525

Gly Cys Leu Leu Asp Tyr Val Arg Glu His Lys Asp Asn Ile Gly Ser
530                 535                 540

Gln Tyr Leu Leu Asn Trp Cys Val Gln Ile Ala Lys Gly Met Asn Tyr
545                 550                 555                 560

Leu Glu Asp Arg Arg Leu Val His Arg Asp Leu Ala Ala Arg Asn Val
                565                 570                 575

Leu Val Lys Thr Pro Gln His Val Lys Ile Thr Asp Phe Gly Leu Ala
            580                 585                 590

Lys Leu Leu Gly Ala Glu Glu Lys Glu Tyr His Ala Glu Gly Gly Lys
595                 600                 605

Val Pro Ile Lys Trp Met Ala Leu Glu Ser Ile Leu His Arg Ile Tyr
610                 615                 620

Thr His Gln Ser Asp Val Trp Ser Tyr Gly Val Thr Val Trp Glu Leu
625                 630                 635                 640

Met Thr Phe Gly Ser Lys Pro Tyr Asp Gly Ile Pro Ala Ser Glu Ile
                645                 650                 655

Ser Ser Ile Leu Glu Lys Gly Glu Arg Leu Pro Gln Pro Pro Ile Cys
            660                 665                 670

Thr Ile Asp Val Tyr Met Ile Met Val Lys Cys Trp Met Ile Asp Ala
        675                 680                 685

Asp Ser Arg Pro Lys Phe Arg Glu Leu Ile Ile Glu Phe Ser Lys Met
690                 695                 700

Ala Arg Asp Pro Gln Arg Tyr Leu Val Ile Gln Gly Asp Glu Arg Met
705                 710                 715                 720

His Leu Pro Ser Pro Thr Asp Ser Asn Phe Tyr Arg Ala Leu Met Asp
                725                 730                 735

Glu Glu Asp Met Asp Asp Val Val Asp Ala Asp Glu Tyr Leu Ile Pro
            740                 745                 750

Gln Gln Gly Phe Phe Ser Ser Pro Ser Thr Ser Arg Thr Pro Leu Leu
        755                 760                 765

Ser Ser Leu Ser Ala Thr Ser Asn Asn Ser Thr Val Ala Cys Ile Asp
770                 775                 780
```

```
Arg Asn Gly Leu Gln Ser Cys Pro Ile Lys Glu Asp Ser Phe Leu Gln
            785                 790                 795                 800

Arg Tyr Ser Ser Asp Pro Thr Gly Ala Leu Thr Glu Asp Ser Ile Asp
                805                 810                 815

Asp Thr Phe Leu Pro Val Pro Glu Tyr Ile Asn Gln Ser Val Pro Lys
            820                 825                 830

Arg Pro Ala Gly Ser Val Gln Asn Pro Val Tyr His Asn Gln Pro Leu
        835                 840                 845

Asn Pro Ala Pro Ser Arg Asp Pro His Tyr Gln Asp Pro His Ser Thr
    850                 855                 860

Ala Val Gly Asn Pro Glu Tyr Leu Asn Thr Val Gln Pro Thr Cys Val
865                 870                 875                 880

Asn Ser Thr Phe Asp Ser Pro Ala His Trp Ala Gln Lys Gly Ser His
            885                 890                 895

Gln Ile Ser Leu Asp Asn Pro Asp Tyr Gln Gln Asp Phe Phe Pro Lys
        900                 905                 910

Glu Ala Lys Pro Asn Gly Ile Phe Lys Gly Ser Thr Ala Glu Asn Ala
    915                 920                 925

Glu Tyr Leu Arg Val Ala Pro Gln Ser Ser Glu Phe Ile Gly Ala Gly
930                 935                 940

Ala Gly Pro Arg Arg Met Arg Pro Pro Thr Pro Gly Glu Gly Arg Gly
945                 950                 955                 960

Ser Leu Leu Thr Cys Gly Asp Val Glu Glu Asn Pro Gly Pro Gly Thr
            965                 970                 975

Ala Met Thr Glu Tyr Lys
            980

<210> SEQ ID NO 9
<211> LENGTH: 153
<212> TYPE: PRT
<213> ORGANISM: Homo sapiens

<400> SEQUENCE: 9

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr
145                 150

<210> SEQ ID NO 10
```

<211> LENGTH: 263
<212> TYPE: PRT
<213> ORGANISM: Artificial sequence
<220> FEATURE:
<223> OTHER INFORMATION: Recombinant peptide

<400> SEQUENCE: 10

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Leu Glu Glu Lys Asn Ile
130                 135                 140

Lys Glu Phe Leu Gln Ser Phe Val His Ile Val Gln Met Phe Ile Asn
145                 150                 155                 160

Thr Ser Gly Gly Ser Gly Ser Ala Cys Val Asn Glu Gln Lys Leu
                165                 170                 175

Ile Ser Glu Glu Asp Leu Gly Gly Ser Gln Ala Gln Ser Asp Cys Ser
            180                 185                 190

Cys Ser Thr Val Ser Pro Gly Val Leu Ala Gly Ile Val Met Gly Asp
        195                 200                 205

Leu Val Leu Thr Val Leu Ile Ala Leu Ala Val Tyr Phe Leu Gly Arg
210                 215                 220

Leu Val Pro Arg Gly Arg Gly Ala Ala Glu Ala Ala Thr Arg Lys Gln
225                 230                 235                 240

Arg Ile Thr Glu Thr Glu Ser Pro Ser Gln Glu Leu Gln Gly Gln Arg
                245                 250                 255

Ser Asp Val Ser Ser Asp Leu
            260

<210> SEQ ID NO 11
<211> LENGTH: 266
<212> TYPE: PRT
<213> ORGANISM: Homo sapiens

<400> SEQUENCE: 11

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
50                  55                  60

```
Ala Ala Ser Pro Arg Leu Arg Glu Gly Pro Glu Leu Ser Pro Asp Asp
 65                  70                  75                  80

Pro Ala Gly Leu Leu Asp Leu Arg Gln Gly Met Phe Ala Gln Leu Val
                 85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu Ser Tyr
                245                 250                 255

Thr Asp Ile Glu Met Asn Arg Leu Gly Lys
            260                 265

<210> SEQ ID NO 12
<211> LENGTH: 374
<212> TYPE: PRT
<213> ORGANISM: Artificial sequence
<220> FEATURE:
<223> OTHER INFORMATION: Recombinant protein

<400> SEQUENCE: 12

Met Ala Lys Ala Asn Leu Leu Val Leu Leu Cys Ala Leu Ala Ala Ala
  1               5                  10                  15

Asp Ala Gly Ser Glu Val His Leu Val Glu Ser Gly Gly Asp Leu Val
                 20                  25                  30

Lys Pro Gly Gly Ser Leu Lys Leu Ser Cys Ala Ala Ser Gly Phe Thr
             35                  40                  45

Phe Ser His Tyr Gly Met Ser Trp Val Arg Gln Thr Pro Asp Lys Arg
 50                  55                  60

Leu Glu Trp Val Ala Thr Ile Gly Ser Arg Gly Thr Tyr Thr His Tyr
 65                  70                  75                  80

Pro Asp Ser Val Lys Gly Arg Phe Thr Ile Ser Arg Asp Asn Asp Lys
                 85                  90                  95

Asn Ala Leu Tyr Leu Gln Met Asn Ser Leu Lys Ser Glu Asp Thr Ala
            100                 105                 110

Met Tyr Tyr Cys Ala Arg Arg Ser Glu Phe Tyr Tyr Tyr Gly Asn Thr
        115                 120                 125

Tyr Tyr Tyr Ser Ala Met Asp Tyr Trp Gly Gln Gly Ala Ser Val Thr
    130                 135                 140

Val Ser Ser Ala Lys Thr Thr Pro Lys Leu Glu Glu Gly Glu Phe Ser
145                 150                 155                 160
```

```
Glu Ala Arg Val Asp Ile Val Leu Thr Gln Ser Pro Ala Ser Leu Ala
            165                 170                 175

Val Ser Leu Gly Gln Arg Ala Thr Ile Ser Cys Arg Ala Ser Glu Ser
        180                 185                 190

Val Asp Asn Tyr Gly Phe Ser Phe Met Asn Trp Phe Gln Gln Lys Pro
        195                 200                 205

Gly Gln Pro Pro Lys Leu Leu Ile Tyr Ala Ile Ser Asn Arg Gly Ser
    210                 215                 220

Gly Val Pro Ala Arg Phe Ser Gly Ser Gly Ser Gly Thr Asp Phe Ser
225                 230                 235                 240

Leu Asn Ile His Pro Val Glu Glu Asp Pro Ala Met Tyr Phe Cys
                245                 250                 255

Gln Gln Thr Lys Glu Val Pro Trp Thr Phe Gly Gly Gly Thr Lys Leu
            260                 265                 270

Glu Ile Lys Gly Gly Gly Gly Ser Gly Tyr Thr Asp Ile Glu Met Asn
        275                 280                 285

Arg Leu Gly Lys Gly Gly Gly Ser Gly Gly Gly Gly Ser Ala Ser Gly
    290                 295                 300

Gly Gly His His His His His His Arg Pro Gln Gln Pro Thr Ile Pro
305                 310                 315                 320

Ile Val Gly Ile Ile Ala Gly Leu Val Leu Gly Ser Val Val Ser
                325                 330                 335

Gly Ala Val Val Ala Ala Val Ile Trp Arg Lys Lys Ser Ser Gly Gly
            340                 345                 350

Lys Gly Gly Ser Tyr Ser Lys Ala Glu Trp Ser Asp Ser Ala Gln Gly
        355                 360                 365

Ser Glu Ser His Ser Leu
    370

<210> SEQ ID NO 13
<211> LENGTH: 113
<212> TYPE: PRT
<213> ORGANISM: Artificial sequence
<220> FEATURE:
<223> OTHER INFORMATION: Recombinant peptide

<400> SEQUENCE: 13

Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
            100                 105                 110

Lys

<210> SEQ ID NO 14
<211> LENGTH: 262
<212> TYPE: PRT
```

<213> ORGANISM: Artificial sequence
<220> FEATURE:
<223> OTHER INFORMATION: Recombinant peptide)

<400> SEQUENCE: 14

Met Glu Thr Asp Thr Leu Leu Leu Trp Val Leu Leu Trp Val Pro
1               5                   10                  15

Gly Ser Thr Gly Asp Ala Gln Val Lys Leu Gln Gln Ser Gly Gly
                20                  25                  30

Leu Val Lys Pro Gly Ala Ser Leu Lys Leu Ser Cys Val Thr Ser Gly
            35                  40                  45

Phe Thr Phe Arg Lys Phe Gly Met Ser Trp Val Arg Gln Thr Ser Asp
50                  55                  60

Lys Arg Leu Glu Trp Val Ala Ser Ile Ser Thr Gly Gly Tyr Asn Thr
65                  70                  75                  80

Tyr Tyr Ser Asp Asn Val Lys Gly Arg Phe Thr Ile Ser Arg Glu Asn
                85                  90                  95

Ala Lys Asn Thr Leu Tyr Leu Gln Met Ser Ser Leu Lys Ser Glu Asp
            100                 105                 110

Thr Ala Leu Tyr Tyr Cys Thr Arg Gly Tyr Ser Pro Tyr Ser Tyr Ala
        115                 120                 125

Met Asp Tyr Trp Gly Gln Gly Thr Thr Val Thr Val Ser Ser Ser Gly
    130                 135                 140

Gly Gly Ser Gly Gly Gly Gly Ser Gly Gly Gly Gly Ser Asp Ile Glu
145                 150                 155                 160

Leu Thr Gln Ser Pro Ala Ser Leu Ser Val Ala Thr Gly Glu Lys Ala
                165                 170                 175

Thr Ile Arg Cys Met Thr Ser Thr Asp Ile Asp Asp Asp Met Asn Trp
            180                 185                 190

Tyr Gln Gln Lys Pro Gly Glu Pro Pro Lys Phe Leu Ile Ser Glu Gly
        195                 200                 205

Asn Thr Leu Arg Pro Gly Val Pro Ser Arg Phe Ser Ser Gly Thr
    210                 215                 220

Gly Thr Asp Phe Val Phe Thr Ile Glu Asn Thr Leu Ser Glu Asp Val
225                 230                 235                 240

Gly Asp Tyr Tyr Cys Leu Gln Ser Trp Asn Val Pro Leu Thr Phe Gly
                245                 250                 255

Asp Gly Thr Lys Leu Glu
            260

<210> SEQ ID NO 15
<211> LENGTH: 307
<212> TYPE: PRT
<213> ORGANISM: Artificial sequence
<220> FEATURE:
<223> OTHER INFORMATION: Recombinant peptide

<400> SEQUENCE: 15

Met Glu Thr Asp Thr Leu Leu Leu Trp Val Leu Leu Trp Val Pro
1               5                   10                  15

Gly Ser Thr Gly Asp Ala Ala Gln Pro Ala Arg Arg Ala Arg Arg Thr
                20                  25                  30

Lys Leu Gly Thr Glu Leu Gly Ser Gln Val Lys Leu Gln Glu Ser Gly
            35                  40                  45

Gly Gly Leu Val Gln Pro Gly Gly Ser Leu Lys Leu Ser Cys Val Ala
        50                  55                  60

Ser Gly Phe Thr Phe Ser Ser Tyr Thr Met Ser Trp Val Arg Arg Thr
65                  70                  75                  80

Pro Glu Lys Arg Leu Glu Trp Val Ala Tyr Ile His Asn Gly Gly Gly
                85                  90                  95

His Thr Tyr Tyr Pro Asp Thr Ile Lys Gly Arg Phe Thr Ile Ser Arg
            100                 105                 110

Asp Asn Ala Lys Asn Thr Leu Phe Leu Glu Met Ser Ser Leu Lys Ser
        115                 120                 125

Glu Asp Thr Ala Met Tyr Tyr Cys Thr Arg Arg Met Tyr Tyr Gly Asn
    130                 135                 140

Ser His Trp Tyr Phe Asp Val Trp Gly Ala Gly Thr Ser Val Thr Val
145                 150                 155                 160

Ser Ser Ala Lys Thr Thr Pro Pro Ser Val Tyr Gly Gly Gly Gly Ser
                165                 170                 175

Gly Gly Gly Gly Ser Gly Gly Gly Ser Thr Asn Ser Asp Ile Val
            180                 185                 190

Met Thr Gln Ser Pro Ser Ser Leu Ser Ala Ser Leu Gly Asp Arg Val
        195                 200                 205

Thr Ile Asn Cys Arg Thr Ser Gln Asp Ile Ser Asn Tyr Leu Asn Trp
    210                 215                 220

Tyr Gln Leu Thr Pro Asp Gly Thr Val Lys Leu Leu Ile Tyr Tyr Thr
225                 230                 235                 240

Leu Lys Leu Asn Ser Gly Val Pro Ser Arg Phe Ser Gly Ser Gly Ser
                245                 250                 255

Gly Thr Asp Tyr Ser Leu Thr Ile Asn Asn Leu Glu Lys Glu Asp Phe
            260                 265                 270

Ala Thr Tyr Phe Cys Gln Gln Ser Lys Thr Leu Pro Trp Thr Phe Gly
        275                 280                 285

Gly Gly Thr Lys Leu Glu Ile Lys Arg Ala Asp Ala Ala Pro Thr Val
    290                 295                 300

Ser Gly Pro
305

<210> SEQ ID NO 16
<211> LENGTH: 416
<212> TYPE: PRT
<213> ORGANISM: Artificial sequence
<220> FEATURE:
<223> OTHER INFORMATION: Recombinant peptide

<400> SEQUENCE: 16

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Gly Thr Glu Leu Gly Ser Gln Val Lys Leu Gln Glu Ser Gly
        35                  40                  45

Gly Gly Leu Val Gln Pro Gly Gly Ser Leu Lys Leu Ser Cys Val Ala
    50                  55                  60

Ser Gly Phe Thr Phe Ser Ser Tyr Thr Met Ser Trp Val Arg Arg Thr
65                  70                  75                  80

Pro Glu Lys Arg Leu Glu Trp Val Ala Tyr Ile His Asn Gly Gly Gly
                85                  90                  95

His Thr Tyr Tyr Pro Asp Thr Ile Lys Gly Arg Phe Thr Ile Ser Arg
            100                 105                 110

```
Asp Asn Ala Lys Asn Thr Leu Phe Leu Glu Met Ser Ser Leu Lys Ser
            115                 120                 125
Glu Asp Thr Ala Met Tyr Tyr Cys Thr Arg Arg Met Tyr Tyr Gly Asn
    130                 135                 140
Ser His Trp Tyr Phe Asp Val Trp Gly Ala Gly Thr Ser Val Thr Val
145                 150                 155                 160
Ser Ser Ala Lys Thr Thr Pro Pro Ser Val Tyr Gly Gly Gly Gly Ser
                165                 170                 175
Gly Gly Gly Gly Ser Gly Gly Gly Ser Thr Asn Ser Asp Ile Val
            180                 185                 190
Met Thr Gln Ser Pro Ser Ser Leu Ser Ala Ser Leu Gly Asp Arg Val
            195                 200                 205
Thr Ile Asn Cys Arg Thr Ser Gln Asp Ile Ser Asn Tyr Leu Asn Trp
    210                 215                 220
Tyr Gln Leu Thr Pro Asp Gly Thr Val Lys Leu Leu Ile Tyr Tyr Thr
225                 230                 235                 240
Leu Lys Leu Asn Ser Gly Val Pro Ser Arg Phe Ser Gly Ser Gly Ser
                245                 250                 255
Gly Thr Asp Tyr Ser Leu Thr Ile Asn Asn Leu Glu Lys Glu Asp Phe
            260                 265                 270
Ala Thr Tyr Phe Cys Gln Gln Ser Lys Thr Leu Pro Trp Thr Phe Gly
        275                 280                 285
Gly Gly Thr Lys Leu Glu Ile Lys Arg Ala Asp Ala Ala Pro Thr Val
            290                 295                 300
Ser Gly Pro Gly Gly Ser Gly Gly Ser Ala Cys Val Asn Glu Gln Lys
305                 310                 315                 320
Leu Ile Ser Glu Glu Asp Leu Gly Gly Ser Gln Ala Gln Ser Asp Cys
                325                 330                 335
Ser Cys Ser Thr Val Ser Pro Gly Val Leu Ala Gly Ile Val Met Gly
            340                 345                 350
Asp Leu Val Leu Thr Val Leu Ile Ala Leu Ala Val Tyr Phe Leu Gly
            355                 360                 365
Arg Leu Val Pro Arg Gly Arg Gly Ala Ala Glu Ala Ala Thr Arg Lys
        370                 375                 380
Gln Arg Ile Thr Glu Thr Glu Ser Pro Tyr Gln Glu Leu Gln Gly Gln
385                 390                 395                 400
Arg Ser Asp Val Tyr Ser Asp Leu Asn Thr Gln Arg Pro Tyr Tyr Lys
                405                 410                 415

<210> SEQ ID NO 17
<211> LENGTH: 372
<212> TYPE: PRT
<213> ORGANISM: Artificial sequence
<220> FEATURE:
<223> OTHER INFORMATION: Recombinant peptide

<400> SEQUENCE: 17

Met Glu Thr Asp Thr Leu Leu Leu Trp Val Leu Leu Leu Trp Val Pro
1               5                   10                  15
Gly Ser Thr Gly Asp Ala Gln Val Lys Leu Gln Gln Ser Gly Gly Gly
            20                  25                  30
Leu Val Lys Pro Gly Ala Ser Leu Lys Leu Ser Cys Val Thr Ser Gly
        35                  40                  45
Phe Thr Phe Arg Lys Phe Gly Met Ser Trp Val Arg Gln Thr Ser Asp
    50                  55                  60
```

Lys Arg Leu Glu Trp Val Ala Ser Ile Ser Thr Gly Gly Tyr Asn Thr
 65                  70                  75                  80

Tyr Tyr Ser Asp Asn Val Lys Gly Arg Phe Thr Ile Ser Arg Glu Asn
                 85                  90                  95

Ala Lys Asn Thr Leu Tyr Leu Gln Met Ser Ser Leu Lys Ser Glu Asp
            100                 105                 110

Thr Ala Leu Tyr Tyr Cys Thr Arg Gly Tyr Ser Pro Tyr Ser Tyr Ala
        115                 120                 125

Met Asp Tyr Trp Gly Gln Gly Thr Thr Val Thr Val Ser Ser Ser Gly
130                 135                 140

Gly Gly Ser Gly Gly Gly Ser Gly Gly Gly Ser Asp Ile Glu
145                 150                 155                 160

Leu Thr Gln Ser Pro Ala Ser Leu Ser Val Ala Thr Gly Glu Lys Ala
                165                 170                 175

Thr Ile Arg Cys Met Thr Ser Thr Asp Ile Asp Asp Met Asn Trp
            180                 185                 190

Tyr Gln Gln Lys Pro Gly Glu Pro Pro Lys Phe Leu Ile Ser Glu Gly
        195                 200                 205

Asn Thr Leu Arg Pro Gly Val Pro Ser Arg Phe Ser Ser Ser Gly Thr
210                 215                 220

Gly Thr Asp Phe Val Phe Thr Ile Glu Asn Thr Leu Ser Glu Asp Val
225                 230                 235                 240

Gly Asp Tyr Tyr Cys Leu Gln Ser Trp Asn Val Pro Leu Thr Phe Gly
                245                 250                 255

Asp Gly Thr Lys Leu Glu Ser Gly Gly Ser Gly Gly Ser Ala Cys Val
            260                 265                 270

Asn Glu Gln Lys Leu Ile Ser Glu Glu Asp Leu Gly Gly Ser Gln Ala
        275                 280                 285

Gln Ser Asp Cys Ser Cys Ser Thr Val Ser Pro Gly Val Leu Ala Gly
290                 295                 300

Ile Val Met Gly Asp Leu Val Leu Thr Val Leu Ile Ala Leu Ala Val
305                 310                 315                 320

Tyr Phe Leu Gly Arg Leu Val Pro Arg Gly Arg Gly Ala Ala Glu Ala
                325                 330                 335

Ala Thr Arg Lys Gln Arg Ile Thr Glu Thr Glu Ser Pro Tyr Gln Glu
            340                 345                 350

Leu Gln Gly Gln Arg Ser Asp Val Tyr Ser Asp Leu Asn Thr Gln Arg
        355                 360                 365

Pro Tyr Tyr Lys
    370

<210> SEQ ID NO 18
<211> LENGTH: 185
<212> TYPE: PRT
<213> ORGANISM: Artificial sequence
<220> FEATURE:
<223> OTHER INFORMATION: Recombinant peptide

<400> SEQUENCE: 18

Met Gly Gly Leu Glu Pro Cys Ser Arg Leu Leu Leu Leu Pro Leu Leu
  1               5                  10                  15

Leu Ala Val Ser Gly Leu Arg Pro Val Gln Ala Gln Ala Gln Ala Ala
             20                  25                  30

Gly Gly Arg Gly Met Ser Gly Gly Gly Ser Lys Pro Leu Pro Glu Val
         35                  40                  45

-continued

```
Thr Asp Glu Tyr Gly Gly Gly Ser Ser Ser Ala Ser Gly Gly Thr Glu
    50              55                  60

Leu Gly Ser Gln Val Lys Leu Gln Glu Ser Gly Gly Gly Ser Gly Gly
65              70                  75                  80

Ser Ala Cys Val Asn Glu Gln Lys Leu Ile Ser Glu Glu Asp Leu Gly
                85                  90                  95

Gly Ser Gln Ala Gln Ser Asp Cys Ser Cys Ser Thr Val Ser Pro Gly
                100                 105                 110

Val Leu Ala Gly Ile Val Met Gly Asp Leu Val Leu Thr Val Leu Ile
            115                 120                 125

Ala Leu Ala Val Tyr Phe Leu Gly Arg Leu Val Pro Arg Gly Arg Gly
            130                 135                 140

Ala Ala Glu Ala Ala Thr Arg Lys Gln Arg Ile Thr Glu Thr Glu Ser
145                 150                 155                 160

Pro Tyr Gln Glu Leu Gln Gly Gln Arg Ser Asp Val Tyr Ser Asp Leu
                165                 170                 175

Asn Thr Gln Arg Pro Tyr Tyr Lys Gly
                180                 185

<210> SEQ ID NO 19
<211> LENGTH: 10
<212> TYPE: PRT
<213> ORGANISM: Artificial sequence
<220> FEATURE:
<223> OTHER INFORMATION: Recombinant peptide

<400> SEQUENCE: 19

Glu Gln Lys Leu Ile Ser Glu Glu Asp Leu
1               5                   10
```